US005756494A

United States Patent [19]
Lewis et al.

[11] Patent Number: 5,756,494
[45] Date of Patent: May 26, 1998

[54] PROTEIN KINASE INHIBITORS FOR TREATMENT OF NEUROLOGICAL DISORDERS

[75] Inventors: Michael E. Lewis, West Chester; James C. Kauer, Kennett Square; Nicola Neff, Wallingford; Jill Roberts-Lewis, West Chester, all of Pa.; Chikara Murakata, Hachioji, Japan; Hiromitsu Saito, Mishima, Japan; Yuzuru Matsuda, Koganei, Japan; Marcie A. Glicksman, Swarthmore, Pa.; Fumihiko Kanai, Machida; Masami Kaneko, Sagamihara, both of Japan

[73] Assignees: Cephalon, Inc., West Chester, Pa.; Kyowa Hakko Kogyo Co., Ltd., Japan

[21] Appl. No.: 456,642

[22] Filed: Jun. 2, 1995

Related U.S. Application Data

[63] Continuation-in-part of Ser. No. 329,540, Oct. 26, 1994, which is a continuation-in-part of Ser. No. 96,561, Jul. 22, 1993, Pat. No. 5,461,146, which is a continuation-in-part of Ser. No. 920,102, Jul. 24, 1992, abandoned.

[51] Int. Cl.$^6$ .......................... C07D 498/12; A61K 31/55
[52] U.S. Cl. .............................................. 514/211; 540/545
[58] Field of Search ............................ 540/545; 514/211

[56] References Cited

U.S. PATENT DOCUMENTS

| 4,554,402 | 11/1985 | Hawkins et al. | 174/42 |
|---|---|---|---|
| 4,735,939 | 4/1988 | McCoy et al. | 514/211 |
| 4,816,450 | 3/1989 | Bell et al. | 514/25 |
| 4,877,776 | 10/1989 | Murakata | 540/472 |
| 4,923,986 | 5/1990 | Murakata et al. | 540/545 |
| 5,043,335 | 8/1991 | Kleinschroth et al. | 514/211 |
| 5,093,330 | 3/1992 | Caravatti et al. | 540/545 |
| 5,344,926 | 9/1994 | Murakata et al. | 540/545 |

FOREIGN PATENT DOCUMENTS

| A-17571/88 | 12/1988 | Australia . |
|---|---|---|
| 0 238 011 A2 | 9/1987 | European Pat. Off. . |
| 0 296 110 A3 | 12/1988 | European Pat. Off. . |
| 0 323 171 A3 | 7/1989 | European Pat. Off. . |
| 0 370 236 A1 | 5/1990 | European Pat. Off. . |
| 0 558 962 A1 | 9/1993 | European Pat. Off. . |
| 62-120388 | 6/1987 | Japan . |
| 62-155284 | 7/1987 | Japan . |
| 62-155285 | 7/1987 | Japan . |
| 63-295588 | 12/1988 | Japan . |
| 63-295589 | 12/1988 | Japan . |
| 5086068 | 4/1993 | Japan . |
| 5247055 | 9/1993 | Japan . |
| 6073063 | 3/1994 | Japan . |
| WO 88/07045 | 9/1988 | WIPO . |
| WO 89/07105 | 8/1989 | WIPO . |
| WO 91/09034 | 6/1991 | WIPO . |
| WO 93/08809 | 5/1993 | WIPO . |
| WO 94/02488 | 2/1994 | WIPO . |
| WO 95/00520 | 1/1995 | WIPO . |

OTHER PUBLICATIONS

Glicksman et al. J. Neurochem., 61, 210–221 1993.

Abe et al., "Arachidonic Acid Metabolism in Ischemic Neuronal Damage," *Annals of the New York Academy of Sciences* 559:259–268 (1989).

Borasio, "Differential effects of the protein kinase inhibitor K–252a on the in vitro survival of chick embryonic neurons," *Neuroscience Letters* 108:207–212 (1990).

Bozyczko–Coyne et al., "A rapid fluorometric assay to measure neuronal survival in vivo," *Journal of Neuroscience Methods* 50:205–216 (1993).

Chiu, A. et al., "A Motor Neuron–Specific Epitope and the Low Affinity Nerve Growth Factor Receptor Display . . . Development, Axotomy, and Regeneration," *Journal of Comparative Neurology* 328:328–363 (1993).

Chu–Wang et al., "Cell Death of Motoneurons in the Chick Embryo Spinal Cord," *J. Comp. Neur.*, 177:33–58.

Davis et al., "Inhibitors of Protein Kinase C.$1^1$ 2,3–Bisaryl-maleimides," *J. Med. Chem.* 35:177–184, 1992.

Davis et al., "Potent Selective Inhibitors of Protein Kinase C," *FEBS Letters* 259:61–63 (1989).

Dunnett, S. et al., "The basal forebrain—cortical cholinergic system: interpreting the functional consequences of excitotoxic lesions," *TINS* 14:494–501 (1991).

Fibiger, H., "Cholinergic mechanisms in learning, memory and dementia: a review of recent evidence," *TINS* 14:220–223 (1991).

Glicksman, M. et al., "K–252a and Staurosporine Promote Choline Acetyltransferase Activity in Rat Spinal Cord Cultures," *Journal of Neurochemistry* 61:210–221 (1993).

Glicksman, M., "K–252a Molecules as Promoters . . . ", Third Int. Conference on Nerve Growth Factor (NGF) and related molecule. Chateau Lake Louise, Lake Louise, Alberta, Apr. 26–May 1, 1994.

Glicksman, M. et al., "K–252a Promotes Survival of Striatal Neurons in Culture," *Society of Neuroscience Abstracts* 19:680 (1993).

Hamburger, "Cell Death in the Development of the Lateral Motor Column of the Chick Embryo," *J. Comp. Neur* 160:535–546 (1975).

Hara et al., "Staurosporine, a Novel Protein Kinase C Inhibitor, Prevents Postischemic Neuronal Damage in the Gerbil and Rat," *Journal of Cerebral Blood Flow and Metabolism* 10:646–653 (1990).

Hashimoto et al., "Staurosporine–induced Neurite Outgrowth in PC12h Cells," *Experimental Cell Research* 184:351–359 (1989).

(List continued on next page.)

Primary Examiner—Mukund J. Shah
Assistant Examiner—Pavanaram K. Sripada
Attorney, Agent, or Firm—Fish & Richardson, P.C.

[57] ABSTRACT

The invention features novel derivatives of K-252a, as well as novel bis-N-substituted derivatives of staurosporine. The invention also features a method for treating diseased neuronal cells involving the administration of either the novel staurosporine derivatives or specified functional derivatives of K-252a.

43 Claims, 22 Drawing Sheets

OTHER PUBLICATIONS

Hashimoto, "K–252a, a Potent Protein Kinase Inhibitor, Blocks Nerve Growth Factor–induced Neurite Outgrowth and Changes in the Phosphorylation of Proteins in PC12h Cells," *J. Cell Biology* 107:1531–1539.

Kase et al., "K–252a, A Protein Inhibitor of Protein Kinase C From Microbial Origin," *The Journal of Antibiotics* 39:1059–1065 (1986).

Kiyoto et al., "Staurosporine, a Potent Protein Kinase . . . Caused Ornithine Decarboxylase Induction in Isolated Mouse Epidermal Cells," *Biochem. and Biophys. Research Communications* 148:740–746 (1987).

Knüsel et al., "K–252b Selectively Potentiates Cellular Actions and *trk* Tyrosine Phosphorylation Mediated by Neurotrophin–3", *Journal of Neurochemistry* 59:715–722 (1992).

Knüsel et al., "K–252b Is a Selective and Nontoxic Inhibitor of Nerve Growth Factor Action on Cultured Brain Neurons," *Journal of Neurochemistry* 57:995–961 (1991).

Koizumi et al., "K–252a: A Specific Inhibitor of the Action of Nerve Growth Factor on PC12 Cells," *The Journal of Neuroscience* 8:715–721 (1988).

Lazarovici et al., "K–252a Inhibits the Increase in c–fos Transcription and the Increase in Intracellular Calcium Produced by Nerve Growth Factor in PC12 Cells," *Journal of Neuroscience Research* 23:1–8 (1989).

McManamann, J. et al., "Rescue of Motoneurons from Cell Death by a Purified Skeletal Muscle Polypeptide: Effects of the ChAT Development Factor, CDF," *Neuron* 4:891–898 (1990).

Matsuda et al., "The Effect of K–252a, A Potent Microbial Inhibitor of Protein Kinase, on Activated Cyclic Nucleotide Phosphodiesterase," *Biochem J.* 256:75–80 (1988).

Moody et al., "Synthesis of the Staurosporine Aglycon", *J. Org. Chem.* 57:2105–2114 (1992).

Morioka et al., "Staurosporine–induced Differentiation in a Human Neuroblastoma Cell Line, NB–1," *Agric. Biol. Chem.* 49:1959–1963 (1985).

Nabeshima et al., "Staurosporine, a protein kinase inhibitor, attenuates basal forebrain–lesion–induced amnesia and cholinergic neuronal deficit," *Neuroscience Letters* 122:13–16 (1991).

Nabeshima et al., "Staurosporine Facilitates Recovery from the Basal Forebrain–Lesion–Induced . . . Cholinergic Neuron in Rats," *The Journal of Pharmacology and Experimental Therapeutics* 257:562–566 (1991).

Nakadate et al., "Comparison of Protein Kinase C Functional Assays to Clarify Mechanisms of Inhibitor Action," *Biochemical Pharmacology* 37:1541–1545 (1988).

Nakanishi et al., "K–252b, c and d, Potent Inhibitors of Protein Kinase C From Microbial Origin," *The Journal of Antibiotics* 39:1066–1071 (1986).

Ohno et al., "Effect of Staurosporine, a Protein Kinase C Inhibitor, on Impairment of Working Memory in Rats Exposed to Cerebral Ischemia," *European Journal of Pharmacology* 204:113–116 (1991).

Olton, D. et al., "Dementia: Animal Models of the Cognitive Impairments . . . Cholinergic System," *Psychopharmacology: The Third Generation of Progress*, Raven Press, NY (1987).

Oppenheim, R. et al., "Reduction of Naturally Occurring Motoneuron Death in Vivo by a Target–Derived Neurotrophic Factor," *Science* 240:919–921 (1988).

Oppenheim, "The Absence of Significant Postnatal Motoneuron Death in the Brachial and Lumbar Spinal Cord of the Rat," *Journal of Comparative Neurology*, 246:281–286 (1986).

Oppenheim, R. et al., "Cell Death of Motoneurons in the Chick Embryo Spinal Cord. VI. Reduction of Naturally Occuring Cell Death . . . Terni by Nerve Growth Factor," *Journal of Comparative Neurology*, 210:174–189 (1982).

Rasouly et al., "Staurosporine–Induced Neurite Outgrowth in PC12–Cells is Independent of Protein Kinase–C Inhibition," *Molecular Pharmacology* 42:35–43 (1991).

Sako et al., "Contrasting Actions of Staurosporine, a Protein Kinase C Inhibitor, on Human Neurophils and Primary Mouse Epidermal Cells," *Cancer Research* 48:4646–4650 (1988).

Shea et al., "Staurosporine–induced Morphological Differentiation of Human Neuroblastoma Cells," *Cell Biology International Reports* 15:161–167 (1991).

Shepherd, "The Synaptic Organization of the Brain" Second Edition, pp. 308–314 (Oxford University Press, New York, 1979).

Siman et al., "Excitatory Amino Acids Activate Calpain I and Induce Structural Protein Breakdown in Vivo," *Neuron* 1:279–287 (1988).

Slack et al., "Effects or Retinoic Acid and Staurosporine on the Protein Kinase C Activity and the Morphology of Two Related Human Neuroblastoma Cell Lines" *Biochemica et Biophysica Acta* 1053:89–96 (1990).

Smith, G., "Animal models of Alzheimer's: experimental cholinergic denervation," *Brain Research Reviews* 13: 103–118 (1988).

Smith et al., "Effects of a Protein Kinase C Inhibitor, K–252a, on Human Polymorphonuclear Neutrophil Responsiveness," *Biochem. and Biophys. Research Communications* 152:1497–1503 (1988).

Steglich et al., "Indole Pigments from the Fruiting Bodies of the Slime Mold Arcyria denudata," *Agnew. Chem. Int. Ed. Engl.* 19:459–460 (1980).

Tischler et al., "A Protein Kinase Inhibitor, Staurosporine, Mimics Nerve Growth Factor Induction of Neurotensin/Neuromedin N Gene Expression," *The Journal of Biological Chemistry* 266:1141–1146 (1991).

Vitullo, Press Release "Cephalon and Kyowa Hakko Co., Ltd. Announce Collaboration," Jun. 2, 1992.

Wolf et al., "The Protein Kinase Inhibitor Staurosporine, Like Phorbol Esters, Induces the Association of Protein Kinase C With Membranes," *Biochem. and Biophys. Research Communications* 154:1273–1279 (1988).

Wenk, G. et al., "Nucleus basalis magnocellularis: optimal coordinates for selective reduction of choline acetyltransferase in frontal neocortex by ibotenic acid injections," *Exp Brain Res.* 56:335–340 (1984).

| COMPOUND | SPINAL CORD ChAT ACTIVITY | |
|---|---|---|
| | 300nM | 30nM |
| K-252a | 100 | - |
| II-44 | 146 | 80 |
| II-34 | 133 | 66 |
| II-47 | 126 | - |
| II-1 | 122 | - |
| II-31 | 120 | - |
| II-29 | 118 | 65 |
| II-32 | 118 | 70 |
| II-38 | 118 | - |
| II-2 | 111 | NT |
| II-3 | 109 | NT |
| II-46 | 109 | 84 |
| II-5 | 104 | NT |
| II-41 | 103 | - |
| II-42 | 102 | 64 |
| II-4 | 100 | - |
| II-30 | 94 | 71 |
| II-6 | 94 | - |
| II-7 | 90 | NT |
| II-39 | 90 | - |
| II-36 | 86 | - |
| II-8 | 85 | - |
| II-9 | 83 | 64 |
| II-10 | 81 | 143 |
| IV-3 | 77 | - |
| II-11 | 76 | NT |
| II-21 | 76 | 63 |
| III-1 | 75 | - |
| II-12 | 75 | - |
| IV-1 | 74 | 72 |
| II-13 | 73 | - |
| II-14 | 71 | - |
| II-15 | 69 | - |
| II-18 | 68 | - |
| II-16 | 68 | - |
| II-17 | 68 | NT |
| II-40 | 66 | - |
| II-19 | 66 | - |
| II-20 | 65 | 65 |
| II-45 | 65 | - |

| COMPOUND | SPINAL CORD ChAT ACTIVITY | |
|---|---|---|
| | 300nM | 30nM |
| II-22 | 62 | - |
| IV-2 | 62 | NT |
| III-2 | 60 | NT |
| II-25 | 58 | - |
| II-37 | 56 | - |
| II-23 | 55 | - |
| II-24 | 50 | - |
| II-26 | 39 | - |
| II-33 | - | 77 |
| II-43 | - | 125 |
| II-49 | - | 62 |
| II-50 | 84 | 56 |
| II-51 | 130 | 53 |
| II-52 | 103 | - |
| II-53 | 98 | 67 |
| II-54 | 51 | - |
| II-55 | 64 | - |
| II-56 | 88 | 53 |
| II-48 | 70 | - |

NT = NOT TESTED AT THAT CONCENTRATION

- = NOT ACTIVE AT THAT CONCENTRATION

FIG. 13a

| COMPOUND | SPINAL CORD ChAT ACTIVITY | |
|---|---|---|
| | 300nM | 30nM |
| II-66 | 63 | - |
| II-67 | 70 | - |
| IV-5 | 63 | - |
| II-68 | 102 | 123 |
| II-69 | 95 | 76 |
| II-70 | 107 | - |
| II-71 | 126 | 67 |
| II-65 | 158 | 79 |
| II-73 | 86 | 77 |
| II-74 | 69 | - |
| II-75 | 96 | - |
| II-76 | 97 | - |
| IV-6 | 59 | - |
| II-77 | 105 | - |
| II-78 | 94 | - |
| II-79 | 96 | 65 |
| II-80 | 116 | - |
| II-72 | 115 | 80 |
| VI-1 | 97 | - |
| VI-2 | 102 | - |

FIG. 13b

| Compound # | Spinal Cord ChAT Activity | % of K-252A |
|---|---|---|
| II-81 | - | 153 |
| II-82 | - | 147 |
| II-83 | - | 152 |
| II-84 | 104 | 117 |
| II-85 | 69 | 101 |
| II-86 | - | 65 |
| II-87 | - | 131 |
| II-88 | 89 | 113 |
| II-89 | 71 | 129 |
| II-90 | - | - |
| II-91 | 68 | - |
| II-92 | - | 84 |

FIG. 13c

| Compound # | 10uM (% Control, untreated cultures) | 100uM (% Control, untreated cultures) |
|---|---|---|
| K-252A | 151 | 215 |
| II-22 | not active | 144 |
| II-62 | not active | 147 |
| II-20 | 138 | 244 |
| II-10 | 257 | 193 |
| II-63 | 145 | not active |
| II-64 | not active | 182 |
| II-5 | 120 | 147 |
| II-21 | 126 | not active |
| II-3 | 137 | 209 |
| II-30 | 141 | 269 |
| II-32 | 160 | 174 |
| II-51 | not active | 248 |
| II-65 | 196 | 321 |

FIG. 19

| COMPOUND AT 300nM | DRG SURVIVAL | |
|---|---|---|
| | %K-252a | %NGF |
| III-1 | NT | 69 |
| III-2 | NT | 61 |
| II-21 | 95* | NT |
| II-10 | 143 | 88 |
| II-19 | NT | 107 |
| II-15 | 105 | 158 |
| II-12 | 83 | 125 |
| II-17 | 77 | 116 |
| II-5 | 100 | 110 |
| II-13 | 73 | 110 |
| II-9 | 92 | 105 |
| II-4 | 83 | 95 |
| II-20 | 55 | 84 |
| II-1 | NT | 81 |
| II-2 | NT | 77 |
| II-23 | 83 | 73 |
| II-8 | NT | 68 |
| II-3 | NT | 84 |
| II-24 | 74 | 67 |
| II-25 | 68 | 62 |
| II-11 | 90 | 57 |
| II-6 | NT | 56 |
| II-32 | 106 | NT |
| II-30 | 75 | NT |

NT = NOT TESTED
* = ONLY ACTIVE AT 30nM

FIG. 14

EFFECT OF K-252a ON SURVIVAL OF STRIATAL NEURONS *IN VITRO*

CONTROL 25 nM K-252a

| COMPOUND | STRIATAL SURVIVAL %K-252a | | |
|---|---|---|---|
| | 25nM | 75nM | 100nM |
| K-252a | - | 100 | |
| III-1 | 69 | NT | |
| II-1 | 61 | NT | 104 |
| II-35 | 52 | 81 | |
| II-20 | 58 | - | NT |
| II-10 | 91 | - | NT |
| II-28 | - | 90 | |
| II-5 | 104 | NT | |
| II-29 | 64 | NT | |
| II-2 | 65 | - | NT |
| II-3 | 50 | 104 | |
| II-30 | - | 114 | NT |
| II-6 | 81 | NT | |
| II-31 | 92 | - | NT |
| II-32 | 69 | NT | |
| IV-3 | - | NT | 47 |
| IV-1 | - | NT | 66 |
| II-33 | - | 82 | NT |
| II-34 | 118 | NT | |

NT = NOT TESTED AT THAT CONCENTRATION
- = NOT ACTIVE AT THAT CONCENTRATION

FIG. 18

Compound II-51 Reduces Axotomy-Induced Loss of ChAT Immunoreactivity in Adult Hypoglossal Nucleus Control 100 µg II-51

Compound P

Compound Q

Compound R

Compound IV-6

Compound (AA)

Compound (BB)

Compound (CC)

Compound (DD)

Compound (EE)

Compound (FF)

Compound (GG)

Compound (HH)

Compound (JJ)

PROTEIN KINASE INHIBITORS FOR TREATMENT OF NEUROLOGICAL DISORDERS

This application is a continuation-in-part of U.S. Ser. No. 08/329,540, filed Oct. 26, 1994, which is a continuation-in-part of U.S. Ser. No. 08/096,561, filed Jul. 22, 1993 parented as U.S. Pat. No. 5,461,146, which is a continuation-in-part of U.S. Ser. No. 07/920,102, filed Jul. 24, 1992, now abandoned.

BACKGROUND OF THE INVENTION

Protein kinases are a broad class of enzymes which act to modify chemically many cellular proteins, by phosphorylation of amino acids.

Inhibitors of protein kinases are structurally varied, and have variable (and sometimes contradictory) effects on the nervous system and other tissues. A given protein kinase inhibitor may influence more than one protein kinase. For example, K-252a, an alkaloid-like material isolated from the culture broth of Nocardiopsis sp. and Actinomadula sp. was originally reported to be a protein kinase C inhibitor, but was subsequently found also to inhibit protein kinases A and G, myosin light-chain kinase, and trk (a tyrosine kinase activated by nerve growth factor [NGF], the latter a neurotrophic protein which promotes the survival of peripheral, sensory and sympathetic neurons).

Consistent with this latter effect, K-252a blocks the neurotrophic actions of NGF on PC-12 cells (chromaffin cells from rat adrenal medullary tumors, pheochromocytomas), and promotes the survival of dorsal root ganglion neurons and hippocampal neurons. However, it has been found to be cytotoxic at a wide range of concentrations, leading some investigators to conclude that it has limited usefulness in vivo.

A microbial alkaloid related to K-252a, staurosporine, also has a variety of effects on different protein kinases and cell types. Staurosporine was found to have NGF-like effects on PC-12 cells, and to protect the gerbil hippocampus from post-ischemic injury. It is able to reverse damage to cholinergic neurons in the rat basal forebrain.

K-252a and staurosporine have been proposed as tumor inhibitors. Staurosporine has been offered as an insecticide. Derivatives of staurosporine, with a hydrocarbyl radical or an acyl radical substituted at the methylamine nitrogen, have been made and proposed for the following uses: tumor inhibition, inflammation inhibition, immunomodulation, and treatment of diseases of the cardiovascular and central nervous systems.

SUMMARY OF THE INVENTION

The invention features, in one aspect, novel bis-N-substituted derivatives of staurosporine, represented by the formula:

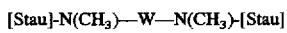

(I)

where [Stau] represents a residue of the formula:

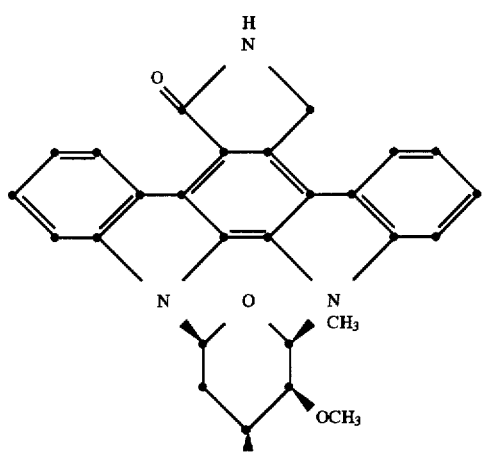

and W represents a bis(carbamyl) or bis(thiocarbamyl) radical,

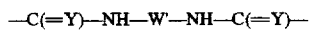

where W' is a hydrocarbylene radical of 2–20 carbon atoms and Y is O or S.

In a preferred aspect the invention features, e.g., the compounds 1,6-hexamethylene-bis-(carbamylstaurosporine) (HBCS);
p-phenylene-bis-(carbamylstaurosporine) (PBCS);

The invention also features a novel derivative of K-252a, represented by the formula (II-4):

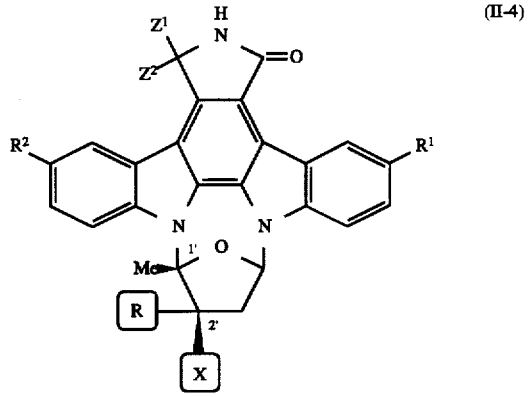

(II-4)

where $R^1$, $R^2$, $Z^1$ and $Z^2$ are each independently H; X is hydroxymethyl ($CH_2OH$); and R is $OCH_3$.

The invention also features a novel derivative of K-252a, represented by the formula:

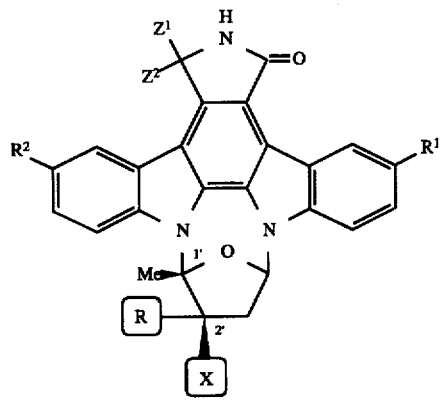

(II-14)

where $R^1$, $R^2$, $Z^1$ and $Z^2$ are each independently H; X is $CH_2$—NH-SerH; and R is OH.

Also included in the invention are compounds represented by the following Formula (II-49):

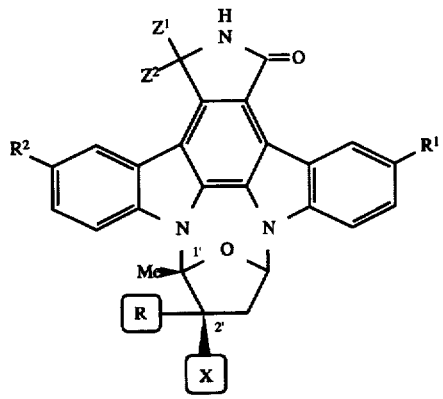

(II-49)

wherein $R^2$, $Z^1$, and $Z^2$ are each H; R is OH; $R^1$ is $CH_2SO_2C_2H_5$; and X is $CO_2CH_3$.

Also included in the invention are compounds represented by the following Formula (II-38):

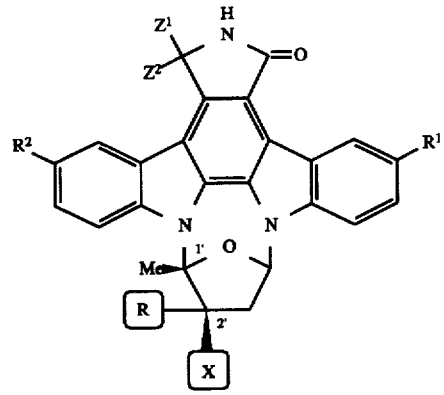

(II-38)

wherein $R^1$, $R^2$, $Z^1$, and $Z^2$ are each H; R is OH; and X is $CH_2NHCO_2C_6H_5$.

Also included in the invention are compounds represented by the following Formula (II-45):

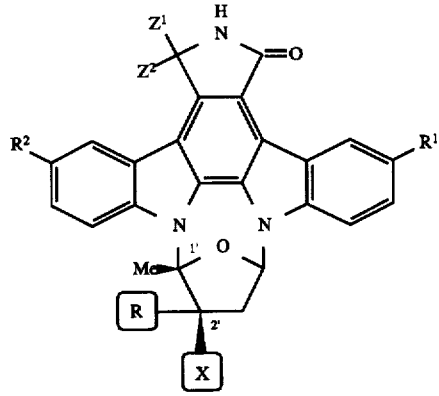

(II-45)

wherein $R^1$ and $R^2$ are each Br; R is OH; $Z^1$ and $Z^2$ are each H; and X is $CONHC_6H_5$.

Also included in the invention are compounds represented by the following Formula (II-57):

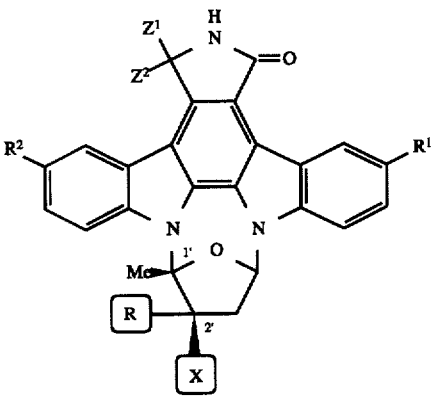

(II-57)

wherein $R^1$, $R^2$, $Z^1$, and $Z^2$ are each H, R is OH; and X is $CH_2NHCO_2CH_3$.

Also included in the invention are compounds represented by the following Formula (II-72):

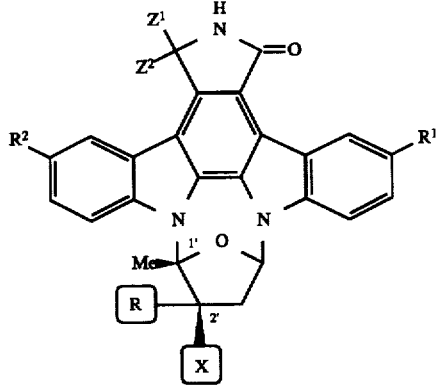

(II-72)

wherein $R^1$ is $CH_2S(CH_2)_2NH_2$; X is $CO_2CH_3$; R is OH; and $R^2$, $Z^1$, and $Z^2$ are each H.

Also included in the invention are compounds represented by the following Formula (II-75):

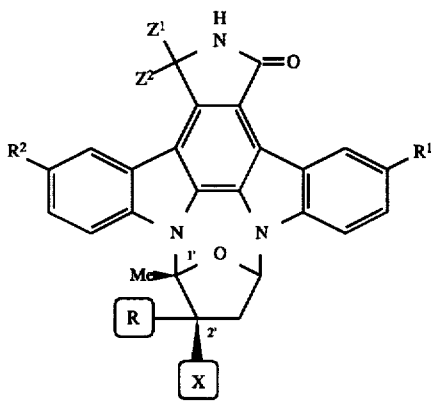
(II-75)

wherein R¹ is

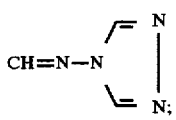

X is CO₂CH₃; R is OH; and R², Z¹, and Z² are each H.

Also included in the invention are compounds represented by the following Formula (II-79):

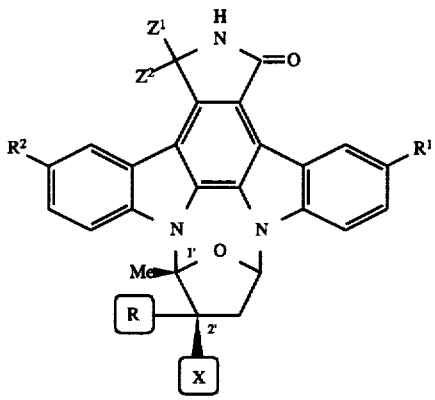
(II-79)

wherein R¹ is CH₂S(CH₂)₂NH n—C₄H₉, X is CO₂CH₃; R is OH; and R², Z¹, and Z² are each H.

Also included in the invention are compounds represented by the following Formula (II-80):

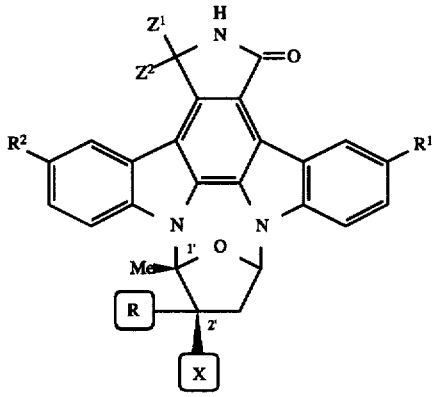
(II-80)

wherein R¹ is CH₂S(CH₂)₂N(CH₃)₂; R² is CH₂S(CH₂)₂N(CH₃)₂; X is CO₂CH₃; R is OH; and Z¹ and Z² are each H.

Also included in the invention are compounds represented by the following Formula (V):

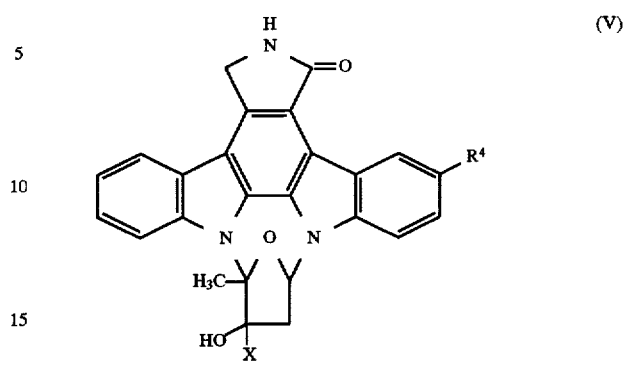
(V)

in which X represents CO₂R⁵ (in which R⁵ represents lower alkyl) or CH₂NHCO₂R⁶ (in which R⁶ represents lower alkyl or aryl); R¹ represents hydrogen or CH₂SO₂R⁷ (in which R⁷ represents lower alkyl), provided that the combination of X=CO₂R⁵ and R¹=hydrogen is excluded.

In the definitions of the groups in Formula (V), lower alkyl means a straight-chain or branched alkyl group having 1 to 6 carbon atoms, preferably 1 to 3 carbon atoms, such as methyl, ethyl, propyl, isopropyl, butyl, isobutyl, sec-butyl, tert-butyl, pentyl, neopentyl, and hexyl. Aryl means an aryl group having 6 to 10 carbon atoms, such as phenyl and naphthyl.

Also included in the invention are compounds (VI-1) represented by the following Formula (VI):

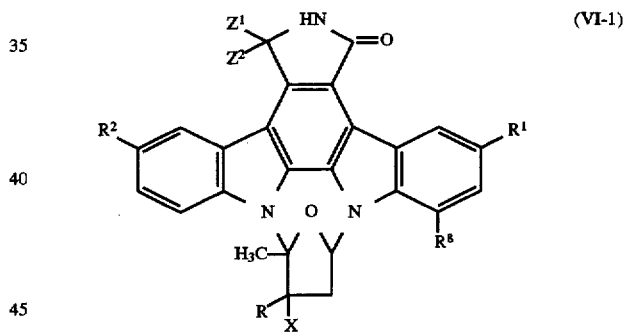
(VI-1)

wherein X is CO₂CH₃; R is OH; each R¹, R², Z¹, and Z² is H; and R⁸ is NHCONHC₂H₅.

Also included in the invention are compounds (VI-2) represented by the Formula (VI):

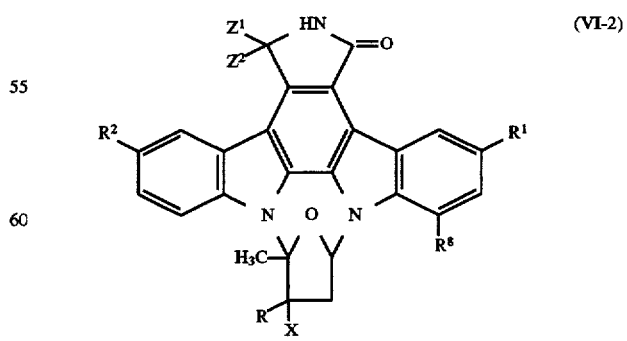
(VI-2)

wherein X is CO₂CH₃; each R² and R⁸ is NH₂; R is OH; and each R¹, Z¹, and Z² is H.

The compounds of the invention can be in the form of pharmaceutically acceptable salts including pharmaceutically acceptable acid addition salts, metal salts, ammonium salts, organic amine addition salts, and amino acid addition salts.

Examples of the pharmaceutically acceptable acid addition salts are inorganic acid addition salts such as hydrochloride, sulfate, and phosphate; and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminium salt, and zinc salt. Examples of the pharmaceutically acceptable ammonium salts are ammonium salt and tetraethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

In another aspect, the invention features a method for enhancing the function of cholinergic neurons, striatal neurons, basal forebrain neurons, and sensory neurons, e.g., dorsal root ganglion neurons, by administering to a mammal, e.g., a human, a therapeutic amount of one of the novel bis-substituted derivatives of staurosporine. The therapy may be given in conjunction with a trophic factor, preferably a member of the neurotrophin family, and most preferably nerve growth factor (NGF). As used herein, a "trophic factor" is a molecule that directly or indirectly affects the survival or function of a trophic factor-responsive cell. The neurotrophin family is a group of proteins with significant homology to NGF and include, in addition to NGF, brain-derived neurotrophic factor (BDNF; Leibrock et al., Nature 341:149–152, 1989); neutrotrophin-3 (NT-3; Hohn et al., Nature 344:339–341, 1990); and neurotrophin-5 (NT-4/5; Berkemeier et al., Neuron 7:857–866, 1991).

In another aspect, the invention features a method for protecting nerve cells of a mammal, e.g., a human, from degeneration induced by excitatory amino acids, by administering to the mammal a therapeutic amount of one of the novel bis-substituted derivatives of staurosporine. Conditions in which such degeneration may occur include Alzheimer's disease; motor neuron disease, e.g., amyotrophic lateral sclerosis; Parkinson's disease; cerebrovascular disease, e.g., ischemic conditions; AIDS dementia; epilepsy; Huntington's disease; and concussive or penetrating injuries to the brain or spinal cord. The therapy may be given in conjunction with a neurotrophic factor, preferably a member of the neurotrophin family, most preferably nerve growth factor (NGF).

In another aspect, the invention features a method for enhancing the function of cholinergic neurons, striatal neurons, basal forebrain neurons, and/or sensory neurons, e.g., dorsal root ganglion neurons, in a mammal, e.g., a human, by administering to the mammal a therapeutic amount of a functional derivative of K-252a, represented by the formulas:

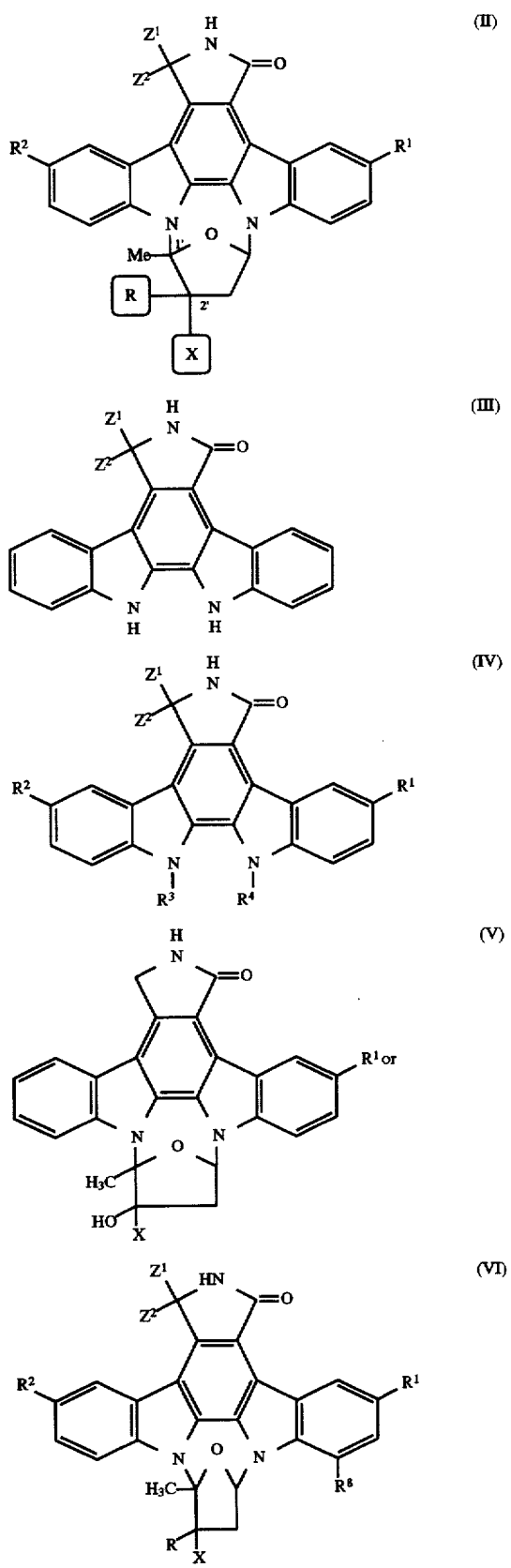

with any of the substitutions shown in Table 1, below. Preferably, the method for enhancing the function and/or survival of a cholinergic neuron, striatal neuron, basal forebrain neuron, and/or sensory neuron, e.g., a dorsal root ganglion neuron, in a mammal involves administering an effective amount of, e.g., Compound II-3, II-20, II-30, II-33, II-38, II-49, II-51, II-65, II-69, II-72, II-73, II-79, II-80, VI-1, or VI-2 of Table 1 to the mammal. More preferably, the method for enhancing the function and/or survival of a cholinergic neuron, striatal neuron, basal forebrain neuron, or sensory neuon in a mammal involves administering an effective amount of Compound II-51.

TABLE 1

| Compound | $R^1$ | $R^2$ | X | R | $Z^{1(1)}$ $Z^2$ |
|---|---|---|---|---|---|
| II-1 | H | H | $CH_2N_3$ | OH | H |
| II-2 | $NHCONHC_6H_5$ | H | $CO_2CH_3$ | OH | H |
| II-3 | $CH_2SOC_2H_5$ | H | $CO_2CH_3$ | OH | H |
| II-4 | H | H | $CH_2OH$ | $OCH_3$ | H |
| II-5 | H | H | $CONHC_2H_5$ | OH | H |
| II-6 | H | H | 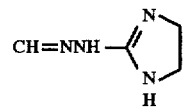 | OH | H |
| II-7(2,7) | H | H | $CH_2NH$—Gly | OH | H |
| II-8 | H | H | $CON(CH_3)_2$ | OH | H |
| II-9(3) | H | H | —$CH_2NHCO_2$— | | H |
| II-10 | Br | H | $CO_2CH_3$ | OH | H |
| II-11 | H | H | $CONH_2$ | OH | H |
| II-12 | H | H | $CH_2OH$ | OH | H |
| II-13 | H | H | $CONHC_3H_7$ | OH | H |
| II-14(2) | H | H | $CH_2NH$—Ser | OH | H |
| II-15 | H | H | $CH_2SOCH_3$ | OH | H |
| II-16 | H | H | $CH$=NOH | OH | H |
| II-17 | H | H |  | OH | H |
| II-18(2,7) | H | H | $CH_2NH$—Pro | OH | H |
| II-19 | H | H | $CH$=$NNHC($=$NH)NH_2$ | OH | H |
| II-20 | Br | Br | $CO_2CH_3$ | OH | O |
| II-21 | H | H | $CONH(CH_2)_2OH$ | OH | H |
| II-22 | H | H | $CO_2CH_3$ | OH | O |
| II-23 | H | H | H | OH | H |
| II-24 | H | H | $CH$=$NNHCONH_2$ | OH | H |
| II-25 | H | H | $CH_2OCOCH_3$ | OH | H |
| II-26(3) | H | H | —$CH_2OC(CH_3)_2O$— | | H |
| II-29 | $NHCONHC_2H_5$ | H | $CO_2CH_3$ | OH | H |
| II-30 | $CH_2SC_2H_5$ | H | $CO_2CH_3$ | OH | H |
| II-31 | Br | H | $CH_2OH$ | OH | H |
| II-32 | Br | Br | $CO_2CH_3$ | OH | H |
| II-33 | $CH_2SC_6H_5$ | H | $CO_2CH_3$ | OH | H |
| II-34 | Cl | Cl | $CO_2CH_3$ | OH | H |
| II-36 | H | H | $CONHC_6H_5$ | OH | H |
| II-37 | H | H | 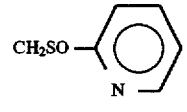 | OH | H |
| II-38 | H | H | $CH_2NHCO_2C_6H_5$ | OH | H |
| II-39 | $NHCONHC_2H_5$ | $NHCONHC_2H_5$ | $CO_2CH_3$ | OH | H |
| II-40 | $N(CH_3)_2$ | H | $CO_2CH_3$ | OH | H |
| II-41 | $CH_3$ | H | $CO_2CH_3$ | OH | H |
| II-42 | $CH_2OCONHC_2H_5$ | H | $CO_2CH_3$ | OH | H |
| II-43 | $NHCO_2CH_3$ | H | $CO_2CH_3$ | OH | H |
| II-44 | Br | Br | $CH_2OH$ | OH | H |
| II-45 | Br | Br | $CONHC_6H_5$ | OH | H |
| II-46 | Br | Br | $CONHCH_2CH_2OH$ | OH | H |
| II-47 | $CH_2OC_2H_5$ | H | $CO_2CH_3$ | OH | H |
| II-48 | $CH_2N(CH_3)_2$ | H | $CO_2CH_3$ | OH | H |
| II-49 | $CH_2SO_2C_2H_5$ | H | $CO_2CH_3$ | OH | H |
| II-50 | 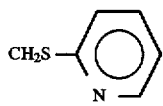 | H | $CO_2CH_3$ | OH | H |

TABLE 1-continued

| Compound | R¹ | R² | X | R | $Z^{1(1)}$ $Z^2$ |
|---|---|---|---|---|---|
| II-51 | $CH_2SC_2H_5$ | $CH_2SC_2H_5$ | $CO_2CH_3$ | OH | H |
| II-52 | CH=NNH-(4,5-dihydroimidazol-2-yl) | H | $CO_2CH_3$ | OH | H |
| II-53 | $CH_3S$-(pyrimidin-2-yl) | H | $CO_2CH_3$ | OH | H |
| II-54 | $CH_3S(O)$-(pyrimidin-2-yl) | H | $CO_2CH_3$ | OH | H |
| II-55 | $CH_3S(O)$-(pyridin-2-yl) | H | $CO_2CH_3$ | OH | H |
| II-56 | $CH_2SC_2H_5$ | $CH_2OH$ | $CO_2CH_3$ | OH | H |
| II-57 | H | H | $CH_2NHCO_2CH_3$ | OH | H |
| II-58 | Br | H | $CONH_2$ | OH | H |
| II-59 | H | H | $CH_2SC_6H_5$ | OH | H |
| II-60 | H | H | $CH_3S$-(pyridin-2-yl) | OH | H |
| II-61 | H | H | $CH_2SOC_6H_5$ | OH | H |
| II-62 | H | H | $CO_2$n-hexyl | OH | H |
| II-63 | OH | H | $CO_2CH_3$ | OH | H |
| II-64 | O n-propyl | H | $CO_2CH_3$ | OH | H |
| II-65 | $CH_2SCH_2CH_2N(CH_3)_2$ | H | $CO_2CH_3$ | OH | H |
| II-66 | H | H | $CH_2NH_2$ | OH | H |
| II-67 | H | H | $CONHCH_3$ | OH | H |
| II-68 | $CH_3S$-(benzimidazol-2-yl) | H | $CO_2CH_3$ | OH | H |
| II-69 | $CH_2SCH_2$-(furan-2-yl) | H | $CO_2CH_3$ | OH | H |
| II-70 | CH=N-N(4,5-dihydropyrazol-1-yl) | H | $CO_2CH_3$ | OH | H |
| II-71 | CH=NNH-(pyridin-2-yl) | H | $CO_2CH_3$ | OH | H |
| II-72 | $CH_2S(CH_2)_2NH_2$ | H | $CO_2CH_3$ | OH | H |
| II-73 | $CH_3S$-(1,2,4-triazol-3-yl) | H | $CO_2CH_3$ | OH | H |
| II-74 | CH=NNH-C(=NH)NH₂ | H | $CO_2CH_3$ | OH | H |

TABLE 1-continued

| Compound | $R^1$ | $R^2$ | X | R | $Z^{1(1)}$ $Z^2$ |
|---|---|---|---|---|---|
| II-75 | CH=N—N⟨pyrimidine ring⟩ (fused N=/=N) | H | $CO_2CH_3$ | OH | H |
| II-76 | CH=N—N⟨morpholine⟩ | H | $CO_2CH_3$ | OH | H |
| II-77 | $CH=N-N(CH_3)_2$ | H | $CO_2CH_3$ | OH | H |
| II-78 | CH=N—N⟨piperazine-NCH_3⟩ | H | $CO_2CH_3$ | OH | H |
| II-79 | $CH_2S(CH_2)_2NH-n-C_4H_9$ | H | $CO_2CH_3$ | OH | H |
| II-80 | $CH_2S-(CH_2)_2N(CH_3)_2$ | $CH_2S(CH_2)_2-N(CH_3)_2$ | $CO_2CH_3$ | OH | H |
| II-81 | $CH_2SCH(CH_3)_2$ | $CH_2SCH(CH_3)_2$ | $CO_2CH_3$ | OH | H |
| II-82 | $CH_2S(CH_2)_2CH_3$ | $CH_2S(CH_2)_2CH_3$ | $CO_2CH_3$ | OH | H |
| II-83 | $CH_2S(CH_2)_3CH_3$ | $CH_2S(CH_2)_3CH_3$ | $CO_2CH_3$ | OH | H |
| II-84 | $CH_2OCH_3$ | $CH_2OCH_3$ | $CO_2CH_3$ | OH | H |
| II-85 | $CH_2OC_2H_5$ | $CH_2OC_2H_5$ | $CO_2CH_3$ | OH | H |
| II-86 | $CH_2OH$ | $NHCONHC_2H_5$ | $CO_2CH_3$ | OH | H |
| II-87 | $CH_2SC_2H_5$ | $NHCONHC_2H_5$ | $CO_2CH_3$ | OH | H |
| II-88 | $CH_3$ | $CH_3$ | $CO_2CH_3$ | OH | H |
| II-89 | $CH_2SC_2H_5$ | $CH_2S(O)C_2H_5$ | $CO_2CH_3$ | OH | H |
| II-90 | $CH_2OH$ | $CH_2OH$ | $CO_2CH$ | OH | H |
| II-91 | $CH(-SCH_2CH_2S-)$ | $NO_2$ | $CO_2CH_3$ | OH | H |
| II-92 | $CH(-SCH_2CH_2S-)$ | $NHCONHC_2H_5$ | $CO_2CH_3$ | OH | H |
| III-1 | — | — | — | — | H |
| III-2 | — | — | — | — | O |
| IV-1(4,9) | H | H | — | — | H |
| IV-2(5) | Br | H | — | — | H |
| IV-3(6) | H | H | — | — | H |
| IV-4(8,9) | H | H | — | — | H |
| IV-5(10) | H | H | — | — | H |
| IV-6(7,11) | H | H | — | — | H |
| VI-1(12) | H | H | $CO_2CH_3$ | OH | H |
| VI-2(13) | H | $NH_2$ | $CO_2CH_3$ | OH | H |

(1)$Z^1$ and $Z^2$ are both hydrogen, or both are combined together to represent oxygen, where indicated.
(2)NH-amino acid linkage is an amide bond through the carboxyl group of the amino acid.
(3)X and R are combined together to form the linking group.
(4)$R^3$ is $CH_2CH=CH_2$; $R^4$ is H.
(5)$R^3$ and $R^4$ are each H.
(6)$R^3$ and $R^4$ are each $CH_2CH=CH_2$.
(7)Compound is in the form of the hydrochloride.
(8)$R^3$ is H and $R^4$ is $CH_2CH=CH_2$.
(9)IV-1 and IV-4 are a 1.5 to 1.0 mixture of the two components.
(10)$R^3 = R^4 = CH_2CH_2CH_2OH$

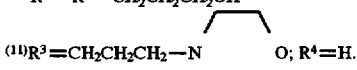

(11)$R^3 = CH_2CH_2CH_2-N$⟨morpholine⟩O; $R^4 = H$.
(12)$R^8 = NHCONHC_2H_5$.
(13)$R^8 = NH_2$.

The therapy may be given in conjunction with a trophic factor, preferably a member of the neurotrophin family, most preferably nerve growth factor (NGF).

In a preferred aspect, the invention features a method for enhancing the function of a dorsal root ganglion nerve cell, by administering to a mammal, e.g., a human, a therapeutic amount of a functional derivative of K-252a, represented by the formula (II) or (III):

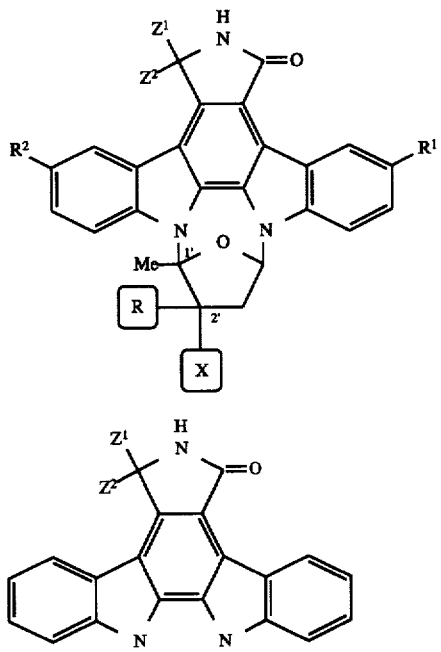

wherein the following substitutions are made:

In a preferred aspect, the invention features a method for enhancing the function of cholinergic neurons of a mammal, e.g., a human, by administering to the mammal a therapeutic amount of K-252a, represented by the formula (II):

(II)

wherein $R^1$ and $R^2$ are each H, X is $CO_2CH_3$, R is OH, and $Z^1$ and $Z^2$ are each H. The therapy may be given in conjunction with a trophic factor, preferably a member of the neurotrophin family, most preferably nerve growth factor (NGF).

In a preferred aspect, the invention features a method for enhancing the survival and/or function of a striatal nerve cell, by administering to a mammal, e.g., a human, a

TABLE 2

| Compound[1] | $R^1$ | X | R | $Z^{1(2)}$ $Z^2$ |
|---|---|---|---|---|
| II-1 | H | $CH_2N_3$ | OH | H |
| II-2 | $NHCONHC_6H_5$ | $CO_2CH_3$ | OH | H |
| II-3 | $CH_2SOC_2H_5$ | $CO_2CH_3$ | OH | H |
| II-4 | H | $CH_2OH$ | $OCH_3$ | H |
| II-5 | H | $CONHC_2H_5$ | OH | H |
| II-6 | H | CH=NNH—(imidazoline) | OH | H |
| II-8 | H | $CON(CH_3)_2$ | OH | H |
| II-9[3] | H | $-CH_2NHCO_2-$ | | H |
| II-10 | Br | $CO_2CH_3$ | OH | H |
| II-11 | H | $CONH_2$ | OH | H |
| II-12 | H | $CH_2OH$ | OH | H |
| III-1 | — | — | — | H |
| II-13 | H | $CONHC_3H_7$ | OH | H |
| II-15 | H | $CH_2SOCH_3$ | OH | H |
| II-17 | H | CON(morpholino) | OH | H |
| II-19 | H | $CH=NNHC(=NH)NH_2$ | OH | H |
| II-20[1] | Br | $CO_2CH_3$ | OH | O |
| II-21 | H | $CONH(CH_2)_2OH$ | OH | H |
| III-2 | — | — | — | O |
| II-23 | H | H | OH | H |
| II-24 | H | $CH=NNHCONH_2$ | OH | H |
| II-25 | H | $CH_2OCOCH_3$ | OH | H |
| II-30 | $CH_2SC_2H_5$ | $CO_2CH_3$ | OH | H |
| II-32 | Br | $CO_2CH_3$ | OH | H |

[1] $R^2$ is hydrogen, except in compound II-20 and II-32 where $R^2$=Br.
[2] $Z^1$ and $Z^2$ are both hydrogen, or both are combined together to represent oxygen, where indicated.
[3] X and R are combined together to form the linking group.

The therapy may be given in conjunction with a neurotrophic factor, preferably a member of the neurotrophin family, most preferably nerve growth factor (NGF).

therapeutic amount of K-252a or a functional derivative of K-252a, represented by the formulae (II), (III), or (IV):

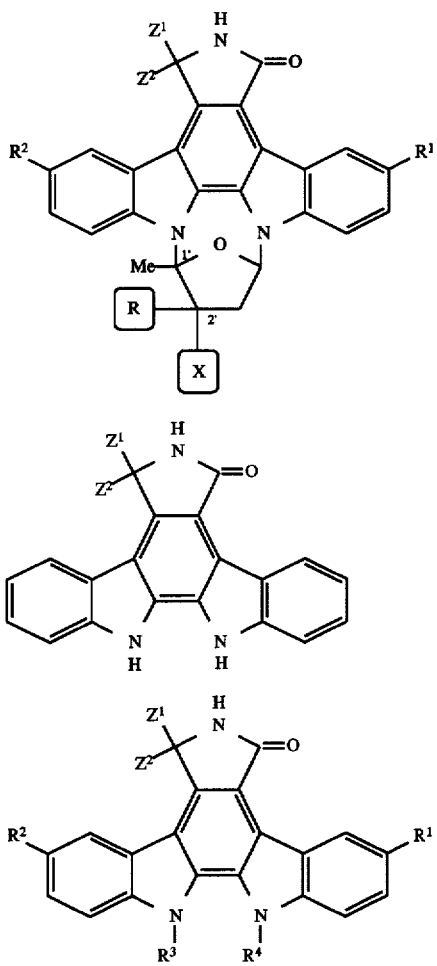

wherein the following substitutions are made:

TABLE 3

| Compound | R¹ | R² | X | R | Z²⁽¹⁾ Z¹ |
|---|---|---|---|---|---|
| K-252a | H | H | $CO_2CH_3$ | OH | H |
| III-1 | — | — | — | — | H |
| II-1 | H | H | $CH_2N$ | OH | H |
| II-35 | H | H | $CO_2$n-$C_6H_{13}$ | OH | H |
| II-20 | Br | Br | $CO_2CH_3$ | OH | O |
| II-10 | Br | H | $CO_2CH_3$ | OH | H |

TABLE 3-continued

| Compound | R¹ | R² | X | R | Z²⁽¹⁾ Z¹ |
|---|---|---|---|---|---|
| II-28 | O-n-$C_3H_7$ | H | $CO_2CH_3$ | OH | H |
| II-5 | H | H | $CONHC_2H_5$ | OH | H |
| II-29 | $NHCONHC_2H_5$ | H | $CO_2CH_3$ | OH | H |
| II-2 | $NHCONHC_6H_5$ | H | $CO_2CH_3$ | OH | H |
| II-3 | $CH_2SOC_2H_5$ | H | $CO_2CH_3$ | OH | H |
| II-30 | $CH_2SC_2H_5$ | H | $CO_2CH_3$ | OH | H |
| II-6 | H | H | CH=NNH—(imidazoline) | OH | H |
| II-31 | Br | H | $CH_2OH$ | OH | H |
| II-32 | Br | Br | $CO_2CH_3$ | OH | H |
| IV-1⁽²⁾ | — | H | — | — | H |
| II-33 | $CH_2SC_6H_5$ | H | $CO_2CH_3$ | OH | H |
| II-34 | Cl | Cl | $CO_2CH_3$ | OH | H |

⁽¹⁾$Z^1$ and $Z^2$ are both hydrogen, or both are combined together to represent oxygen, where indicated.
⁽²⁾$R^3$ is $CH_2$—CH=$CH_2$; $R^4$ is H.

In another aspect, the invention features a method for enhancing the survival and/or function of a basal forebrain nerve cell, by administering to a mammal, e.g., a human, a therapeutic amount of K-252a or a functional derivative of K-252a, represented by the formula (II):

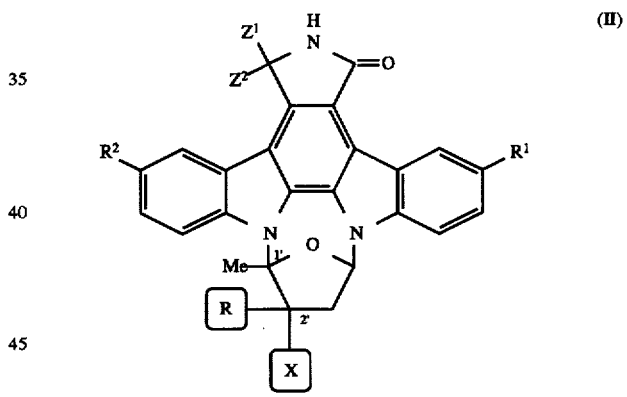

(II)

wherein the following substitutions are made:

TABLE 4

| Compound | R¹ | R² | X | R | Z², Z¹⁽¹⁾ |
|---|---|---|---|---|---|
| K-252a | H | H | $CO_2CH_3$ | OH | H |
| II-3 | $CH_2SOC_2H_5$ | H | $CO_2CH_3$ | OH | H |
| II-5 | H | H | $CONHC_2H_5$ | OH | H |
| II-10 | Br | H | $CO_2CH_3$ | OH | H |
| II-20 | Br | Br | $CO_2CH_3$ | OH | O |
| II-21 | H | H | $CONH(CH_2)_2OH$ | OH | H |
| II-22 | H | H | $CO_2CH_3$ | OH | O |
| II-30 | $CH_2SC_2H_5$ | H | $CO_2CH_3$ | OH | H |
| II-32 | Br | Br | $CO_2CH_3$ | OH | H |
| II-51 | $CH_2SC_2H_5$ | $CH_2SC_2H_5$ | $CO_2CH_3$ | OH | H |
| II-62 | H | H | $CO_2$n-hexyl | OH | H |
| II-63 | OH | H | $CO_2CH_3$ | OH | H |
| II-64 | O n-propyl | H | $CO_2CH_3$ | OH | H |

TABLE 4-continued

| Compound | R¹ | R² | X | R | Z², Z¹⁽¹⁾ |
|---|---|---|---|---|---|
| II-65 | $CH_2SCH_2CH_2N(CH_3)_2$ | H | $CO_2CH_3$ | OH | H |

⁽¹⁾$Z^1$ and $Z^2$ are both hydrogen, or both are combined together to represent oxygen, where indicated.

The therapy may be given in conjunction with a trophic factor, preferably a member of the neurotrophin family, most preferably nerve growth factor.

Other features and advantages of the invention will be apparent from the following description of the preferred embodiments thereof, and from the claims.

DESCRIPTION OF THE PREFERRED EMBODIMENTS
The drawings are first described.

Drawings FIG. 1 is a graph illustrating the effect of the K-252a derivatives 1,6-hexamethylene-bis-(carbamylstaurosporine) (HBCS) and staurosporine on basal ornithine decarboxylase (ODC) activity in PC-12 cells.

FIGS. 13a, 13b and 13c are tables showing the relative activity of K-252a derivatives on ChAT activity in rat spinal cord cultures.

FIG. 14 is a table showing the relative activity of K-252a derivatives on neuronal survival in chick dorsal root ganglion cultures.

FIG. 15 is a graph illustrating survival of striatal neurons in the presence of K-252a.

FIG. 16 is a graph illustrating the time course of survival of striatal cells in the presence of K-252a.

FIG. 17 is a pair of photomicrographs of striatal neurons cultured in the presence or absence of K-252a.

FIG. 18 is a table showing the relative activity of K-252a derivatives on neuronal survival in rat striatal cultures.

FIG. 19 is a table showing the relative activity of K-252a derivatives on the survival of low density basal forebrain neurons.

STAUROSPORINE DERIVATIVES

Figure 1:
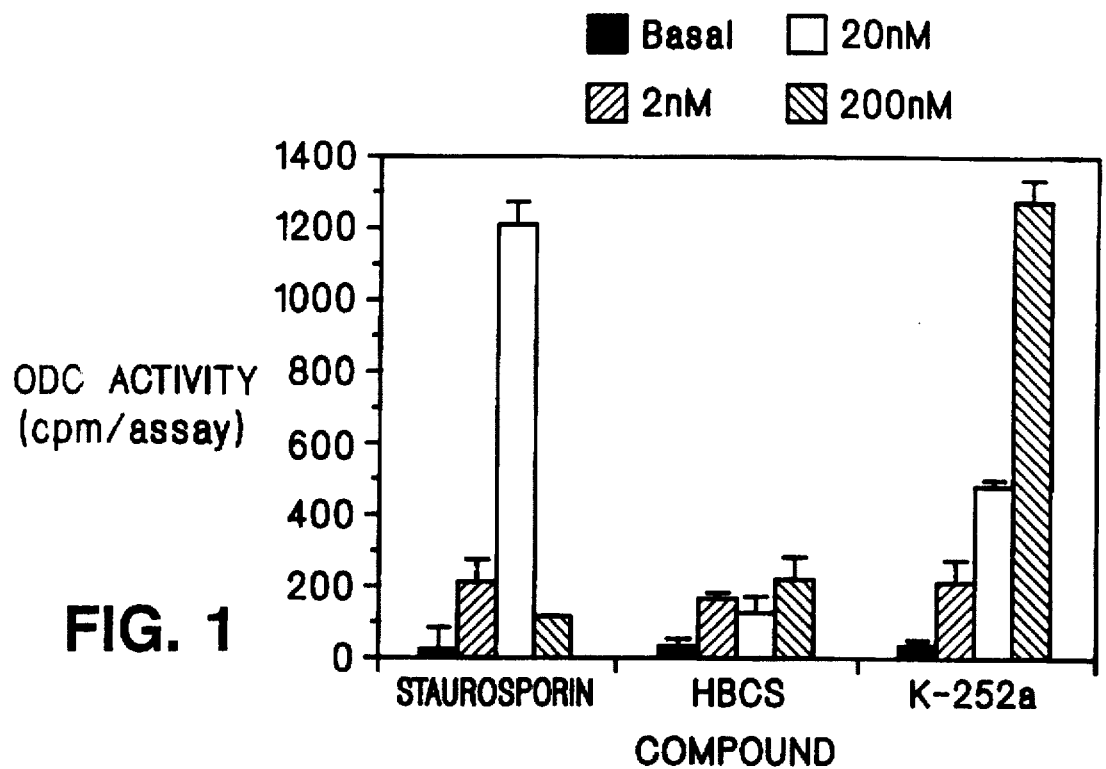

The present invention relates to novel bis-N-substituted derivatives of staurosporine and their use as therapeutics for neurological diseases, especially those diseases characterized either by neuronal cells which are injured, compromised, undergoing axonal degeneration, or at increased risk of dying, or by impaired cholinergic activity. These diseases include those induced by excitatory amino acids. The therapeutic use of these novel derivatives includes use of the derivatives alone and use of the derivatives combined with exogenous administration of neurotrophic factors (preferably members of the neurotrophin family, most preferably NGF. The compounds within the scope of this invention may be represented by the formula

[Stau]-N(CH₃)—W—N(CH₃)-[Stau]   (I)

in which [Stau] represents a residue of the formula:

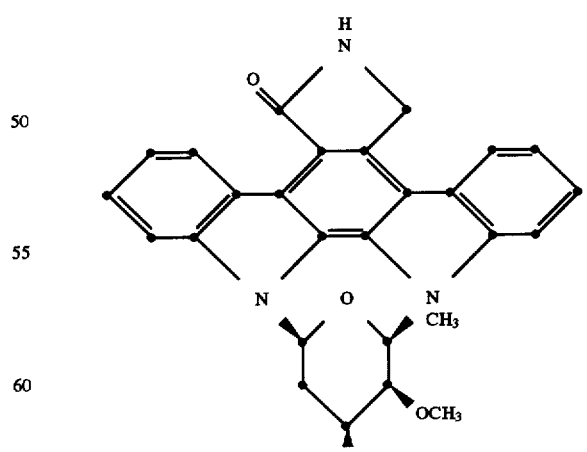

and W represents a bis(carbamyl) or bis(thiocarbamyl) radical,

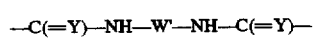
—C(=Y)—NH—W'—NH—C(=Y)— in which W' is a hydrocarbylene radical of 2–20 carbon atoms and Y is O or S. W' is preferably an alkylene radical of 2–10 carbons, unsubstituted, or substituted with 1–3 alkyl groups of 1–3 carbons; an arylene radical of 6–12 carbons, unsubstituted, or substituted with 1–3 alkyl groups of 1–3 carbons, chlorine or bromine. W' is especially preferably hexamethylene and 1,4-phenylene. Y is preferably O.

Compounds of formula (I) can be prepared by procedures known in the art for preparation of carbamates and thiocarbamates. Preferably, the compounds are prepared by reaction of a bis-diisocyanate or a bis-diisothiocyanate with staurosporine to give a compound of formula (I) wherein Y=O or Y=S respectively.

Intermediate bis-diisocyanates and bis-diisothiocyanates suitable for use include:
1,6-diisocyanatohexane
toluene-2,6-diisocyanate
benzene-1,2-diisocyanate
2-methyl-1,5-diisocyanatopentane
naphthalene-2,6 diisocyanate
1,6-diisothiocyanatohexane
1,4-diisothiocyanatobutane
toluene-2,4-diisocyanate
benzene-1,4-diisocyanate
1,2-diisocyanatoethane
naphthalene-1,5-diisocyanate
1,5-diisocyanatopentane
benzene-1,4-diisothiocyanate
2-methyl-1,5-diisothiocyanatopentane For reviews of the preparation of isocyanates and isothiocyanates, see Richter and Ulrich, pp. 619–818, in *The Chemistry of Cyanates and Their Thio Derivatives*, Part 2, (Patai, ed.) Wiley, New York, 1977. The compounds are preferably prepared by reaction of phosgene (Y=O) or thiophosgene (Y=S) with the corresponding diamine. Alternative methods of preparation may also be employed. For example, 1,2-diisocyanatoethane may be prepared by reaction of ethylene urea with phosgene followed by heating.

K-252a Derivatives

The present invention is also directed to the use of specific functional derivatives of K-252a, as therapeutics in certain neurological diseases or disturbances characterized by neurons which are injured, compromised, undergoing axonal degeneration, or at risk of dying. The functional derivatives may be administered alone or in conjunction with a neurotrophic factor (preferably a member of the neurotrophin family, most preferably nerve growth factor, NGF).

A "functional derivative" of K-252a is defined as a modified form of that molecule, which possesses the desired biological activity, herein defined as neuroprotective activity, for example the ability to promote nerve cell survival, or to promote nerve fiber (e.g. axonal) growth, or to enhance cholinergic nerve cell function, or to enhance the function of sensory cells, e.g., dorsal root ganglion nerve cells, or to enhance the function and/or survival of striatal neurons, or to enhance the function and/or survival of basal forebrain neurons. Such molecular modifications may improve the molecule's solubility, absorption, transport (e.g., through the blood-brain barrier and cellular membranes), biological halflife, etc. Alternatively, or in addition, some moieties may decrease the toxicity of the molecule, or eliminate or attenuate any undesirable side effect of the molecule.

The compounds within the scope of the invention may be represented by formula (II) [hereinafter referred to as compound (II)], formula (III) [hereinafter referred to as compound (III)], formula (IV) [hereinafter referred to as compound (IV)], formula (V) [hereinafter referred to as compound (V)], and formula (VI) [hereinafter referred to as compound (VI)], below:

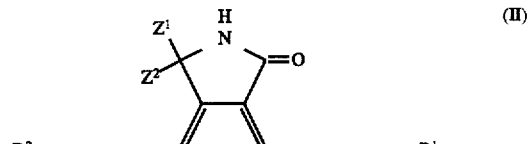

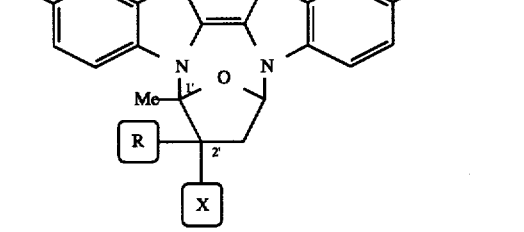

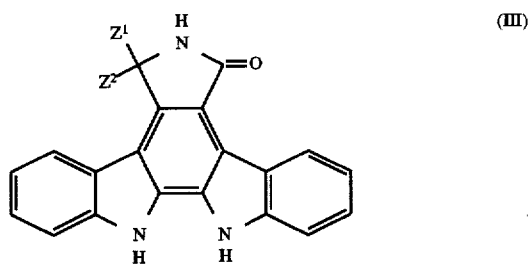

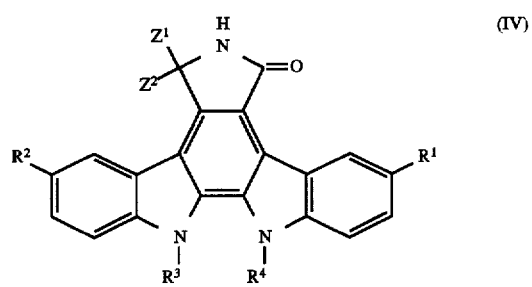

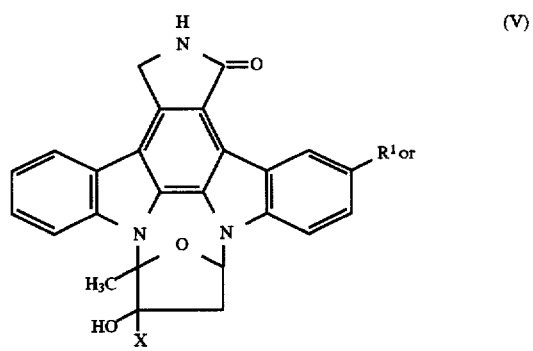

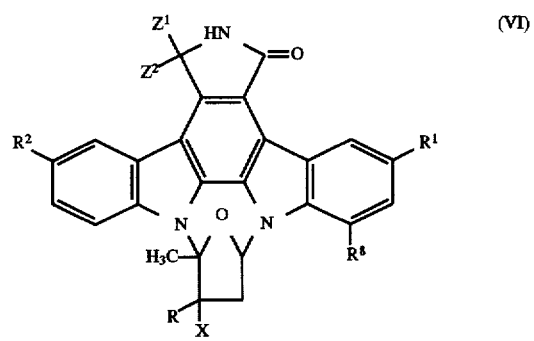

with substitutions in Table 5, below. The functional derivatives of K-252a of the invention may be prepared de novo by chemical synthesis using methods known to those skilled in the art. For example, procedures used for preparation of Compound II are described by Murakata et al (U.S. Pat. No. 4,923,986), hereby incorporated by reference. Procedures used for preparation of Compound III are described by Moody et al., *J. Org. Chem.* 57: 2105–2114 (1992); Steglich et al., *Angew. Chem. Int. Ed. Engl.* 19: 459–460 (1980); Nakanishi et al., *J. Antibiotics* 39: 1066–1071 (1986); and Japanese Patent Application No. 60-295172 (1985). Further methods are described for compounds II-1, 9, 12 and 15 in Japanese Patent Application No. 60-295173 (1985); compounds II-2, 3, 4, 24, 25 and 26 in Japanese Patent Application No. 62-327858 (1987); compounds II-20 in Japanese Patent Application No. 62-327859 (1987); and compounds II-10 in Japanese Patent Application No. 60-257652 (1985) by Meiji Seika Kaisha Ltd.

TABLE 5

Functional Derivatives of K-252a[12]

| Compound | $R^1$ | $R^2$ | X | R | $Z^{1(1)}$ / $Z^2$ |
|---|---|---|---|---|---|
| II-1 | H | H | $CH_2N_3$ | OH | H |
| II-2 | $NHCONHC_6H_5$ | H | $CO_2CH_3$ | OH | H |
| II-3 | $CH_2SOC_2H_5$ | H | $CO_2CH_3$ | OH | H |
| II-4 | H | H | $CH_2OH$ | $OCH_3$ | H |
| II-5 | H | H | $CONHC_2H_5$ | OH | H |
| II-6 | H | H | $CH=NNH-\text{(imidazoline)}$ | OH | H |
| II-7[2,7] | H | H | $CH_2NH-Gly$ | OH | H |
| II-8 | H | H | $CON(CH_3)_2$ | OH | H |
| II-9[3] | H | H | $-CH_2NHCO_2-$ | | H |
| II-10 | Br | H | $CO_2CH_3$ | OH | H |
| II-11 | H | H | $CONH_2$ | OH | H |
| II-12 | H | H | $CH_2OH$ | OH | H |
| II-13 | H | H | $CONHC_3H_7$ | OH | H |
| II-14[2] | H | H | $CH_2NH-Ser$ | OH | H |
| II-15 | H | H | $CH_2SOCH_3$ | OH | H |
| II-16 | H | H | $CH=NOH$ | OH | H |
| II-17 | H | H | $CON\text{(morpholino)}$ | OH | H |
| II-18[2,7] | H | H | $CH_2NH-Pro$ | OH | H |
| II-19 | H | H | $CH=NNHC(=NH)NH_2$ | OH | H |
| II-20 | Br | Br | $CO_2CH_3$ | OH | O |
| II-21 | H | H | $CONH(CH_2)_2OH$ | | OHH |
| II-22 | H | H | $CO_2CH_3$ | OH | O |
| II-23 | H | H | H | OH | H |
| II-24 | H | H | $CH=NNHCONH_2$ | | OHH |
| II-25 | H | H | $CH_2OCOCH_3$ | OH | H |
| II-26[3] | H | H | $-CH_2OC(CH_3)_2O-$ | | H |
| II-29 | $NHCONHC_2H_5$ | H | $CO_2CH_3$ | OH | H |
| II-30 | $CH_2SC_2H_5$ | H | $CO_2CH_3$ | OH | H |
| II-31 | Br | H | $CH_2OH$ | OH | H |
| II-32 | Br | Br | $CO_2CH_3$ | OH | H |
| II-33 | $CH_2SC_6H_5$ | H | $CO_2CH_3$ | OH | H |
| II-34 | Cl | Cl | $CO_2CH_3$ | OH | H |
| II-36 | H | H | $CONHC_6H_5$ | OH | H |
| II-37 | H | H | $CH_2SO-\text{(pyridyl)}$ | OH | H |
| II-38 | H | H | $CH_2NHCO_2C_6H_5$ | | OH H |
| II-39 | $NHCONHC_2H_5$ | $NHCONHC_2H_5$ | $CO_2CH_3$ | OH | H |
| II-40 | $N(CH_3)_2$ | H | $CO_2CH_3$ | OH | H |
| II-41 | $CH_3$ | H | $CO_2CH_3$ | OH | H |
| II-42 | $CH_2OCONHC_2H_5$ | H | $CO_2CH_3$ | OH | H |
| II-43 | $NHCO_2CH_3$ | H | $CO_2CH_3$ | OH | H |
| II-44 | Br | Br | $CH_2OH$ | OH | H |
| II-45 | Br | Br | $CONHC_6H_5$ | OH | H |
| II-46 | Br | Br | $CONHCH_2CH_2OH$ | | OH H |
| II-47 | $CH_2OC_2H_5$ | H | $CO_2CH_3$ | OH | H |
| II-48 | $CH_2N(CH_3)_2$ | H | $CO_2CH_3$ | OH | H |

TABLE 5-continued

Functional Derivatives of K-252a[(12)]

| Compound | R[1] | R[2] | X | R | Z[1(1)] Z[2] |
|---|---|---|---|---|---|
| II-49 | $CH_2SO_2C_2H_5$ | H | $CO_2CH_3$ | OH | H |
| II-50 | $CH_2S$-(2-pyridyl) | H | $CO_2CH_3$ | OH | H |
| II-51 | $CH_2SC_2H_5$ | $CH_2SC_2H_5$ | $CO_2CH_3$ | OH | H |
| II-52 | CH=NNH-(4,5-dihydroimidazol-2-yl) | H | $CO_2CH_3$ | OH | H |
| II-53 | $CH_3S$-(pyrimidin-2-yl) | H | $CO_2CH_3$ | OH | H |
| II-54 | $CH_2S(O)$-(pyrimidin-2-yl) | H | $CO_2CH_3$ | OH | H |
| II-55 | $CH_2S(O)$-(2-pyridyl) | H | $CO_2CH_3$ | OH | H |
| II-56 | $CH_2SC_2H_5$ | $CH_2OH$ | $CO_2CH_3$ | OH | H |
| II-57 | H | H | $CH_2NHCO_2CH_3$ | OH | H |
| II-58 | Br | H | $CONH_2$ | OH | H |
| II-59 | H | H | $CH_2SC_6H_5$ | OH | H |
| II-60 | H | H | $CH_2S$-(2-pyridyl) | OH | H |
| II-61 | H | H | $CH_2SOC_6H_5$ | OH | H |
| II-62 | H | H | $CO_2$n-hexyl | OH | H |
| II-63 | OH | H | $CO_2CH_3$ | OH | H |
| II-64 | O n-propyl | H | $CO_2CH_3$ | OH | H |
| II-65 | $CH_2SCH_2CH_2N(CH_3)_2$ | H | $CO_2CH_3$ | OH | H |
| II-66 | H | H | $CH_2NH_2$ | OH | H |
| II-67 | H | H | $CONHCH_3$ | OH | H |
| II-68 | $CH_2S$-(benzimidazol-2-yl) | H | $CO_2CH_3$ | OH | H |
| II-69 | $CH_2SCH_2$-(furan-2-yl) | H | $CO_2CH_3$ | OH | H |
| II-70 | CH=N-N(pyrrolidin-1-yl) | H | $CO_2CH_3$ | OH | H |
| II-71 | CH=NNH-(2-pyridyl) | H | $CO_2CH_3$ | OH | H |
| II-72 | $CH_2S(CH_2)_2NH_2$ | H | $CO_2CH_3$ | OH | H |

TABLE 5-continued

Functional Derivatives of K-252a[12]

| Compound | $R^1$ | $R^2$ | X | R | $Z^{1(1)}$ $Z^2$ |
|---|---|---|---|---|---|
| II-73 | CH₃S-⟨triazole ring with N=, N, NH⟩ | H | $CO_2CH_3$ | OH | H |
| II-74 | $CH=NNH-C(=NH)NH_2$ | H | $CO_2CH_3$ | OH | H |
| II-75 | $CH=N-N$⟨tetrazole⟩ | H | $CO_2CH_3$ | OH | H |
| II-76 | $CH=N-N$⟨morpholine⟩ | H | $CO_2CH_3$ | OH | H |
| II-77 | $CH=N-N(CH_3)_2$ | H | $CO_2CH_3$ | OH | H |
| II-78 | $CH=N-N$⟨piperazine⟩$NCH_3$ | H | $CO_2CH_3$ | OH | H |
| II-79 | $CH_2S(CH_2)_2NH-n-C_4H_9$ | H | $CO_2CH_3$ | OH | H |
| II-80 | $CH_2S-(CH_2)_2N(CH_3)_2$ | $CH_2S(CH_2)_2-N(CH_3)_2$ | $CO_2CH_3$ | OH | H |
| II-81 | $CH_2SCH(CH_3)_2$ | $CH_2SCH(CH_3)_2$ | $CO_2CH_3$ | OH | H |
| II-82 | $CH_2S(CH_2)_2CH_3$ | $CH_2S(CH_2)_2CH_3$ | $CO_2CH_3$ | OH | H |
| II-83 | $CH_2S(CH_2)_3CH_3$ | $CH_2S(CH_2)_3CH_3$ | $CO_2CH_3$ | OH | H |
| II-84 | $CH_2OCH_3$ | $CH_2OCH_3$ | $CO_2CH_3$ | OH | H |
| II-85 | $CH_2OC_2H_5$ | $CH_2OC_2H_5$ | $CO_2CH_3$ | OH | H |
| II-86 | $CH_2OH$ | $NHCONHC_2H_5$ | $CO_2CH_3$ | OH | H |
| II-87 | $CH_2SC_2H_5$ | $NHCONHC_2H_5$ | $CO_2CH_3$ | OH | H |
| II-88 | $CH_3$ | $CH_3$ | $CO_2CH_3$ | OH | H |
| II-89 | $CH_2SC_2H_5$ | $CH_2S(O)C_2H_5$ | $CO_2CH_3$ | OH | H |
| II-90 | $CH_2OH$ | $CH_2OH$ | $CH_2OH$ | OH | H |
| II-91 | $CH(-SCH_2CH_2S-)$ | $NO_2$ | $CO_2CH_3$ | OH | H |
| II-92 | $CH(-SCH_2CH_2S-)$ | $NHCONHC_2H_5$ | $CO_2CH_3$ | OH | H |
| III-1 | — | — | — | — | H |
| III-2 | — | — | — | — | O |
| IV-1[4,9] | H | H | — | — | H |
| IV-2[5] | Br | H | — | — | H |
| IV-3[6] | H | H | — | — | H |
| IV-4[8,9] | H | H | — | — | H |
| IV-5[10] | H | H | — | — | H |
| IV-6[7,11] | H | H | — | — | H |
| VI-1[13] | H | H | $CO_2CH_3$ | OH | H |
| VI-2[14] | H | $NH_2$ | $CO_2CH_3$ | OH | H |

[1]$Z^1$ and $Z^2$ are both hydrogen, or both are combined together to represent oxygen, where indicated.
[2]NH-amino acid linkage is an amide bond through the carboxyl group of the amino acid.
[3]X and R are combined together to form the linking group.
[4]$R^3$ is $CH_2CH=CH_2$; $R^4$ is H.
[5]$R^3$ and $R^4$ are each H.
[6]$R^3$ and $R^4$ are each $CH_2CH=CH_2$.
[7]Compound is in the form of the hydrochloride.
[8]$R^3$ is H and $R^4$ is $CH_2CH=CH_2$.
[9]IV-1 and IV-4 are a 1.5 to 1.0 mixture of the two components.
[10]$R^3 = R^4 = CH_2CH_2CH_2OH$
[11]$R^3 = CH_2CH_2CH_2-N$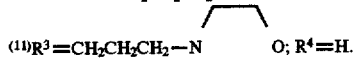$O$; $R^4 = H$.
[12]For K-252a itself, $R^1 = R^2 = H$, $X = CO_2CH_3$, $R = OH$, and $Z^1$ and $Z^2$ are each H.
(13) $R^8 = NHCONHC_2H_5$.
(14) $R^8 = NH_2$.

The invention also involves a method for enhancing the function of cholinergic neurons, by administration of a therapeutic amount of K-252a, represented by the formula (II) given above and substitutions shown in Table 5 (note 12). This compound is prepared by procedures described in the art (see Matsuda et al., U.S. Pat. No. 4,554,402; Kase et al., J. Antibiotics 37:1059–1065, 1986).

By "enhancing the function of cholinergic neurons" is meant promoting cholinergic nerve cell survival, and/or nerve fiber (e.g. axonal) growth, and/or enhancing cholinergic function of nerve cells. K-252a may be administered with or without a trophic factor, preferably a member of the neurotrophin family, most preferably nerve growth factor (NGF).

Uses of the Compounds

As described more fully below, the present invention provides novel uses of functional derivatives of K-252a or compounds of Formula I, either alone or in combination with neurotrophic factors such as NGF, as therapeutics for neurological diseases, especially those diseases characterized either by neuronal cells which are injured, compromised, undergoing axonal degeneration, or at increased risk of dying, or by impaired cholinergic activity. These diseases include those induced by excitatory amino acids. The bioactivity of the compounds of the invention, including the combination with a neurotrophic factor, may conveniently be assayed by a cultured PC-12 cell ornithine decarboxylase assay, a cultured spinal cord or basal forebrain choline acetyltransferase assay, a cultured dorsal root ganglion neuron survival assay, a cultured striatal neuron survival assay, a cultured basal forebrain neuron survival assay, an in ovo model of developmentally programmed motoneuron death, an in vivo adult hypoglossal axotomy model, or an in vivo excitotoxin neuroprotection assay, e.g., a excitotoxic lesioning of the nucleus basalis. These assays are all described in detail below. Thus, the compounds of this invention are useful for administration to humans or other mammals who suffer from neurological diseases or disturbances characterized by increased risk of neuronal cell death or dysfunction. These neurological diseases and disturbances include but are not limited to: Alzheimer's disease; motor neuron disease including amyotrophic lateral sclerosis; Parkinson's disease; stroke or other ischemic injuries; Huntington's disease; AIDS dementia; epilepsy; concussive or penetrating injuries of the brain or spinal cord; and peripheral neuropathies.

The compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; for oral administration, particularly in the form of tablets or capsules; or intranasally, particularly in the form of powders, nasal drops, or aerosols.

The composition may conveniently be administered in unit dosage form and may be prepared by any of the methods well known in the pharmaceutical art, for example, as described in Remington's Pharmaceutical Sciences (Mack Pub. Co, Easton, Pa., 1980). Formulations for parenteral administration may contain as common excipients sterile water or saline, polyalkylene glycols such as polyethylene glycol, oils of vegetable origin, hydrogenated naphthalenes and the like. In particular, biocompatable, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials of this invention can be employed as the sole active agent in a pharmaceutical or can be used in combination with other active ingredients, e.g., other growth factors which could facilitate neuronal survival or axonal growth in neurological diseases or disorders, for example, peripheral neuropathy.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the neurological disease, the overall health status of the particular patient, the relative biological efficacy of the compound selected, the formulation of the compound excipients, and its route of administration.

The present invention will be further illustrated by the following examples. These examples are not to be construed as limiting the scope of the invention, which is to be determined solely by the appended claims.

EXAMPLE 1

1,6-Hexamethylene-bis-(carbamylstaurosporine) (HBCS)

A solution of 1.0 mg (2.15 micromoles) of staurosporine (Kamiya Biomedical Company, Thousand Oaks, Calif.) in 1.00 ml of ethyl acetate (dried over anhydrous magnesium sulfate) was treated with 17 microliters (1.08 micromoles) of a solution of 10.75 mg of hexamethylene-bis-isocyanate in 1.0 ml of dried ethyl acetate. The reaction mixture in an amber glass reaction vial was allowed to stand at room temperature for two days. A crystalline deposit weighing 600 micrograms was separated. Its composition was verified as HBCS by fast atom bombardment mass spectroscopy (FAB-MS).

$M + H^+$ Calculated = 1102    $M + Na^+$ Calculated = 1124
Found = 1102    Found = 1124

This product and all of the subsequently described staurosporine derivatives were stored in non-actinic glass vials.

EXAMPLE 2 p-Phenylene-bis-(carbamylstaurosporine) (PBCS)

A solution of 1.0 mg of staurosporine (2.15 micromoles) in 1.00 ml of dried ethyl acetate was treated with 45 microliters (1.08 micromoles) of a solution prepared from 3.83 mg of p-phenylene diisocyanate (Trans World Chemicals P1586-1) in 1.00 ml of dried ethyl acetate. The reaction mixture was allowed to stand overnight. A white precipitate deposited. Then 0.5 ml of petroleum ether was added. The mixture was filtered into a vacuum-dried sintered-glass funnel. A total of 0.90 mg of crystalline product was collected and was identified as p-phenylene-bis-(carbamylstaurosporine) by fast atom bombardment mass spectroscopy.

M+H$^+$ Calculated=1093 Found=1093

Preparation A

N-Phenylcarbamylstaurosporine (PCS)

Reference: U.S. Pat. No. 5,093,330

A solution of 2.0 mg of staurosporine (4.30 micromoles) in 1.50 ml of dried ethyl acetate was treated with 468 μl (4.30 micromoles) of a solution of 10 μl of phenyl isocyanate in 0.990 ml of dried ethyl acetate. The solution was allowed to stand overnight and 3 ml of hexane was added in portions. Colorless crystals were obtained which weighed 2.39 mg. After recrystallizing this product from 1 ml of ethyl acetate and 2 ml of petroleum ether, 1.75 mg of a crystalline product was isolated. From a similar preparation, the product's composition as N-phenylcarbamylstaurosporine was verified by FAB-MS.

M+H$^+$ Calculated=586 Found=586

Preparation B

N-Phenylthiocarbamylstaurosporine (PTCS)

A solution of 1.0 mg (2.15 micromoles) of staurosporine in 1.00 ml of ethyl acetate was treated with 26 microliters of a stock solution of 10 microliters of phenyl isothiocyanate in 1.00 ml of ethyl acetate. This aliquot contained 290 micrograms (2.15 micromoles) of phenyl isothiocyanate. The reaction mixture was held at 25° C. overnight, and then 2.0 ml of hexane was added. The resulting crystalline product was filtered off, washed with hexane and dried with a stream of argon gas.

FAB-MS Calc: M+H$^+$=602 Found=602

Preparation C

N-Ethylcarbamylstaurosporine (ECS)

A solution of 0.9 mg (1.93 micromoles) of staurosporine in 900 microliters of ethyl acetate was treated with 1.93 micromoles (30.2 microliters of a stock solution of 9.05 mg of ethyl isocyanate in 2.00 ml of dried ethyl acetate) of ethyl isocyanate. The reaction mixture was held at 25° C. overnight, and 2.0 ml of hexane was added. The crystalline product was separated and dried.

FAB-MS Calc.: M+H$^+$ = 538    M+Na$^+$= 560
Found            = 538           = 560

EXAMPLE 3

Compound II-4

Compound A (962 mg, 2 mmol) was dissolved in a mixture of 30 ml of tetrahydrofuran and 10 ml of methanol, and then 760 mg of sodium borohydride (20 mmol) was added thereto under ice cooling, followed by stirring at the same temperature for 4 hours and further at room temperature for 12 hours. After 3N hydrochloric acid was added thereto, the solution was washed with an aqueous solution of sodium chloride and dried over magnesium sulfate, followed by evaporation of the solvent. The residue was purified by silica gel column chromatography (chloroform/methanol= 98/2) to give 882 mg (yield 97%) of Compound II-4.

Melting Point: 130°–140° C.

$^1$H-NMR (DMSO-d$_6$) δ (ppm): 2.032(1H, dd, J=5.0, 13.9 Hz), 2.231 (3H, s), 2.967(3H, s), 3.609(1H, dd, J=7.6, 13.4 Hz), 3.959(2H, m), 5.000(2H, s), 5.268(1H, t, J=5.3 Hz), 7.065(1H, dd, J=4.9, 7.3 Hz), 7.254–8.038 (7H, m), 8.565 (1H, s), 9.206(1H, d, J=7.8 Hz)

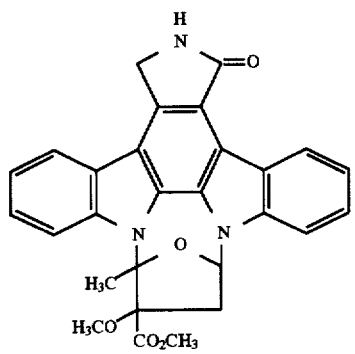

Compound A

EXAMPLE 4

Compound II-14

Compound B (393 mg, 0.9 mmol) was dissolved in 25 ml of tetrahydrofuran, and then 3 ml of tetrahydrofuran containing 309 mg of carbobenzoxy-L-serine (1.35 mmol), 156 mg of N-hydroxysuccinimide (1.35 mmol), 0.1 ml of 4-methylmorpholine (0.9 mmol) and 279 mg of dicyclohexylcarbodiimide (1.35 mmol) was added under ice cooling, followed by stirring for 12 hours. The reaction mixture was filtered and the solvent was evaporated. The residue was purified by silica gel column chromatography (chloroform/methanol=99/1) to give 429 mg (yield 72%) of Compound C.

Melting Point: 188°–193° C.

SIMS (m/z): 660 (M+1)$^+$

Compound C (399 mg) was dissolved in 10 ml of dimethylformamide, and then 300 mg of 10% palladium on carbon was added, followed by stirring at 50° C. for 7 hours in a hydrogen stream. The reaction mixture was filtered through Celite and the solvent was evaporated. The residue was purified by silica gel column chromatography (chloroform/methanol/28% ammonium hydroxide=90/10/1) and the obtained product was dissolved in 5 ml of tetrahydrofuran, followed by addition of 5 ml of 1.7N hydrogen chloride/ethyl acetate and 10 ml of diethyl ether. The precipitate was separated from the solution by filtration to give 234 mg (yield 69%) of Compound II-14.

Melting Point: >300° C.

$^1$H-NMR (DMSO-d$_6$+D$_2$O) δ (ppm): 1.92–2.28(1H, m), 2.20 (3H, s), 2.84–3.12(7H, m), 3.40–4.20(5H, m), 5.04 (2H, s), 6.98(1H, m), 7.24–8.20(7H, m), 8.76(1H, brs), 9.22(1H, d, J=8 Hz)

SIMS (m/z): 527 (M+2)$^+$

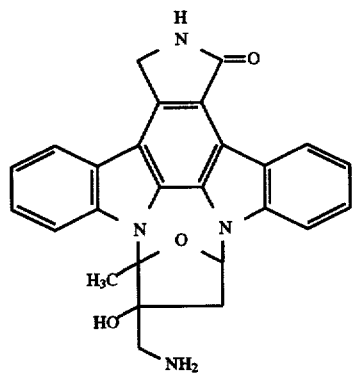

Compound B

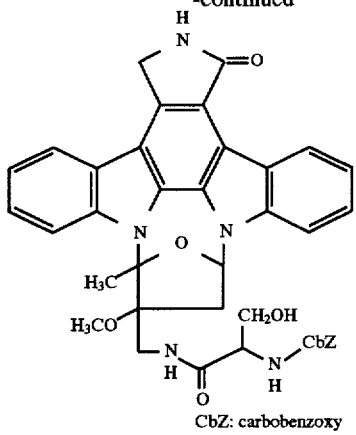

Compound C

CbZ: carbobenzoxy

EXAMPLE 5

PC-12 cells are a clonal population arising from a tumor of rat adrenal medulla, and have proven to be an extremely useful and widely studied model for study of the actions of NGF (Guroff, *Cell Culture in the Neurosciences*, Plenum Publishing Corporation, pages 245–272, 1985). One particularly robust effect of NGF on these cells is a rapid stimulation of the activity of ornithine decarboxylase (ODC), an effect which was reported to be blocked by 200 nM K-252a (Koizumi et al., 1988). In the experiments of this Example, PC-12 cells (obtained from Dr. G. Guroff, National Institute of Health, Bethesda, Md.) were cultured in 48-well plates at a density of $6 \times 10^4$ cells/cm$^2$ and incubated with drug vehicle (0.5% DMSO), K-252a, staurosporine, or HBCS. K-252a and staurosporine are commercially available from Kamiya Biomedical. Four hours after drug addition, the cells were harvested for ODC assay, as described by Huff et al. (J. Cell Biol. 88: 189–198, 1981).

All three compounds produced an induction (i.e., an increase) of ODC activity, but there were considerable differences in potency and efficacy (FIG. 1). K-252a produced a dose-dependent induction of ODC activity, with effects detectable at 2 nM and increasing to a maximum at 200 nM (36.3 fold induction). The effects of staurosporine were likewise detectable at 2 nM, but peaked at 20 nM (34.7 fold induction), and declined considerably at 200 nM. HBCS (Example 1) similarly induced at 2 nM, but higher concentrations failed to yield an increased effect, so that the maximum efficacy was much less than that of the other two compounds (6.5 fold induction). In another experiment, the effects of PTCS, PCS, and ECS (Example 2) on PC-12 cell ODC activity were compared to that of K-252a. At 200 nM concentrations, expressing the activity of K-252a as 100%, PTCS exhibited 71.4% of the activity of K-252a, while PCS and ECS exhibited 88.9% and 61.9% of the activity of K-252a, respectively. However, the protein kinase C inhibitor H-7 did not induce ODC activity at 30 µM, a concentration known to inhibit protein kinase C activity (Nakadate et al., Biochem. Pharmacol. 37: 1541–1545, 1988).

Figure 2:
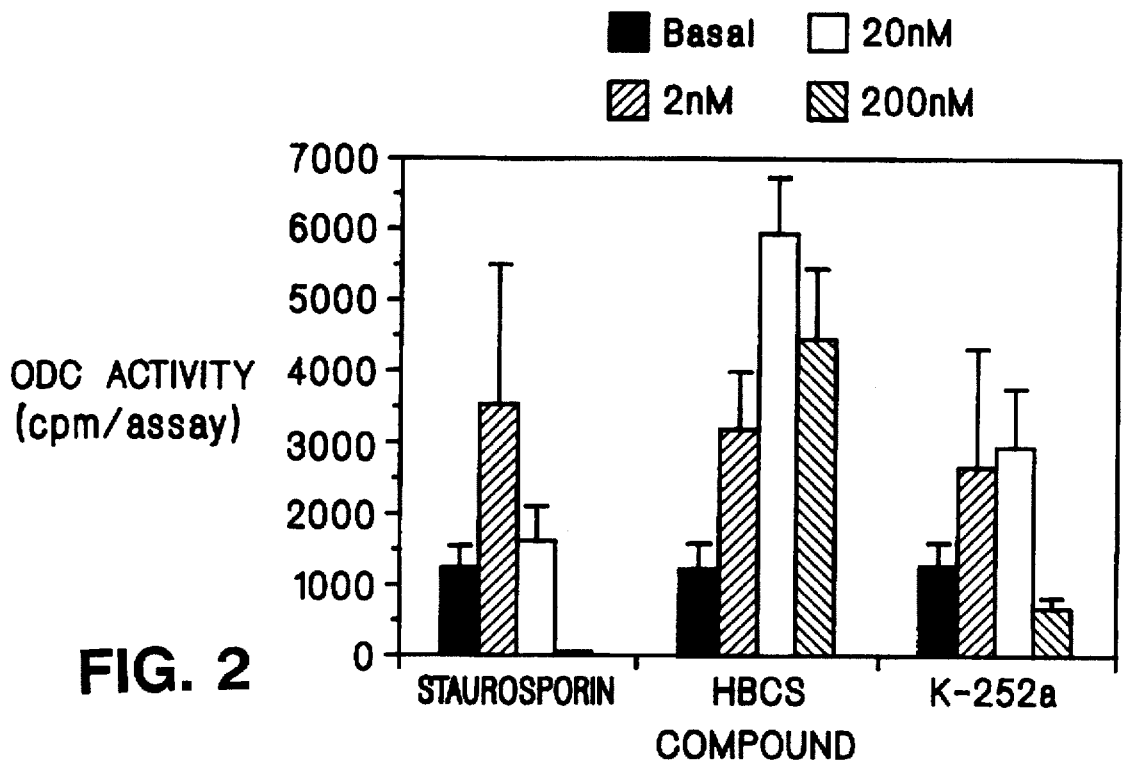
FIG. 2 is a graph illustrating the effects of staurosporine, HBCS, and K-252a on NGF-stimulated ODC activity in PC-12 cells.
Figure 3:
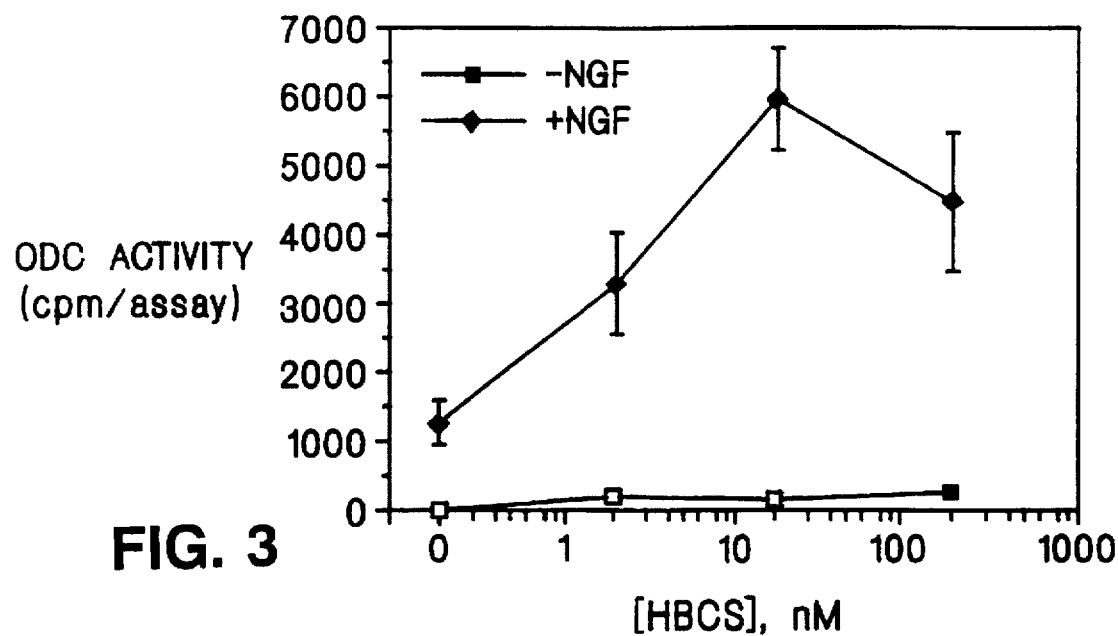
FIG. 3 is a graph illustrating the NGF-potentiating effect of HBCS on ODC activity in PC-12 cells.

The ability of K-252a, staurosporine and HBCS to potentiate and/or inhibit NGF bioactivity was assessed by adding 10 ng NGF per ml of cell culture medium, in the absence or presence of the above compounds in the concentrations previously indicated, followed by ODC assay of the cells as described above (FIG. 2). This concentration of NGF was selected to provide an intermediate level of induction so that either potentiating or inhibiting effects of the compounds could be detected. K-252a at 200 nM inhibited the NGF induction of ODC, as reported by Koizumi et al. (1988), but, surprisingly, potentiated the induction at lower concentrations (2 nM and 20 nM). Staurosporine, at 2 nM, also potentiated the induction by NGF, but this effect was lost at higher concentrations (20 and 200 nM). HBCS, in contrast, potentiated the effects of NGF at all concentrations tested. This striking effect is shown relative to the modest ODC-inducing effects of HBCS alone in FIG. 3.

EXAMPLE 6

The effect of K-252a on choline acetyltransferase (CHAT) activity was assayed in dissociated spinal cord cultures prepared from fetal rats by standard methods (see below). ChAT is the enzyme that catalyzes the synthesis of the neurotransmitter acetylcholine, and is a specific biochemical marker for cholinergic neurons. In the spinal cord, the large majority of cholinergic neurons are motor neurons. Assay of this enzyme may thus be used as an indication of the effects of a factor (or factors) on the survival of cholinergic neurons and/or regulation of this enzyme.

Figure 4:
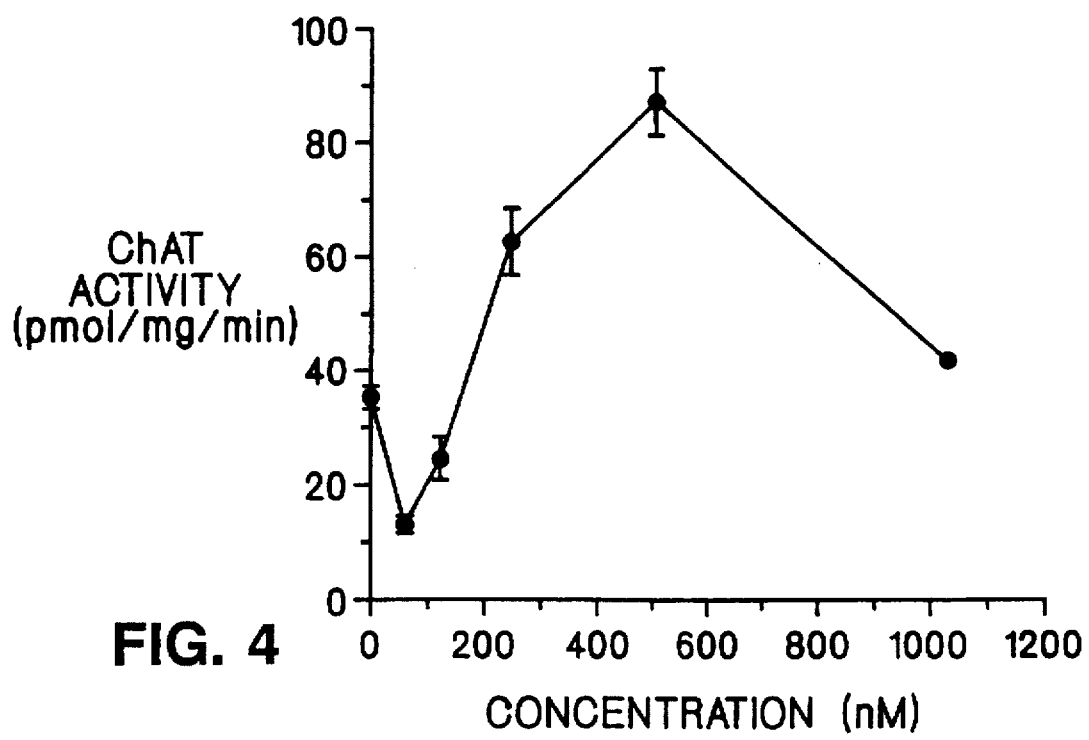
FIG. 4 is a graph illustrating the effect of K-252a on choline acetyltransferase (CHAT) specific activity in rat embryonic spinal cord cultures.
Figure 5:
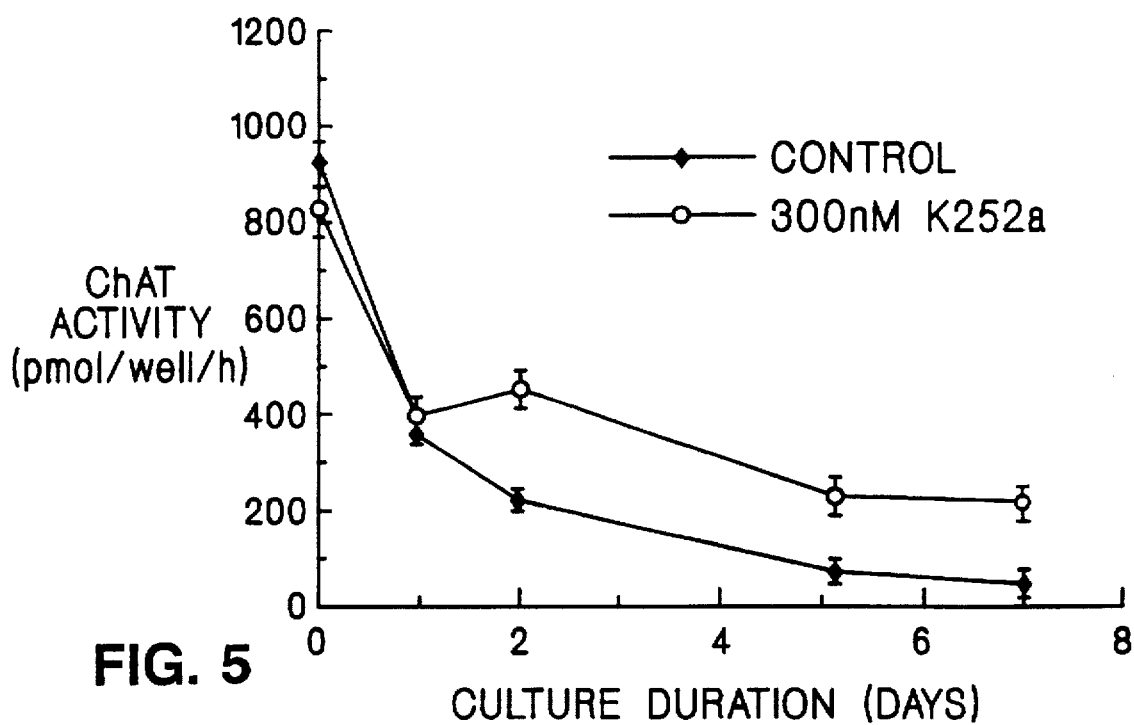
FIG. 5 is a graph illustrating the time course of K-252a effect on ChAT activity in rat embryonic spinal cord cultures.

K-252a was added at the indicated concentrations to the cultures after incubating 2–3 hours after plating to allow cells to attach to the substrate. ChAT activity was measured after 48 hours in culture. K-252a in spinal cord cultures resulted in a dose dependent increase in CHAT activity with maximum efficacy (2- to 3-fold increase) achieved at 200–300 nM (FIG. 4). Higher concentrations resulted in a decrease in ChAT activity (FIG. 4). Longer culture incubation times, up to seven days, resulted in 4-to-5 fold increases in ChAT activity (FIG. 5) due to the decreased basal level of ChAT activity. In this culture system, increasing numbers of motor neurons degenerate and die over time under basal (control) conditions (McManaman et al., *Developmental Biol.* 125:311–320, 1988). The results shown in both FIGS. 4 and 5 are the result of a single application of K-252a on the day of culture initiation, indicating a prolonged effect on the survival of spinal cord cholinergic neurons and/or regulation of the enzyme itself.

Experiments with dissociated cultures of fetal rat spinal cord cells were performed generally as described (Smith et al., *J. Cell Biol.* 101:1608–1621, 1985). Dissociated cells were prepared from spinal cords dissected from day 14 embryonic rats by standard techniques known to those skilled in the art, using trypsin dissociation of tissue (Smith et al., supra). Cells were seeded (plated) at $6 \times 10^5$ cells/cm$^2$ in poly-1-ornithine coated plastic tissue culture wells in serum-free N2 medium and incubated at 37° C. in a humidified atmosphere of 5% $CO_2$/95% air (Bottenstein et al., *Proc. Natl. Acad. Sci. USA* 76:514–517, 1979) for 48 hours. ChAT activity was measured using modifications of the Fonnum procedure (*J. Neurochem.* 24:407–409, 1975) according to Ishida and Deguchi (*J. Neurosci.* 3:1818–1823, 1983), and McManaman et al., supra (1988). Activity was normalized to total protein measured by the bicinchonicic acid/$Cu^{++}$ reaction (BCA protein assay reagent, Pierce, Rockland, Ill.).

EXAMPLE 7

Figure 8:
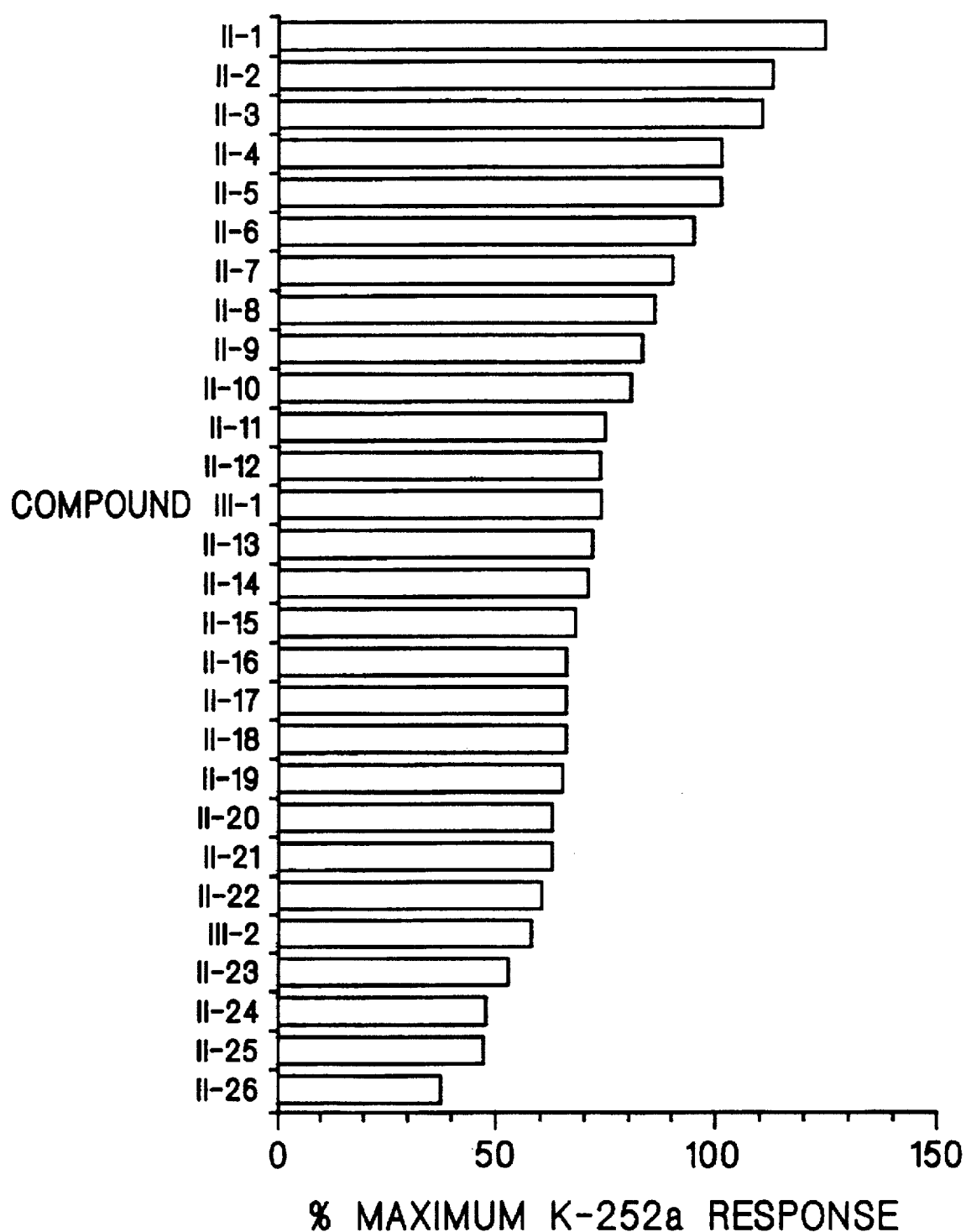
FIG. 8 is a graph illustrating the effect of K-252a functional derivatives on ChAT activity in rat embryonic spinal cord cultures.

Over one hundred functional derivatives of K-252a were tested in the spinal cord CHAT assay to determine their relative efficacy. The data in FIG. 8 show that of the original functional derivatives tested at 300 and 30 nM, 28 resulted in significantly increased ChAT activity at 300 nM. One functional derivative, compound II-21, was also active at 30 nM (30% enhancement of ChAT activity over basal levels). This compound was more potent than K-252a or the remaining analogs since none of these actively enhanced ChAT activity at 30 nM.

FIG. 13a shows the ability of the original 28 K-252a derivatives shown to significantly increase ChAT activity in rat spinal cord cultures, as well as 30 additional derivatives (compounds II-29 through II-34, II-36 through II-56, and IV-1 through IV-3, all inclusive). FIG. 13b shows the ability of K-252a derivatives II-66-80, IV-5, IV-6, VI-1, and VI-2 to significantly increase ChAT activity in rat spinal cord cultures. FIG. 13C shows the ability of 12 additional K252a derivatives to significantly increase ChAT activity in rat spinal cord cultures.

EXAMPLE 8

K-252a as well as over 50 functional derivatives were assessed for their ability to promote dorsal root ganglion neuron cell survival. Cell survival was measured by uptake of calcein AM, an analog of the viable dye, fluorescein diacetate. Calcein is taken up by viable cells and cleaved intracellularly to fluorescent salts which are retained by intact membranes of viable cells. Microscopic counts of viable neurons correlate directly with relative fluorescence values obtained with the fluorimetric viability assay. This method thus provides a reliable and quantitive measurement of cell survival in the total cell population of a given culture (Bozyczko-Coyne et al., *J. Neur. Meth.* 50:205-216, 1993).

Dorsal root ganglia were dissected from embryonic age day 8 chick embryos and dissociated cells prepared by subsequent Dispase (neutral protease, Collaborative Research) dissociation. Neurons were seeded at low density ($1.8\times10^4$ cells/cm$^2$) into 96 well poly-L-ornithine and laminin coated plates. Cells were cultured for 48 hours in serum-free N2 medium (Bottenstein and Sato, 1979) at 37° C. in a humidified atmosphere, 5% $CO_2$/95% air. Cell survival was assessed at 48 hours using the viable fluorimetric assay described above.

Figure 6:
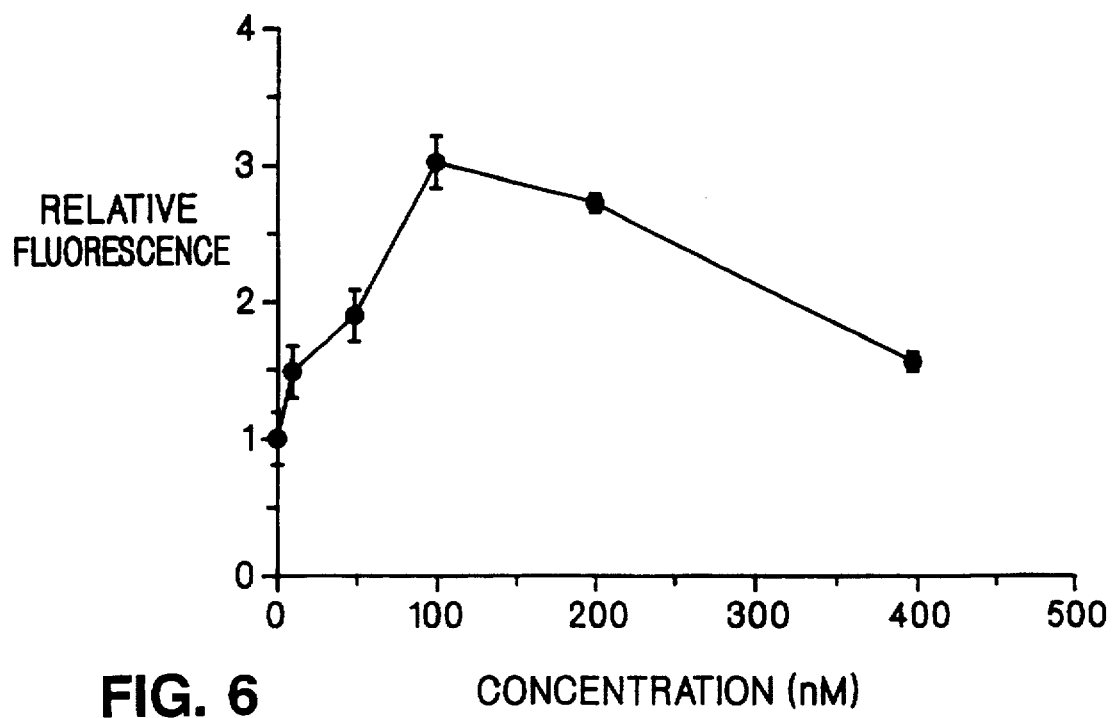
FIG. 6 is a graph illustrating the effect of K-252a on survival of chick embryonic dorsal root ganglion neurons.
Figure 7:
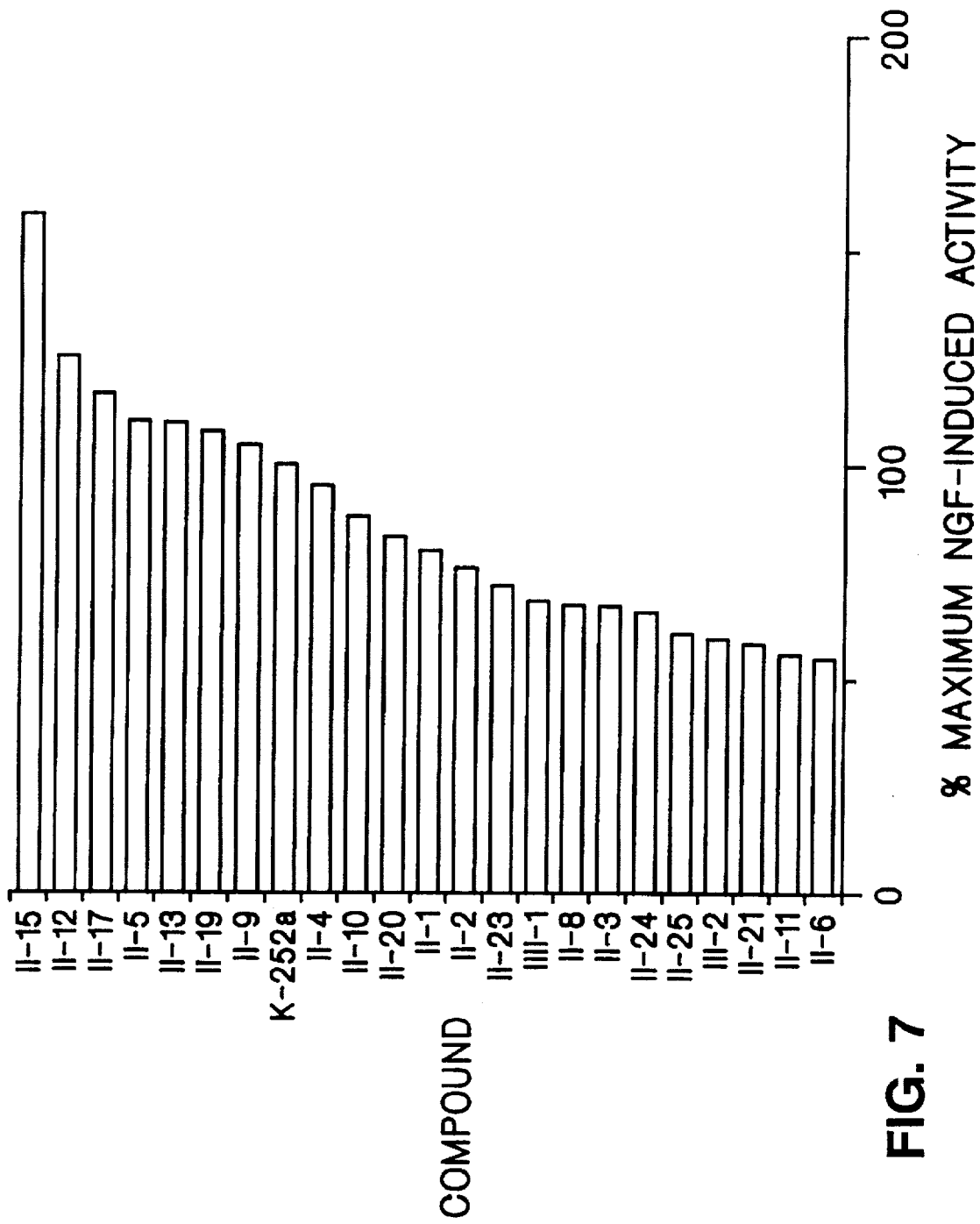
FIG. 7 is a graph illustrating the effect of K-252a functional derivatives on survival of chick embryonic dorsal root ganglion neurons.

Dorsal root ganglion neuron survival was enhanced by K-252a in a concentration-dependent manner. Maximum activity was observed at approximately 100 nM (FIG. 6). Twenty-four of the 50 analogs tested were active in promoting DRG neuron survival, twenty-two of which are shown in FIG. 7. All of these analogs were also active in increasing spinal cord CHAT activity (see Example 5, FIG. 8). The original 22 as well as the 2 additional active analogs (II-30, II-32) are shown in FIG. 14. Microscopic examination of the dorsal root ganglion neurons stimulated with the twenty-four active functional derivatives indicated enhanced nerve fiber outgrowth as well.

EXAMPLE 9

Infusion of the excitatory amino acid kainic acid (kainate) directly into the ventricles of a rodent brain results in neuronal degeneration of the pyramidal cells of the hippocampus. This neuronal death is characterized by a marked increase in the proteolysis of the cytoskeletal protein, spectrin. Spectrin breakdown products can be measured in homogenates of the hippocampus within 24 hours following kainate administration. The magnitude of spectrin proteolysis is highly correlated with the magnitude of neuronal death in pyramidal cells of the hippocampus (Siman et al., *J. Neurosci.* 9:1579-1590, 1989), and thus spectrin proteolysis is an excellent biochemical marker of excitatory amino acid-induced neuronal degeneration. Excessive release of endogenous excitatory amino acids has been implicated as an etiology in numerous neurological diseases and disorders, including stroke and other ischemic injuries; Alzheimer's disease; motor neuron disease including amyotrophic lateral sclerosis; Parkinson's disease; Huntington's disease; AIDS dementia; epilepsy; and concussive or penetrating injuries of the brain or spinal cord.

The results shown in FIGS. 9-12 were generated according to the following methods:

Kainate infusion regime:

The effect of K-252a or its derivatives on kainate-induced neuronal damage was evaluated. Adult male or female Sprague-Dawley rats (175-250 g) were anesthetized with Nembutal (50 mg/kg. ip). Each rat was administered a test compound (in a total of 5 µl) before and after kainate treatment (5 µl) by icv infusion. This was done using a dose and infusion schedule as indicated for individual cases above. Control animals received vehicle instead of kainate and drug infusion. For anatomical studies, icv infusions were delivered through a cannula (Plastic One, Roanoke, Va.) implanted approximately one week before drug infusions, and positioned at stereotaxic coordinates: anterior-posterior at bregma, 1.5 mm lateral to bregma, and 4.4 mm ventral from the top of the skull. Results of this treatment regimen were evaluated two weeks later using the anatomical analysis described below.

In studies to assess the effect of K-252a or its derivatives on kainate-induced spectrin proteolysis, anesthetized rats received a 5 µl icv infusion of the drug, or vehicle, simultaneously with kainate, through a 10 µl Hamilton syringe positioned at the stereotaxic coordinates described above. These rats were killed 24 hours later and subjected to biochemical analysis as described below.

Anatomical and Biochemical Analyses:

Anatomical analysis was performed as follows. Rats were killed by decapitation 2 weeks following treatments, and the brains were rapidly removed and frozen on dry ice. A series of slide-mounted coronal sections from each brain was stained with thionin and examined microscopically. Damage to the hippocampus was quantified by summing the total number of 4 anatomically defined regions of the hippocampus (CA1-4 according to the classification of Lorente de No, as described by Shepard, 1979, *The Synaptic Organization of the Brain*, Oxford, p. 310, hereby incorporated by reference), on both left and right sides of the brain, that suffered a loss of pyramidal cells.

Biochemical analysis was performed as follows: Calpain I-sensitive proteolysis of brain spectrin (fodrin) was evaluated in homogenates of the hippocampus using an immunoblot analysis described by Siman et al. (1988, Neuron, 1: 279-287, hereby incorporated by reference). Briefly, rats were killed by decapitation 24 hours following treatment, and the dorsal hippocampus was rapidly dissected out of the brain and homogenized in 20 mM Tris-HCl (pH 7.4) containing 0.1 mM phenylmethylsulfonyl fluoride. Proteins from aliquots of each homogenate were separated by SDS-PAGE, and an immunoblot analysis was used to quantitate the amount of kainate-induced spectrin breakdown in each sample.

Figure 9:
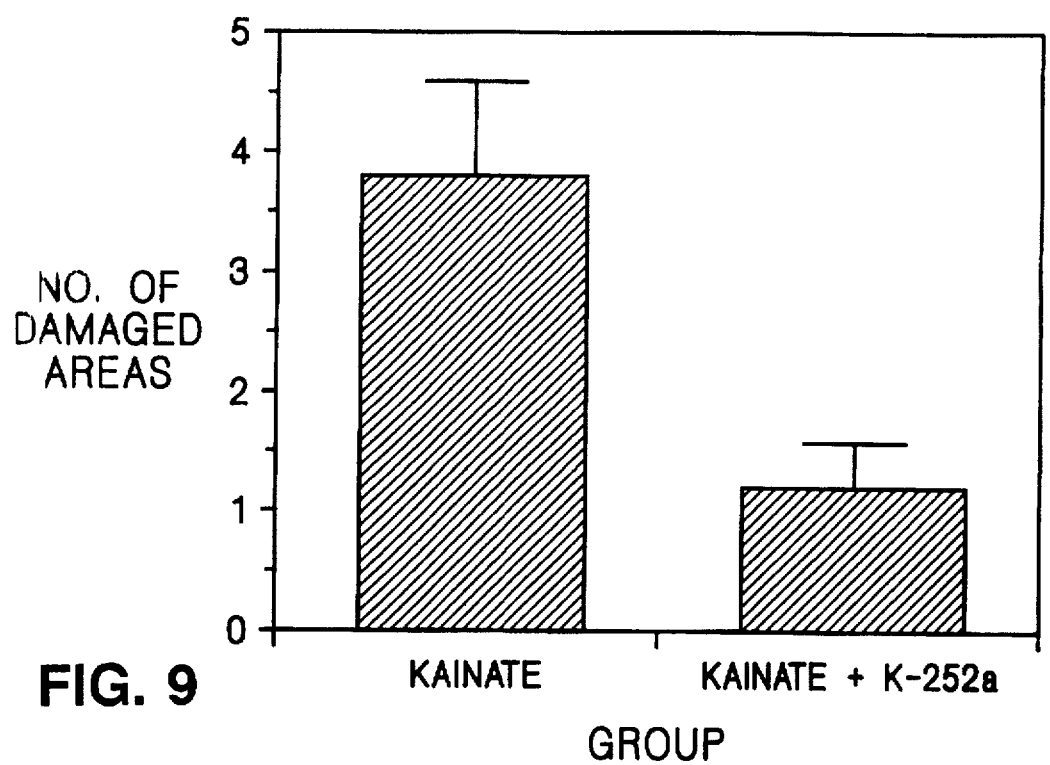
FIG. 9 is a graph illustrating the effect of K-252a on kainate-induced damage to the rat hippocampus.

FIG. 9 shows the effect of K-252a on kainate-induced neuronal degeneration in the hippocampus. Cannulated male and female Sprague-Dawley rats received 0.4 µg of K-252a, or vehicle, 30 minutes prior to and about 3 and 24 hours following kainate (0.6 µg) injection directly into the lateral cerebral ventricles of the brain (icv). Two weeks later the brains were excised, frozen, sectioned, and stained for histological analysis, as described below. Data shown are the mean number of sub-regions of the hippocampus damaged for each group, ±Standard Error of the Means (S.E.M.). K-252a significantly reduced the number of damaged areas within the hippocampus from 3.86±0.78 (in the absence of K-252a) to 1.18±0.4 (in the presence of K-252a).

Figure 10:
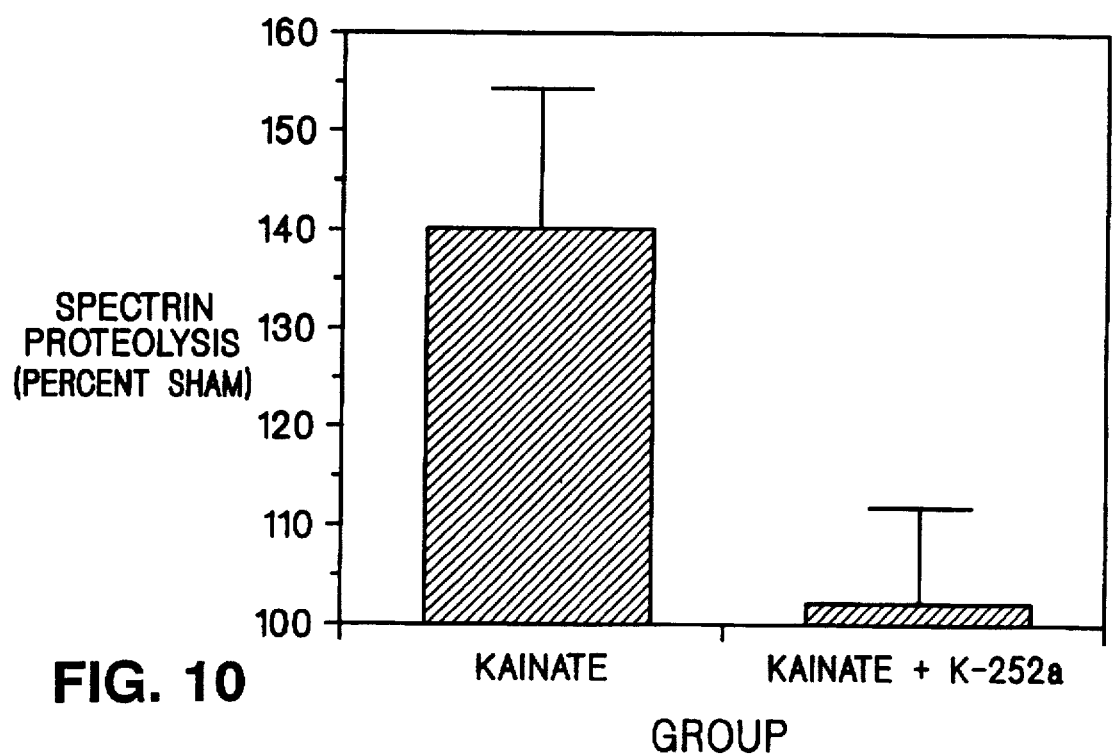
FIG. 10 is a graph illustrating the effect of K-252a on kainate-induced spectrin proteolysis in the rat hippocampus.

FIG. 10 shows the effect of K-252a on kainate-induced spectrin breakdown in the hippocampus. Female Sprague-Dawley rats received 0.4 μg of K-252a, or vehicle, together with a neurotoxic dose of kainate (0.6 μg), by icv infusion. Sham control animals received infusions of vehicle, but no kainate or K-252a. Twenty-four hours later, homogenates of the dorsal hippocampus were analyzed for spectrin breakdown products as described below. The magnitude of spectrin proteolysis is expressed as a percent increase in spectrin breakdown products for each group over sham control values. Data shown are the mean percent increase in spectrin breakdown products for each group (sham =100%)±S.E.M. Icv infusion of K-252a significantly reduced the extent of spectrin proteolysis, from about 140± 15% (in the absence of K-252a) to approximately 102±10% (in the presence of K-252a) of sham values.

Figure 11:
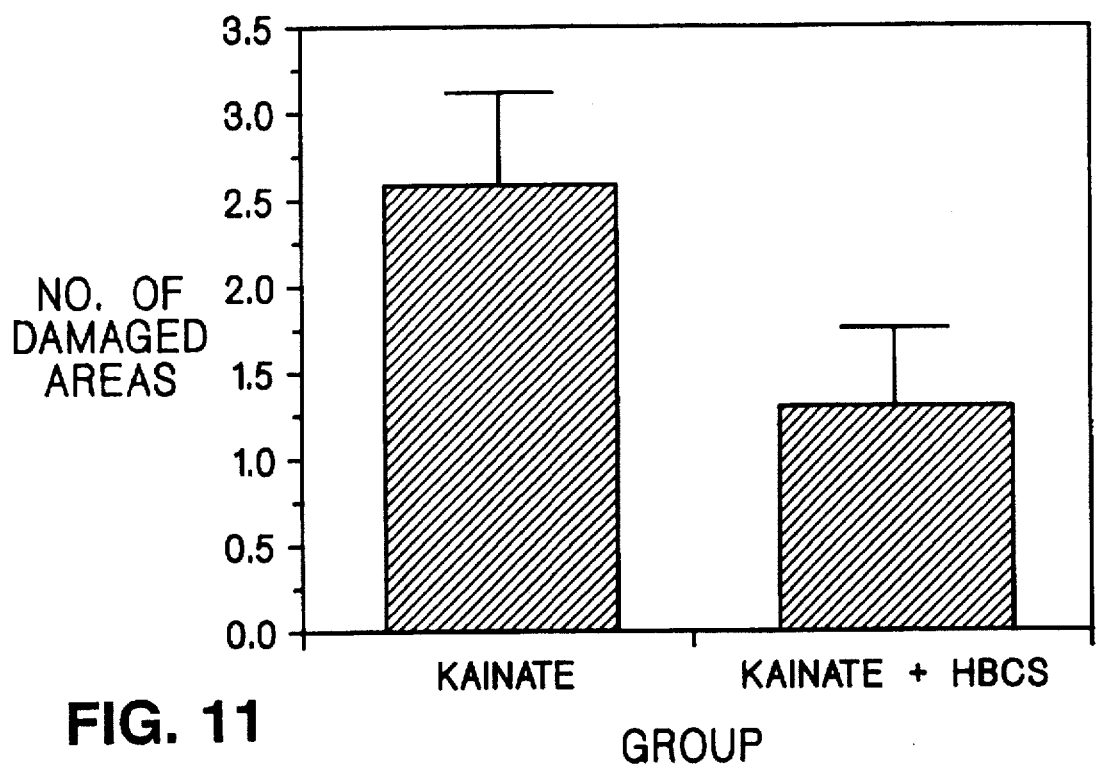
FIG. 11 is a graph illustrating the effect of HBCS on kainate-induced damage to the hippocampus.

FIG. 11 shows the effect of HBCS on kainate-induced neuronal degeneration in the hippocampus. Cannulated female Sprague-Dawley rats received 0.8 μg of HBCS, or vehicle, 40 minutes prior to and about 4 hours following kainate (0.6 μg) by icv infusion. Two weeks later the brains were excised, frozen, sectioned and stained for histological analysis, as described below. Data shown are the mean number of sub-regions of the hippocampus damaged for each group, ±S.E.M. HBCS significantly reduced the number of damaged areas within the hippocampus from about 2.5±0.6 (without HBCS treatment) to 1.3±0.5 (with HBCS treatment).

Figure 12:
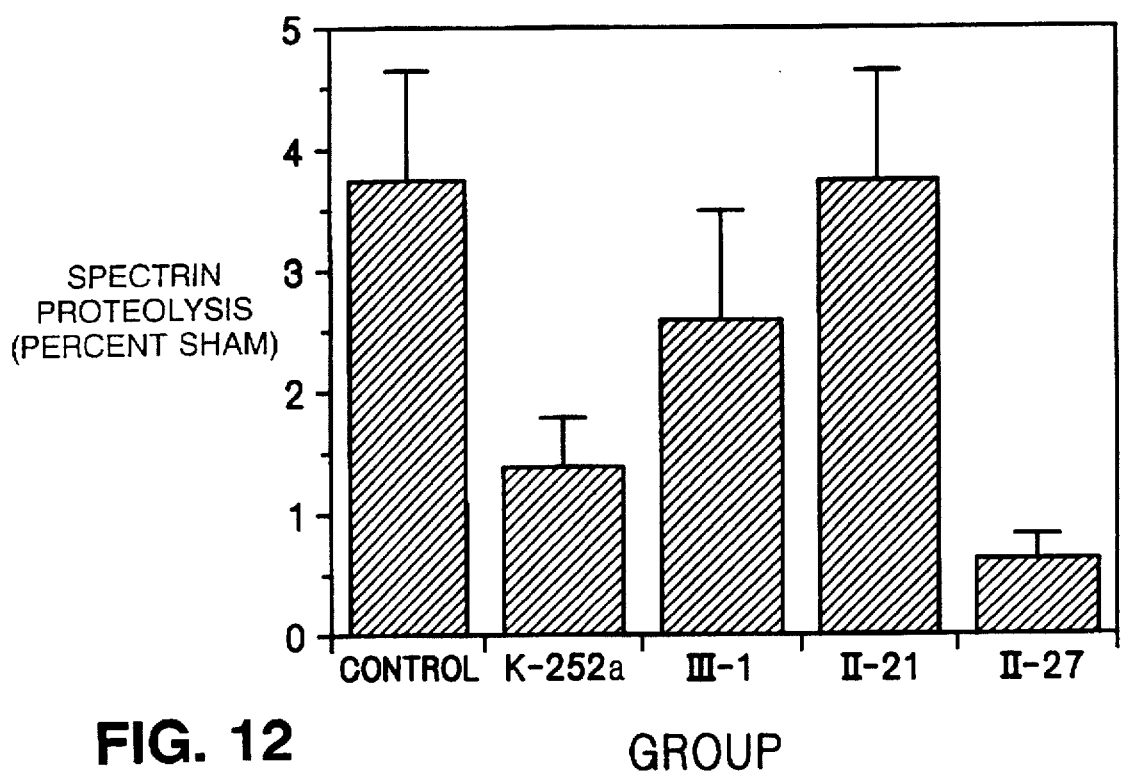
FIG. 12 is a graph illustrating the effect of K-252a functional derivatives on kainate-induced spectrin proteolysis in the rat hippocampus.

FIG. 12 compares the effect of three K-252a functional derivatives on kainate-induced spectrin breakdown in the hippocampus. Female Sprague-Dawley rats received 0.4 μg of K-252a, or compounds III-1, or II-21, or vehicle, together with a neurotoxic dose of kainate (0.6 μg), by icv infusion. Sham control animals received infusions of vehicle, but no kainate or K-252a derivative. Twenty-four hours later, homogenates of the dorsal hippocampus were analyzed for spectrin breakdown products as described below. The magnitude of spectrin proteolysis is expressed as a percent increase in spectrin breakdown products for each group over sham control values. Data shown are the mean percent increase in spectrin breakdown products for each group (sham=100%)±S.E.M. Icv infusion of K-252a reduced the extent of spectrin proteolysis, from about 128±9% (vehicle treatment) to approximately 104±4% (in the presence of K-252a) of sham values. K-252a derivatives III-1 and II-21 failed to prevent kainate-induced spectrin proteolysis.

EXAMPLE 10

K-252a was assayed for the ability to promote survival in striatal cultures. Striata were dissected from embryonic day 17 rat embryos and cells were dissociated by Dispase (neutral protease, Collaborative Research). Neurons were seeded at $5\times10^4$ cells/well ($1.5\times10^5$/cm$^2$) in 96-well plates, the wells having been previously coated with poly-1-ornithine and laminin. Cells were cultured in serum-free N2 medium containing 0.05% bovine serum albumin (Bottenstein and Sato, 1979) at 37° C. in a humidified atmosphere, 5% $CO_2$/95% air. Cell survival was assayed 5 days after seeding using the calcein viable cell fluorimetric assay described in Example 8.

Figure 15:
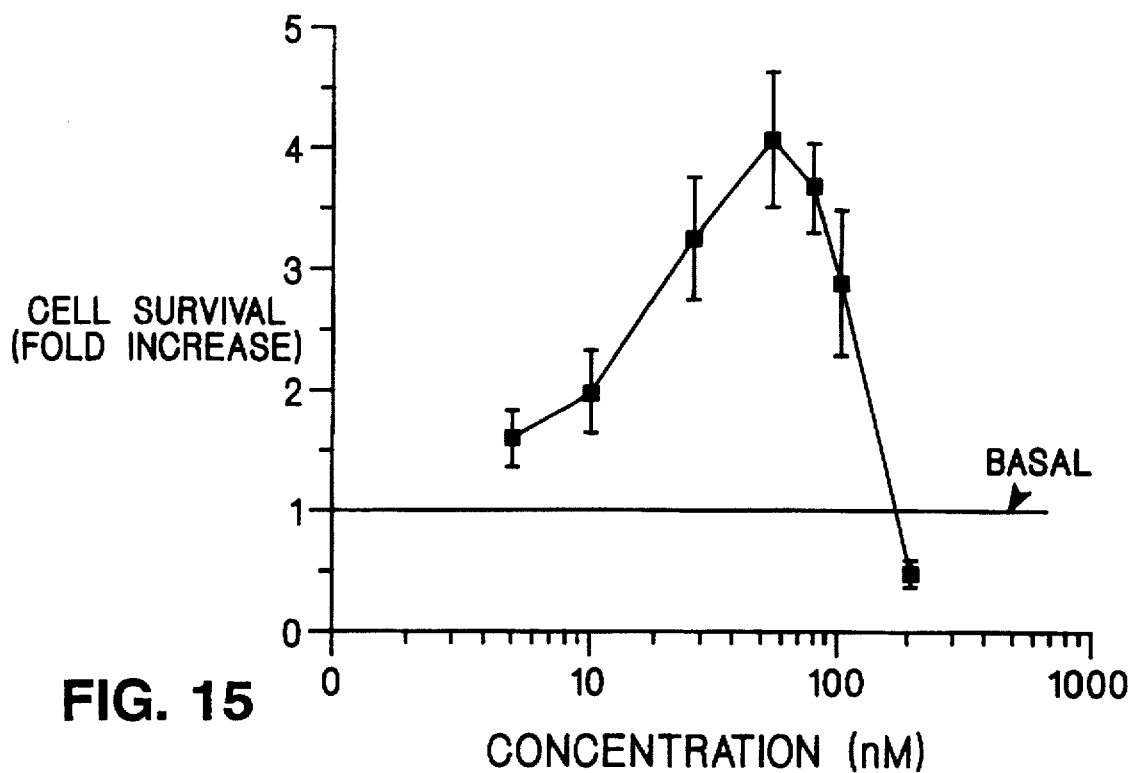
Figure 16:
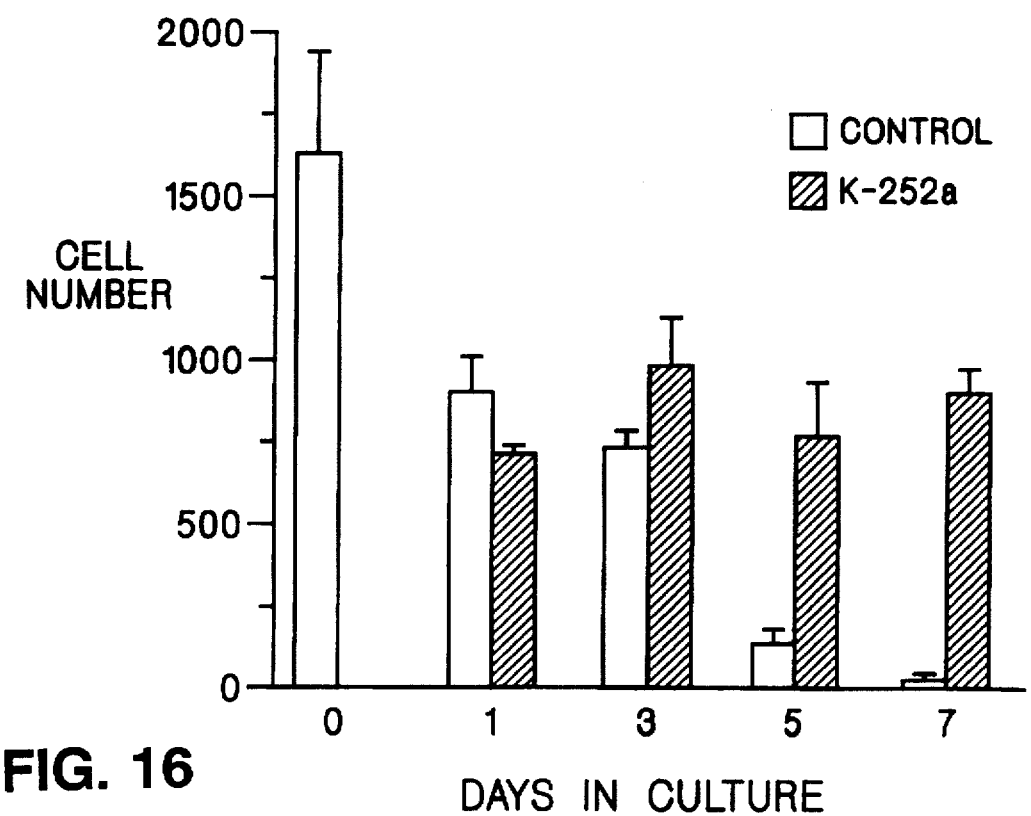

The survival of striatal neurons was enhanced by K-252a in a concentration-dependent manner. Maximum activity was found with 75 nM K-252a, which produced an efficacy of 3–4 fold over control (FIG. 15). In the control cultures, 90% of the neurons plated on day 0 died within 5 days, whereas in cultures treated with K-252a, 50% of the neurons survived (FIG. 16). The survival effect in striatal neurons occurred after 3 days in culture and was sustained for at least 7 days in culture. These results are from a single application of K-252a on the day of culture initiation, and indicate that the effect on neuron survival is sustained.

Figure 17:
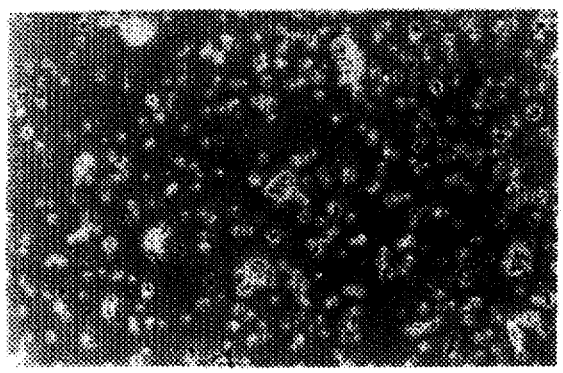
Figure 17:
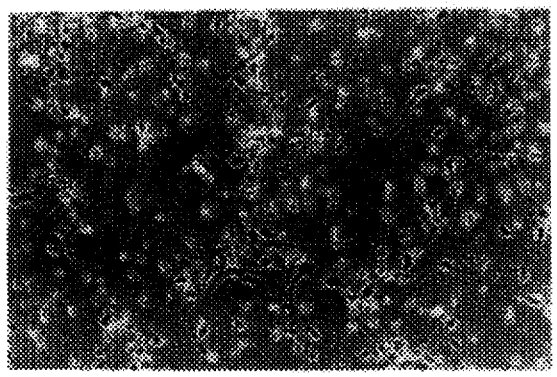

FIG. 17 is a pair of photomicrographs taken from control cultures or cultures treated with 75 nM K-252a. There was an increase in cell survival and neurite outgrowth in these cultures in the presence of 75 nM K-252a.

EXAMPLE 11

Thirty-one functional derivatives of K-252a were tested to determine their potency and efficacy in the striatal cell survival assay of Example 10. FIG. 18 shows data on 18 K-252a derivatives that promoted the survival of striatal neurons.

EXAMPLE 12

Compounds of the invention were assessed for their ability to promote survival and increase ChAT activity in basal forebrain cultures. ChAT activity in these cultures is a biochemical marker for the cholinergic neurons (less than 5% of the cells in culture), which represent the major cholinergic input to the hippocampal formation, olfactory nucleus, interpeduncular nucleus, cortex, amygdala, and parts of the thalamus. Representative compounds of the invention not only increased ChAT activity but in addition increased general survival of neurons in basal forebrain cultures.

The basal forebrain was dissected from embryonic day 17 or 18 rat embryos and the cells were dissociated with Dispase™ (neutral protease, Collaborative Research). Neurons were plated at $5\times10^4$ cells/well ($1.5\times10^5$ cells/cm$^2$) in wells of 96-well plates previously coated with poly-1-ornithine and laminin. Cells were cultured in serum-free $N_2$ medium containing 0.05% bovine serum albumin (BSA) (Bottenstein et al., supra) at 37° C. in a humidified atmosphere of 5% $CO_2$/95% air. ChAT activity was measured in vitro at day six, using a modification of the Fonnum procedure (supra) according to McManaman et al. (supra) and Glicksman et al. (J. Neurochem. 61:210–221, 1993). Cell survival was assessed 5 days after plating using the calcein AM fluorimetric assay described by Bozyczko-Coyne et al. (supra). Culture medium was partially aspirated at the time of assay to leave 50 microliters per well. Eight μM calcein AM stock in 150 μl of Dulbecco's phosphate buffered saline (DPBS; Gibco BRL) was then added to give a final concentration of 6 μM, in 200 μl per well, in a 96-well plate. The plates were incubated for 30 minutes at 37° C., followed by four serial dilutions with 200 μl DPBS. The relative fluorescence of each well was measured using a plate-reading fluorimeter (Cytofluor 2350, Millipore) at an excitation wavelength of 485 nm, an emission wavelength of 538 nm, and a sensitivity setting of #3. The mean fluorescence background calculated from six wells that received calcein AM but contained no cells was subtracted from all values. The linearity of the fluorescence signal was verified for the 30 minute substrate incubation time for the range of cell densities encountered in these experiments. K-252a, as well as at least twelve K-252a derivatives (II-3, II-5, II-10, II-20, II-21, II-22, II-30, II-32, II-51, II-62, II-63, II-64, II-65) promoted the survival of basal forebrain neurons (FIG. 19).

EXAMPLE 13

The following tests were conducted to evaluate the effect of Compound II-51 on cortical cholinergic function when rats were subjected to lesions of the nucleus basalis.

Cholinergic neurons originating from the basal forebrain and projecting to the hippocampus via the septo-hippocampal pathway, or to the cortex via the basalo-cortico pathway, undergo profound degeneration during the course and progression of Alzheimer's disease. There is some degree of correlation between loss of these neurons and decreases in cognitive and memory function in individuals afflicted with this disorder (Fibiger, H. *Trends in Neurosci* 14:220–223, 1991). Several models of cholinergic dysfunction have been proposed which show loss of biochemical markers as well as behavioral deficits. These models parallel the progression of Alzheimer's disease (Olton, D. et al, "Dementia: animal models of the cognitive impairments produced by degeneration of the basal forebrain cholinergic system" in Meltzer, H., (Ed.) *Psychopharmacology: The Third Generation of Progress*, Raven Press, N.Y., 1987, pp. 941–953; Smith, S., *Brain Res. Rev.* 13:103–118, 1988). For example, one model of cholinergic degeneration is excitotoxic lesioning of the nucleus basalis (Wenk. G. et al., *Exp. Brain Res.* 56:335–340, 1984). Lesions in cholinergic neurons within the basal forebrain result in loss of neuronal cell bodies in this region, and subsequent loss of cholinergic terminal markers in the frontal and parietal cortex (Dunnett, S. et al. *Trends Neurosci* 14:494–501, 1991). Using the following methods, Compound II-51 was shown to increase cortical cholinergic function in rats that were subjected to lesions of the nucleus basalis.

Male Sprague-Dawley rats (225–275 grams) were used for all experiments. Unilateral ibotenic lesions of the nucleus basalis magnocellularis were produced by methods known to those of skill in the art (see, e.g., Wenk et al. supra), with modifications as described below. Rats were anesthetized with 50 mg/kg pentobarbital and 5 µg of ibotenic acid (in 1 µl of PBS) was injected, unilaterally, into the nucleus basalis magnocellularis. The coordinates used were from the Paxinos and Watson brain atlas (1.5 mm posterior, 2.8 mm lateral, 7.2 mm dorso-ventral). Injections took place over a period of 6 minutes. Dye injections indicated that the injections went directly into the nucleus basalis.

Compound II-51 was dissolved in 30% Solutol™ at concentrations of 0.01 to 0.3 mg/ml. The compound (or the Solutol™ vehicle) was administered subcutaneously one day after, or 6 hours prior to, inducing lesions in the nucleus basalis, and every 48 hours thereafter. Doses were 0.01, 0.03, 0.10 and 0.30 mg/kg. Experiments were terminated from 4 to 21 days after inducing lesions. ChAT activity was measured in tissue homogenates of the frontal-parietal cortex by the method of Fonnum (supra). ChAT activity in the frontal cortex, ipsilateral to the side of the lesion was compared and normalized to ChAT activity on the contralateral (lesion-free side). CHAT activity is expressed as the ipsilateral to contralateral ratio.

The data were analyzed by ANOVA and differences between treatments determined by post-hoc Tukey's test. Means were considered significantly different if p<0.05.

In animals in which lesions were made in the nucleus basalis, there was a time dependent decrease in cortical ChAT activity with maximum loss dacurring between 3 and 7 days after lesion (Table 6). Route of administration, doses and dosing schedule were based on preliminary data showing the effects of Compound II-51 on ChAT levels in the basal forebrain of adult rats. To assess the effects of Compound II-51 on ChAT levels (i.e., on cholinergic function) in animals with lesions, the drug was administered one day after inducing lesions for 14 to 21 days, or 6 hours prior to surgery for 4 days.

TABLE 6

Time Course of Loss of Cortical ChAT Activity after Inducing Unilateral Lesions in the Nucleus Basalis Magnocellularis[a]

| Lesion Time (hrs.) | Injection | ChAT Activity (Ipsi/Contra ratio) |
|---|---|---|
| No lesion Control | — | 96 ± 8 |
| 8 hrs. | Ibotenic acid (5 µg) | 97 ± 14 |
| 24 hrs. | Ibotenic acid (5 µg) | 105 ± 11 |
| 72 hrs. | Ibotenic acid (5 µg) | 74 ± 11[b] |
| 168 hrs. (7 days) | Ibotenic acid (5 µg) | 70 ± 7[b] |

[a]Unilateral lesions were induced in the NBM of rats. Frontal cortex was assayed for ChAT activity at indicated time after lesion.
[b]Indicates significantly different from lesion-free control (p < 0.05).

Dose-response studies with Compound II-51 were conducted at doses of 0.01, 0.03 and 0.10 mg/kg (Table 7). Subcutaneous injections of Compound II-51 were given on alternate days for 21 days, starting one day after inducing lesions with Ibotenic acid. Results showed that at a dose as low as 0.03 mg/kg, Compound II-51 was effective in attenuating the decease in cortical CHAT activity (Table 7).

TABLE 7

Effects of Systematically Administered Compound II-51 on Cortical ChAT Activity in NBM Rats with Lesions: Dose-Response Study[a]

| Lesion Treatment | Dose Compound II-51 | ChAT Activity (Ipsi/Contra ratio) |
|---|---|---|
| No lesion | — | 98.4 ± 4.5 |
| With lesion | Vehicle | 67.4 ± 7.2[b] |
| With lesion | 0.01 mg/kg QOD | 70.1 ± 11.2 |
| With lesion | 0.03 mg/kg QOD | 93.8 ± 14.9[c] |
| With lesion | 0.10 mg/kg QOD | 87.9 ± 11.6[c] |

[a]Unilateral lesions were induced in the NBM of rats. Twenty-four hours after inducing lesions, subcutaneous administration of Compound II-51 commenced. Twenty-one days after lesioning animals were sacrificed and cortical ChAT activity assessed.
[b]Indicates significantly different than control (p < 0.05).
[c]Indicates significantly different than lesion alone.

Systemic administration of Compound II-51 attenuated the decrease in cholinergic function in the frontal cortex measured at 4, 14 and 21 days after inducing lesions (Table 8). In rats with unilateral lesions, ChAT activity on the contralateral side was unchanged, suggesting that Compound II-51 only affected neurons with lesions.

TABLE 8

Effects of Systematically Administered Compound II-51 on Cortical ChAT Activity in NBM Rats with Lesions: Time-Response Study[a]

| Lesion Time (Days) | Dose Compound II-51 | ChAT Activity (Ipsi/Contra ratio) |
|---|---|---|
| No lesion Control | — | 99 ± 6 |
| 4 days | Vehicle | 77 ± 6[b] |
| | 0.1 mg/kg (QOD) | 96 ± 12[c] |
| 14 days | Vehicle | 72 ± 8[b] |
| | 0.1 mg/kg (QOD) | 94 ± 6[c] |
| 21 days | Vehicle | 66 ± 8[b] |
| | 0.1 mg/kg (QOD) | 87 ± 7[c] |

[a]Unilateral lesions were induced in the NBM of rats. Six hours prior or 1 after inducing lesions, subcutaneous administration of Compound II-51 commenced. Frontal cortex was assayed for ChAT activity at indicated time after lesion.
[b]Indicates significantly different from control (p < 0.05).
[c]Indicates significantly different from lesion + vehicle at same time point.

EXAMPLE 14

An in ovo model can be used to evaluate the ability of a compound to influence developmentally programmed motoneuron death.

In the chick, somatic motoneurons undergo naturally occurring death between embryonic days 6 and 10 (E6 and E10) (Chu-Wang et al., *J. Comp. Neurol.* 177:33–58, 1978; Hamburger, *J. Comp. Neurol.* 160:535–546, 1975; McManaman et al., *Neuron* 4:891–898, 1990). During this period, the number of motoneurons on the two sides of the lumbar spinal cord of developing chick embryos is reduced from about 46,000 to 23,000.

Chick embryos (E6-E9) were treated with either vehicle (5% Solutol™ HS 15, BASF Aktiengesellschaft) or concentrations of Compound II-51 as described. The treatments (50 μl) were applied to the vascularized chorioallantoic membrane through a window in the shell by the method of Oppenheim et al. (*Science* 240:919–921, 1988). Embryos were sacrificed on E10 and spinal chords were removed, fixed in Carnoy's solution (10% acetic acid, 60% ethanol, 30% chloroform), embedded in paraffin, sectioned into 8 μm sections, and stained with thionin as described previously (Oppenheim et al., supra). Motoneurons (identified by morphology and position) were counted blind in every tenth section according to previously established criteria (Oppenheim et al., *J. Comp. Neurol.* 210:174–189, 1982; Oppenheim et al., *J. Comp. Neurol.* 246:281–286, 1986).

Figure 20:
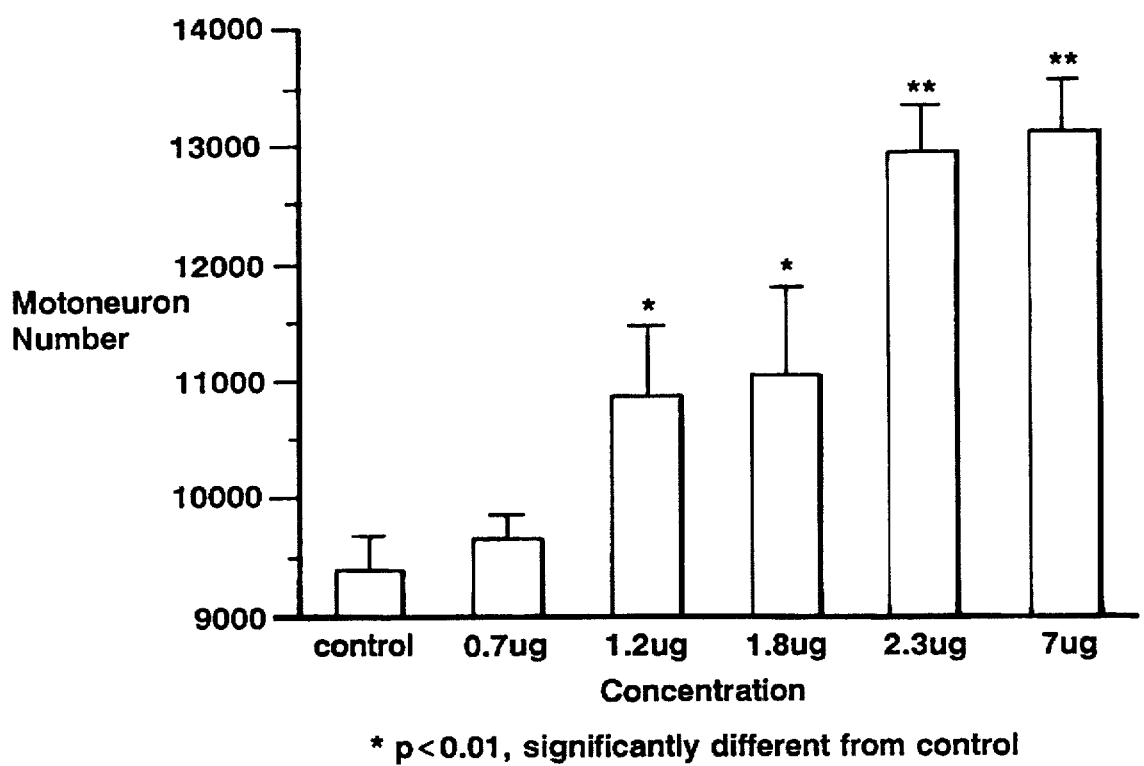
FIG. 20 is a bar graph demonstrating that Compound II-51 prevents developmental programmed motoneuron death in ovo.

Daily application of compound II-51 to the chorioallantoic membrane of E6 to E9 chicks in ovo resulted in a dose-dependent increase in the number of surviving lumbar motoneurons (FIG. 20). At the lowest effective dose tested (1.17 μg/egg) there was a 16% enhancement in motoneuron survival. The maximal effect was achieved at a dose of 2.3 μg/egg, resulting in a 40% increase in motoneuron survival in treated versus control, vehicle-treated, embryos. At 7 μg/egg there was no further increase in motoneuron survival, indicating that in this situation a maximal response had been achieved at 2.3 μg/egg.

EXAMPLE 15

Motoneurons in the hypoglossal nucleus innervate the tongue via the hypoglossal nerve. In adult rats, transection of the hypoglossal nerve results in a dramatic loss of ChAT activity in the motoneurons of the hypoglossal nucleus without affecting cell number. The loss of ChAT activity serves as a model for reversion to an immature phenotype.

The left hypoglossal nerve was cut under the Dawleydigastric muscle of the neck of each adult female Sprague-rat (120–180g) under Nembutal anesthesia. Fifty microliters of compound II-51 in 10% Solutol™ (HS 15, BASF Aktiengesellschaft) or vehicle alone was applied to a piece of gelfoam, then the proximal end of the transected nerve together with the gelfoam was wrapped in parafilm. At the end of 7 days, rats were perfused under deep anesthesia with 4% paraformaldehyde in Sorenson's buffer (0.1M NaPO$_4$, pH 7). The brainstem was removed and immersed in fixative for 24 hours, then rinsed well and placed in 30% sucrose for cryoprotection prior to sectioning. Forty micron coronal sections of the brain were cut and stored in Sorenson's buffer at 4° C. until stained. The hypoglossal nucleus spanned 40–48 sections and every fifth section was processed for immunohistochemistry using the anti-ChAT mouse monoclonal antibody, 1E6, as previously described (Chiu et al., *J. Comp. Neurol.* 328:351–363, 1993). ChAT immunoreactive neurons were visualized in sections by avidin-biotin amplification with the Vectastain Elite ABC™ kit (Vector Laboratories, Burlingame, Calif.).

Figure 21:
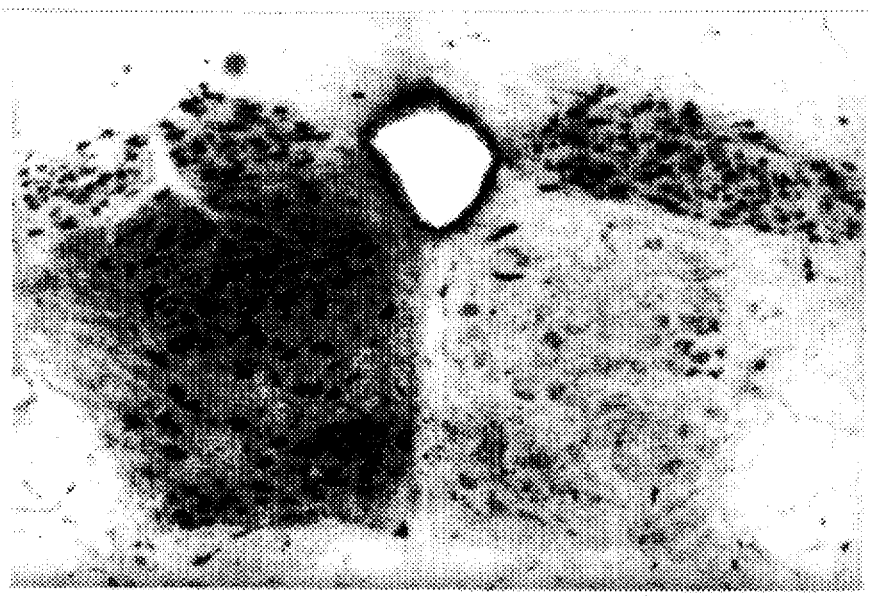
FIG. 21 is a photographic demonstration that Compound II-51 prevents the axotomy-induced loss of CHAT immunoreactivity in the adult hypoglossal nucleus.
Figure 21:
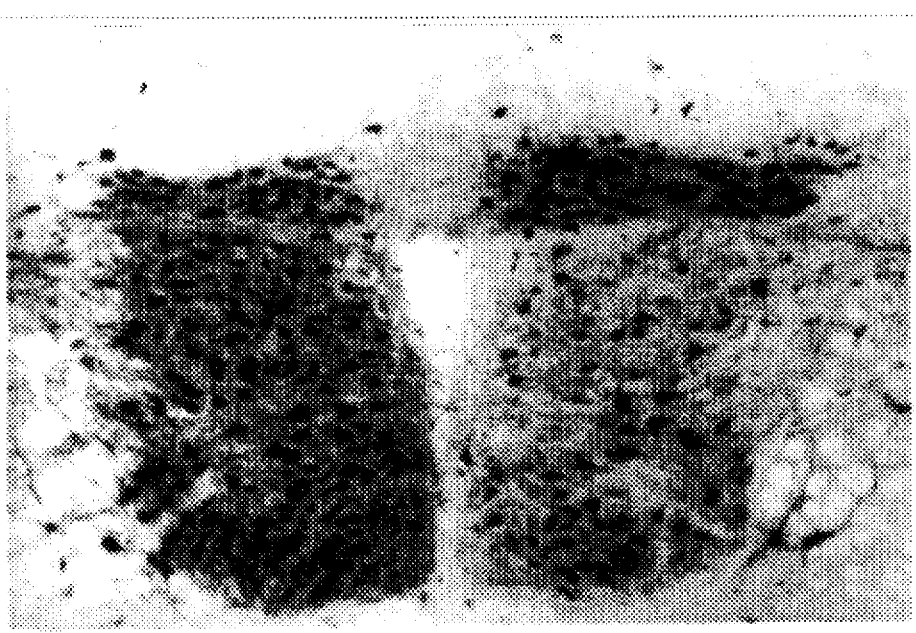

Every fifth section from the hypoglossal nucleus was processed and immunoreactive cells in the control (uninjured) and axotomized sides of each animal were counted. Results are expressed as the percentage of ChAT-immunoreactive neurons on the axotomized side in relation to the number of ChAT-immunoreactive neurons on the uninjured side. Application of 100 μg of compound II-51 to the cut end of the hypoglossal nerve resulted in a significant number of ChAT-immunoreactive neurons (33.7%±9.9 (mean±SEM)) (FIG. 21). In contrast, there were very few ChAT-immunoreactive neurons (8.07%±2.9 (mean±SEM)) in the vehicle-treated control animals.

Preparatory Methods

EXAMPLE 16

Compounds (V)

The processes for producing Compounds (V) are described below.

Process 1

Compound (V-1) (examples of Compound (V) in which $R^1$ is $CH_2So_2R^7$ and X is $CO_2R^5$) can be prepared by the following reaction step:

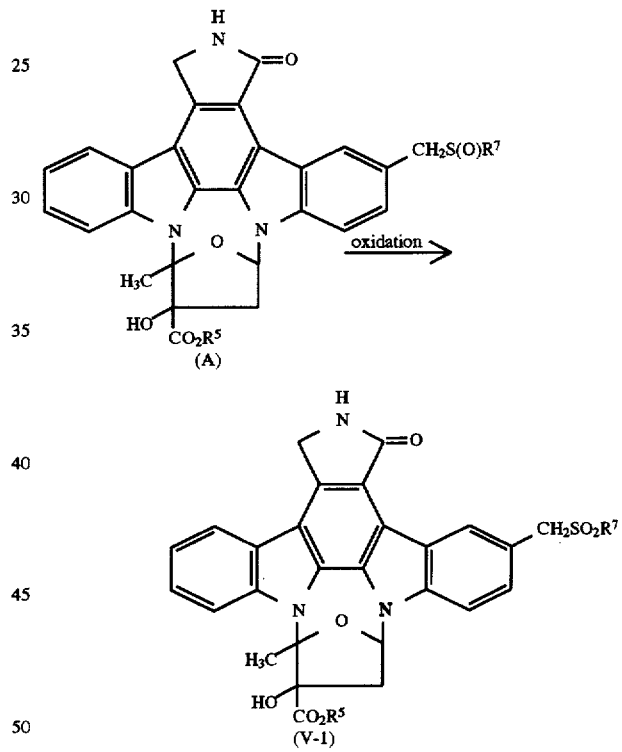

($R^5$ represents lower alkyl or $CH_2NHCO_2R^6$ in which $R^6$ represents lower alkyl or aryl; $R^7$ represents lower alkyl.)

The starting compound (A) is disclosed in Japanese Published Unexamined Patent Application No. 295588/88 (hereby incorporated by reference).

Compound (V-1) can be obtained by treatment of Compound (A) with 1 to 1.5 equivalents of an oxidant. An example of the oxidant is m-chloroperbenzoic acid. As a reaction solvent, a halogenated hydrocarbon such as methylene chloride, chloroform, or ethylene dichloride, or the like is used. The reaction is completed in 0.5 to 1 hour at −20° to 30° C.

Process 2

Compounds of Formula (V-2) (examples of Compound (V) in which $R^1$ is hydrogen and X is $CH_2NHCO_2R^6$] can be prepared by the following reaction step:

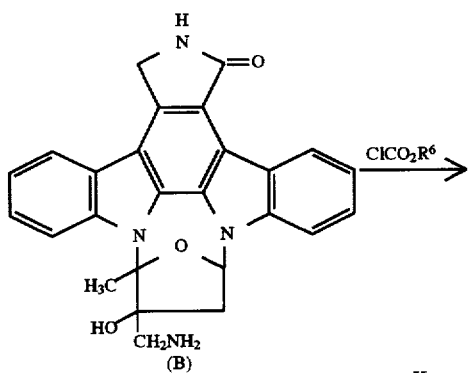

(B)

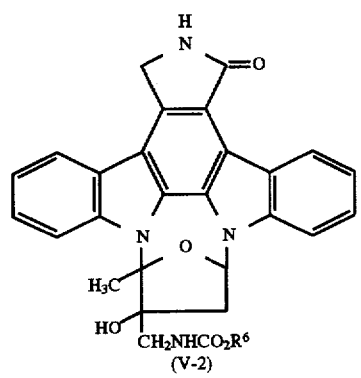

(V-2)

$R^6$ represents lower alkyl or aryl.

The starting compound (B) is disclosed in Japanese Published Unexamined Patent Application No. 155285/87 (hereby incorporated by reference).

Compound (V-2) can be obtained by reaction of Compound (B) with 1 to 3 equivalents $ClCO_2R^6$ in the presence of 1 to 3 equivlents of a base. An example of the base is triethylamine. As a reaction solvent, a halogenated hydrocarbon such as methylene chloride, chloroform, or ethylene dichloride, or the like is used. The reaction is completed in 0.5 to 3 hours at −10° to 30° C.

EXAMPLE 17
Compound II-49

Compound (A; $R^5$=$CH_3$ and $R^7$=$C_2H_5$) (27 mg, 0.05 mmol) was dissolved in 1 ml of chloroform, and then 10 mg (0.06 mmol) of m-chloroperbenzoic acid was added thereto under ice cooling, followed by stirring at the same temperature for 45 minutes. After dilution with chloroform, the mixture was washed successively with a 8% aqueous solution of sodium thiosulfate, a saturated aqueous solution of sodium bicarbonate, water, and a saline solution, and dried over sodium sulfate. After evaporation of the solvent, the residue was subjected to silica gel column chromatography (chloroform/methanol=95/5) to give 17.7 mg (yield 62%) of Compound II-49.

$^1$H-NMR (DMSO-$d_6$) δ (ppm): 1.298(3H, t, J=7.5 Hz), 2.037 (1H, dd, J-5.0, 14.1 Hz), 2.153(3H, s), 3.096(2H,q, J=7.5 Hz), 3.266 (2H, s), 3.929(3H, s), 4.985 (1H, d, J=17.0 Hz), 5.043(1H, d, J=17.0Hz), 6.348(1H, s), 7.147 (1H, dd, J=4.9, 7.1 Hz), 7.345–8.070(6H, m), 8.612(1H, s), 9.232 (1H, d, J=1.5 Hz)

FAB-MS (m/z): 574 (M+1)$^+$

EXAMPLE 18
Compound II-57

Compound (B) (43.8 mg, 0.1 mmol) was dissolved in 1 ml of tetrahydrofuran, and then 9.3 μl (0.12 mmol) methyl chloroformate and 28 μl(0.12 mmol) of triethylamine were added thereto, followed by stirring for 50 minutes under ice cooling. After dilution with tetrahydrofuran, the mixture was washed with a saline solution, and dried over sodium sulfate. After evaporation of the solvent, the residue was subjected to silica gel column chromatography (chloroform/methanol=99/1) to give 32.6 mg of Compound II-57.

$^1$H-NMR (CDCl$_3$) δ (ppm): 2.099(3H, s), 2.679(1H, m), 3.204(1H, dd, J=6.7 m 13.8 Hz), 3.837(3H, s), 4.446 (1H, d, J=17.3 Hz), 4.634 (1H, d, J=17.6 Hz), 5.497 (1H, brs), 6.591(1H, brs), 7.010–8.037(7H, m), 8.592(1H, d, J=6.6 Hz)

FAB-MS (m/z): 497 (M+1)$^+$

EXAMPLE 19
Compound II-38

Substantially the same procedure as in Example 18 was repeated using 43.8 mg (0.1 mmol) of Compound (B) and 15 μl of phenyl chloroformate to give 27.8 mg (yield 50%) of Compound II-38.

$^1$H-NMR (CDCl$_3$) δ (ppm): 2.111(3H, s), 2.890(1H, brd, J=13.7 Hz), 3.262(1H, dd, J=7.5, 13.9 Hz), 3.742(1H, d, J=13.4 Hz), 3.967(1H, d, J=12.9 Hz), 4.582(1H, d, J=16.3 Hz), 5.342(1H, brs), 5.906(1H, brs), 6.550 (1H, brs), 7.005–8.042(12H, m), 8.596(1H, d, J=7.6 Hz)

FAB-MS (m/z): 559 (M+1)$^+$

EXAMPLE 20

Figure 22:
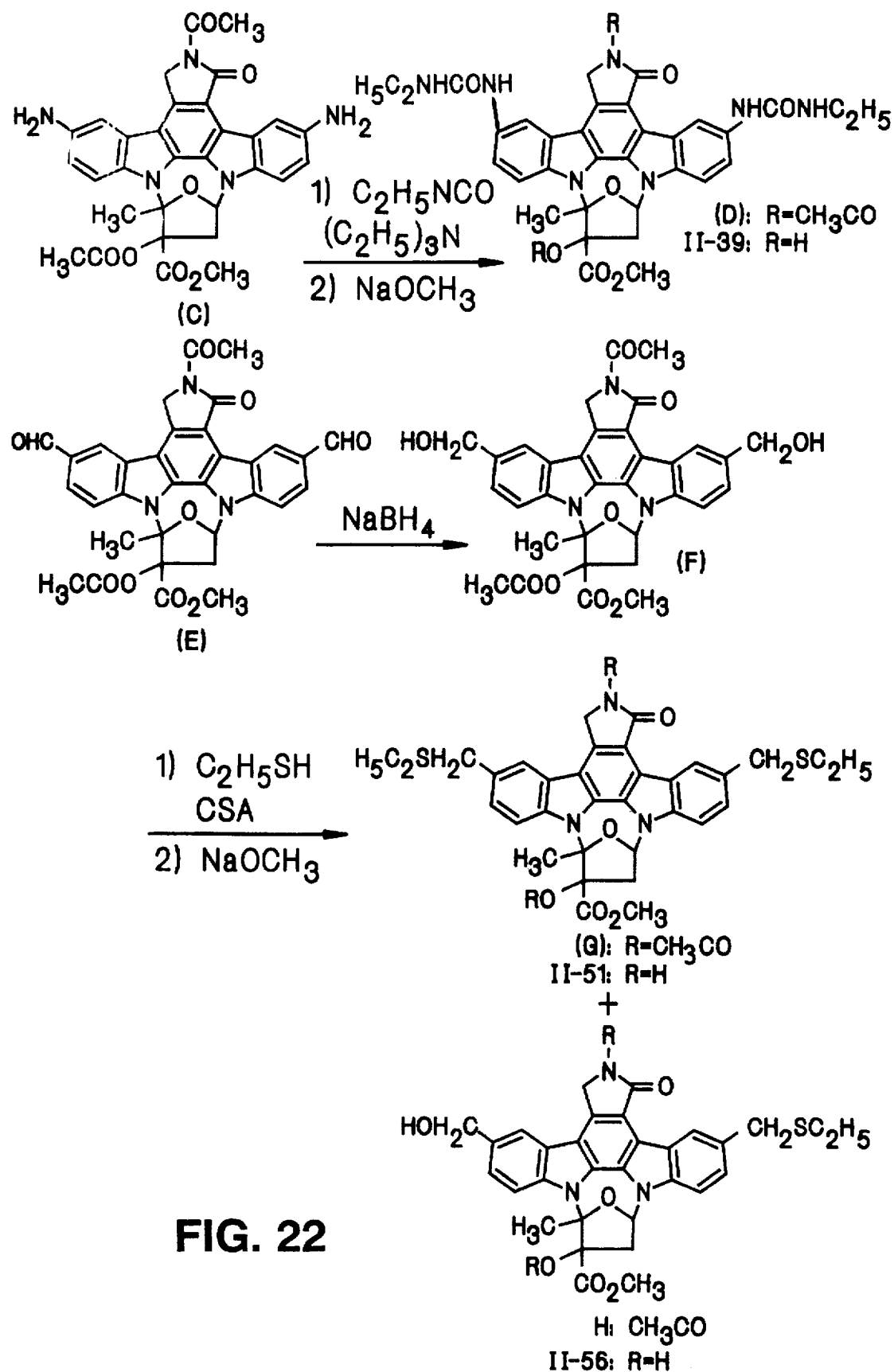
FIG. 22 is a diagram showing the synthesis of Compound H from starting Compound C.

(The synthesis of Compound H from Compound C is shown in FIG. 22.)

Compound II-39

Compound (C) (Japanese Published Unexamined Patent Application No. 295588/88; hereby incorporated by reference) (20 mg, 0.035 mmol) was dissolved in 1 ml of chloroform, and then 14.6 μl (0.105 mmol) of triethylamine and 13.9 μl (0.175 mmol) of ethyl isocyanate were added thereto, followed by stirring at room temperature for 2 hours. To the solution was added 1 ml of methanol, followed by dilution with chloroform. The mixture was washed successively with water and a saline solution, and dried over sodium sulfate. After evaporation of the solvent, the residue was subjected to silica gel column chromatography (chloroform/methanol=98/2) to give 21 mg (yield 84% of Compound (D).

$^1$H-NMR (CDCl$_3$) δ (ppm): 1.195(3H, t, J=7.2 Hz), 1.222(3H, t, J=7.2 Hz), 1.664(3H, s), 2.194(3H, s), 2.555 (3H, s), 3.346(4H, q, J=7.2 Hz), 3.820(1H, dd, J=7.5, 14.6 Hz), 3.938(3H, s), 5.036(1H, d, J=17.7 Hz), 5.125(1H, d, J=17.2 Hz), 6.745(1H, dd, J=4.8, 7.4 Hz), 7.260–7.898(5H, m), 8.690(1H, d, J=1.9 Hz)

FAB-MS (m/z): 724 (M+1)$^+$

Compound (D) (9 mg, 0.012 mmol) was dissolved in a mixture of 0.2 ml of tetrahydrofuran and 0.2 ml of methanol, and then 2 μl of 28% sodium methoxide/methanol was added thereto, followed by stirring at room temperature for 10 minutes. To the solution was added 0.1 ml of a 5% aqueous solution of citric acid, followed by dilution with chloroform. The mixture was washed successively with water and a saline solution, and dried over sodium sulfate. After evaporation of the solvent, the residue was subjected to silica gel column chromatography (chloroform/methanol=9/1) to give 8 mg of Compound II-39.

1H-NMR (DMSO-$d_6$) δ (ppm): 1.086(3H, t, J=7.1 Hz), 1.099 (3H, t, J=7.1 Hz), 1.948(1H, dd, J=4.8, 14.1 Hz), 2.107(3H, s), 3.158(4H, m), 3.910(3H, s), 4.880(1H, d, J=17.7 Hz), 4.931(1H, d, J=16.9 Hz), 7.028(1H, dd, J=5.0, 7.1 Hz), 7.332–8.287(5H, m), 8.838(1H, d, J=2.1 Hz)

FAB-MS (m/z): 640 (M+1)$^+$

EXAMPLE 21

Compounds II-51 and II-56

Compound (E) (Japanese Published Unexamined Patent Application No. 295588/88; supra) (60.7 mg, 0.1 mmol) was dissolved in a mixture of 5 ml of chloroform and 1 ml of methanol, and then 11 mg (0.3 mmol) of sodium borohydride was added thereto under ice cooling, followed by stirring at the same temperature for 15 minutes. After dilution with chloroform, the mixture was washed successively with water and a saline solution, and dried over potassium carbonate. After evaporation of the solvent, the residue was subjected to silica gel column chromatography (Chloroform/methanol/triethylamine=98/2/0.5) to give 36 mg (yield 59%) of Compound (F).

$^1$H-NMR (DMSO-$d_6$) δ (ppm): 1.650(3H, s), 2.027(1H, dd, J=4.9, 14.5 Hz), 2.126(3H, s), 3.843(1H, dd, J=7.4, 14.5 Hz), 3.891(3H, s), 4.607(2H, s), 4.673(2H, s), 5.125(2H, s), 7.099(1H, dd, J=5.0, 7.3 Hz), 7.437–7.907(5H, m), 8.812 (1H, d, J=0.8 Hz)

FAB-MS (m/z): 612 (M+1)$^+$

Compound (F) (159 mg, 0.26 mmol) was dissolved in 15 ml of chloroform, and then 0.8 ml (10.4 mmol) of ethanethiol and 24 mg (0.104 mmol) of camphorsulfonic acid were added thereto, followed by stirring at room temperature for 12 hours. The solution was washed successively with a saturated aqueous solution of sodium bicarbonate, water, and a saline solution, and dried over sodium sulfate. After evaporation of the solvent, the residue was subjected to silica gel column chromatography (ethyl acetate/toluene=1/9-chloroform/methanol=99/1) to give 43 mg of Compound (G) and 75 mg of Compound (H).

Compound (G)

$^1$H-NMR (CDCl$_3$) δ (ppm): 1.292(3H, t, J=7.4 Hz), 1.297 (3H, t, J=7.4 Hz), 1.799(3H, s), 2.141(1H, dd, J=5.0, 14.5 Hz), 2.256(3H, s), 2.532(2H, q, J=7.4 Hz), 2.553(2H, q, J=7.4 Hz), 2.869(3H, s), 3.971(1H, dd, J=7.5, 14.5 Hz), 3.992(2H, s), 4.005 (3H, s), 4.021(2H, s), 5.416(1H, dd, J=17.5 Hz), 5.459(1H, d, J=17.4 Hz), 6.989(1H, dd, J=5.1, 7.4 Hz), 7.509–7.963(5H, m), 9.134(1H, d, J=1.2 Hz)

FAB-MS (m/z): 700 (M+1)$^+$

Compound (H)

$^1$H-NMR (CDCl$_3$) δ (ppm): 1.294(3H, t, J=7.4 Hz), 1.799(3H, s), 2.149(1H, dd, J=5.0, 14.6 Hz), 2.273(3H, s), 2.533(2H, q, J=7.4 Hz), 2.813 (3H, s), 3.972(1H, dd, J=7.4, 14.6 Hz), 4.008(3H, s), 4.015(2H, s), 4.951 (2H, s), 5.377 (1H, d, J=17.4 Hz), 5.418(1H, d, J=17.4 Hz), 6.973(1H, dd, J=5.0, 7.5 Hz), 7.481–8.037 (5H, m), 9.093(1H, d, J=1.2 Hz)

FAB-MS (m/z): 656 (M+1)$^+$

Substantially the same procedure as in Example 20 was repeated using 34 mg of Compound (G) to give 18.7 mg of Compound II-51.

$^1$H-NMR (CDCl$_3$) δ (ppm): 1.300(3H, t, J=7.4 Hz), 1.325(3H, t, J=7.4 Hz), 2.185(3H, s), 2.514(1H, dd, J=4.8, 14.5 Hz), 2.540(2H, q, J=7.4 Hz), 2.555(2H, q, J=7.4 Hz), 3.384(1H, dd, J=7.5, 14.5 Hz), 3.941(2H, s), 3.976(2H, s), 4.094(3H, s), 4.836(1H, d, J=16.4 Hz), 4.910(1H, d, J=16.3 Hz), 5.781 (1H, s),6.845 (1H, dd, J=4.8, 7.5 Hz), 7.371–7.843(5H, m),8.998(1H, s)

FAB-MS (m/z): 616 (M+1)$^+$

Substantially the same procedure as in Example 20 was repeated using 30 mg of Compound (H) to give 20.4 mg of Compound II-56.

$^1$H-NMR (CDCl$_3$) δ (ppm): 1.280(3H, t, J=7.4 Hz), 2.144(3H, s), 2.391(1H, dd, J=4.9, 14.5 Hz), 2.517(2H, q,J=7.4 Hz), 3.320(1H, dd, J=7.4, 14.5 Hz), 3.885(2H, s), 4.069(3H, s), 4.521(1H, d, J=16.3 Hz), 4.631(1H, d, J=16.7 Hz), 4.804(2H, s), 5.769(1H, s), 6.830(1H, dd, J=4.8, 7.4 Hz), 7.375–7.771(5H, m), 8.934(1H, s)

FAB-MS (m/z): 572 (M+1)$^+$

EXAMPLE 22

Compound IV-2

Compound II ($Z^1$, $Z^2$=H; $R^1$=Br; $R^2$=H; R=OH; X=CO$_2$CH$_3$) (Japanese Published Unexamined Patent Application No. 120388/87; hereby incorporated by reference) (50 mg, 0.09 mmol) was dissolved in a mixture of 0.5 ml of trifluoroacetic acid and 50 μl of 3N HCl, and the solution was stirred at room temperature for 2 days. The precipitates were collected by filtration and subjected to high performance liquid chromatography (Unisil $_5$C$_{18}$; methanol/water=8/2) to give 8.4 mg of Compound (IV-2).

$^1$H-NMR (DMSO-$d_6$) δ (ppm): 4.947 (2H, s), 7.300–8.010 (6H, m), 8.249(1H, s), 9.266(1H, d, J=2.0 Hz)

FAB-MS (m/z): 390 (M+1)$^+$

EXAMPLE 23

Figure 23:
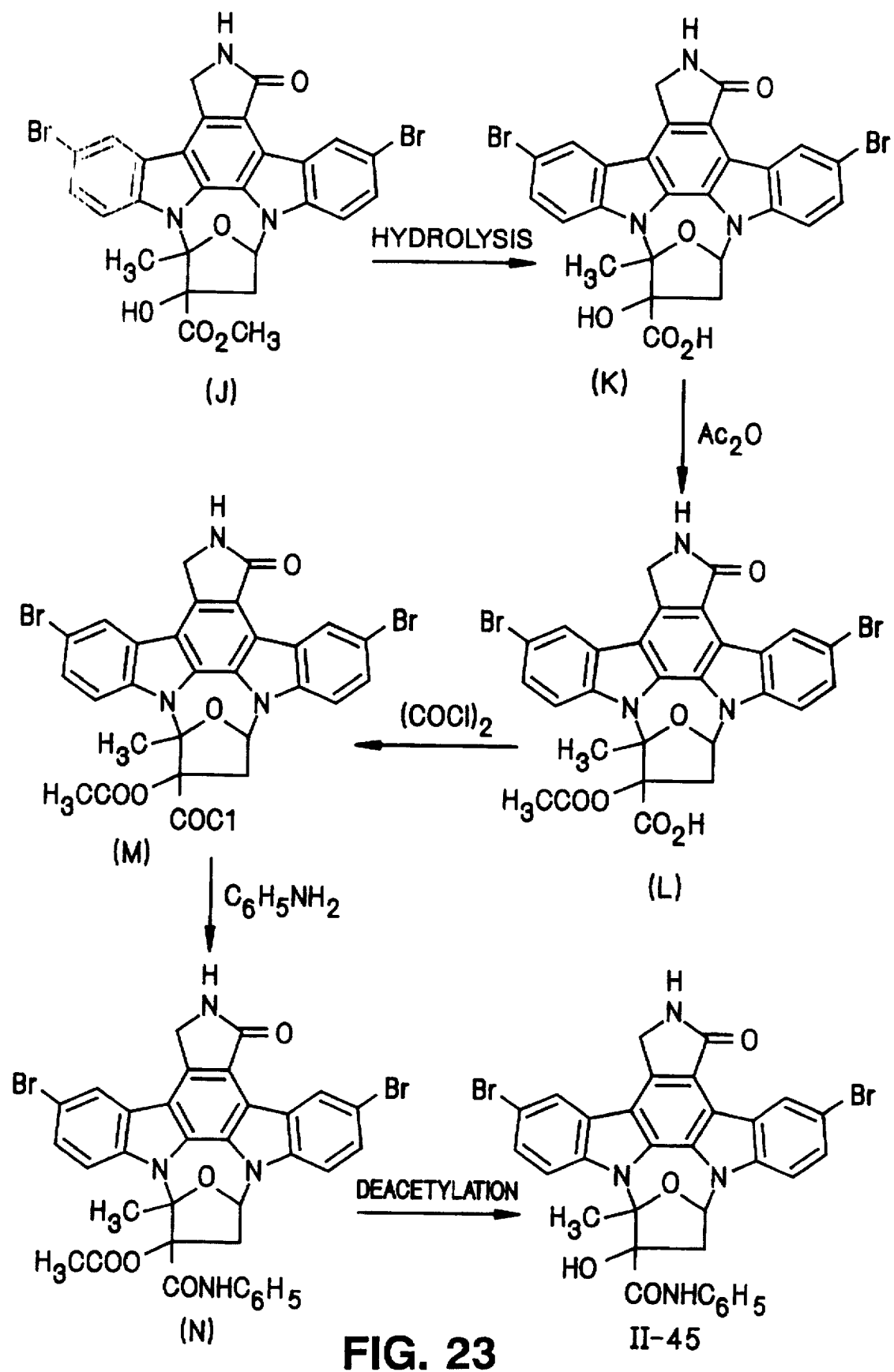
FIG. 23 is a diagram showing the synthesis of Compound II-45 from starting Compound J.

Compound II-45 can be prepared by the reaction steps shown in FIG. 23. The starting Compound (J) is disclosed in Japanese Published Unexamined Patent Application No. 120388/87 (hereby incorporated by reference).

Compound II-45

Compound (J) (200 mg) was dissolved in 1 ml of dimethylformamide, and then 0.25 ml of an aqueous solution of 23.5 mg of sodium hydroxide was added thereto, followed by stirring at room temperature for 4 hours. After 1N hydrochloric acid was added to adjust the pH of the solution to 1–2, the precipitates were collected by filtration to give 178 mg (yield 91%) of Compound (K).

$^1$H-NMR (DMSO-$d_6$) δ (ppm): 1.965(1H, dd, J=4.8, 14.0 Hz), 2.184(3H, s), 3.364(1H, dd, J=7.5, 14.0 Hz), 5.029 (1H, d, J=18.1 Hz), 5.071(1H, d, J=18.0 Hz), 7.133 (1H, dd, J=4.9, 7.5 Hz), 7.595–8.189(5H, m), 8.733 (1H, s), 9.398 (1H, d, J=2.1 Hz)

Compound (K) (168 mg), was dissolved in 3 ml of pyridine, and then 0.44 ml (4.7 mmol) of acetic anhydride was added thereto, followed by stirring at room temperature for 4 days. After evaporation of the solvent, 4 ml of 1N hydrochloric acid was added to the residue, and the precipitates were collected by filtration to give 182 mg (yield quantitative) of Compound (L).

$^1$H-NMR (DMSO-$d_6$) δ (ppm): 1.684(3H, s), 2.135(1H, dd, J=4.9, 14.4 Hz), 2.252(3H, s), 3.865(1H, dd, J=7.6, 14.5 Hz), 5.063(2H, s), 7.255(1H, dd, J=4.9, 7.5 Hz), 7.612–8.582(5H, m), 8.760(1H, s), 9.389(1H, d, J=2.1 Hz)

Compound (L) (172 mg) was suspended in thionyl chloride, followed by stirring at 90° C. for 4.5 hours. After evaporation of the solvent, diethyl ether was added to the residue and the precipitates were collected by filtration to give 180 mg of Compound (M).

Compound (M) (67 mg, 0.1 mmol) was dissolved in 2 ml of ethylene dichloride, and then 180 μl of aniline in tetrahydrofuran was added thereto under ice cooling, followed by stirring at the same temperature for 1 hour. After evaporation of the solvent, the residue was dissolved in a mixture of 2 ml of tetrahydrofuran and 0.5 ml of methanol, and then 1 ml of 1N NaOH was added thereto, followed by stirring at room temperature for 3 hours. To the solution was added 1N hydrochloric acid (1.2 ml) for neutralization, followed by dilution with tetrahydrofuran. The mixture was washed with a saline solution and dried over sodium sulfate. After evaporation of the solvent, the residue was subjected to silica gel column chromatography (chloroform/methanol=98/2) to give Compound II-45 (13 mg from 56 mg of isolated Compound N).

¹H-NMR (DMSO-d₆) δ (ppm): 2.110(1H, dd, J=4.9, 13.9 Hz), 2.175(3H, s), 5.019(1H, d, J=18.1 Hz), 5.088(1H, d, J=18.0 Hz), 6.887(1H, s), 7.119–8.201(11H, m), 8.711 (1H, s), 9.391(1H, d, J=2.2 Hz), 10.071(1H, s)

FAB-MS (m/z): 687 (M+1)⁺

EXAMPLE 24

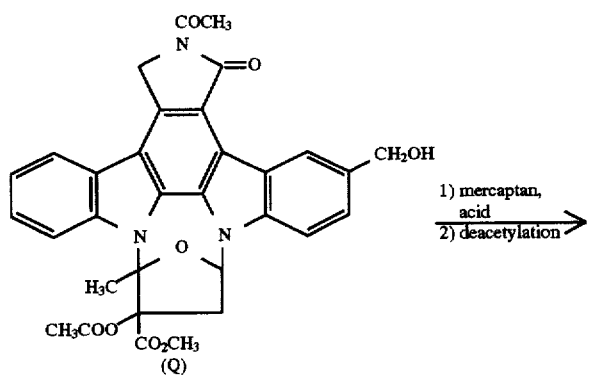

(Q)

The starting compound (Q) is disclosed in Japanese Unexamined Patent Application No. 295588/88.

Compound (Q) (50 mg, 0.0861 mmol) was dissolved in 3 ml of chloroform, and then 200 mg (1.41 mmol) of 2-dimethylaminoethanethiol hydrochloride and 49 mg (0.21 mmol) of (±)-10-camphorsulfonic acid were added thereto, followed by stirring at room temperature for 12 hours. The reaction mixture was washed successively with a saturated aqueous solution of sodium bicarbonate, water, and a saline solution, and dried over sodium sulfate. After evaporation of the solvent, the residue was subjected to preparative thin layer chromatography (chloroform/methanol=99/1) to give 56.3 mg (yield 98%) of N,O-diacetylated Compound II-65.

FAB-MS (m/z): 668 (M+1)⁺

N,O-diacetylated Compound II-65 (36.6 mg, 0.0548 mmol) was dissolved in a mixture of 6 ml of chloroform and 3 ml of methanol, and then 18 μl (0.09 mmol) of 5.1N sodium methoxide was added thereto, followed by stirring at room temperature for 20 minutes. Amberlyst® 15 ion-exchange resin (100 mg) was added to the reaction mixture, followed by stirring for one hour, and insoluble material was separated by filtration. After evaporation of the solvent, the residue was subjected to preparative thin layer chromatography (chloroform/methanol=97/3) to give 28.4 mg (yield 89%) of Compound II-65.

¹H-NMR (DMSO-d₆) δ (ppm): 2.011 (1H, dd, J=4.9, 14.1 Hz), 2.142 (9H, s), 2.460–2.584 (4H, m), 3.404 (1H, dd, J=7.3, 14.1 Hz), 3.923 (3H, s), 3.950 (2H, s), 4.951–5.054 (2H, m), 6.336 (1H, s), 7.111 (1H, dd, J=4.9, 7.3 Hz), 7.338–8.060 (6H, m), 8.595 (1H, s), 9.137 (1H, d, J=1.3 Hz)

FAB-MS (m/z): 585 (M+1)⁺

Compound II-65

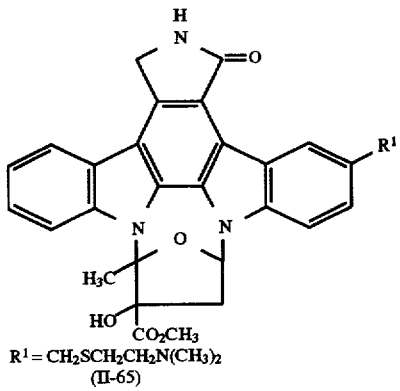

R¹ = CH₂SCH₂CH₂N(CH₃)₂
(II-65)

EXAMPLE 25

Compound II-66

Compound II-66 is prepared, e.g., according to a method of Japanese published unexamined Patent Application No. 155284/87 (hereby incorporated by reference).

EXAMPLE 26

Compound II-75

Compound (P) (Japanese Published Unexamined Patent Application No. 295588/88) (100 mg, 0.173 mmol) and 4-amino-1,2,4-triazole (17.4 mg, 0.207 mmol) were dissolved in a mixture of 4 ml of chloroform and 1.5 ml of tetrahydrofuran, and then 0.05 ml of 3N hydrochloric acid was added thereto, followed by stirring at room temperature for 3.5 hours. After ethyl acetate was added thereto, insoluble matters were collected by filtration and subjected to silica gel column chromatography (chloroform/methanol=95/5) to give 71.9 mg (yield 64%) of N,O-diacetylated Compound II-75.

FABS-MS (m/z): 646 (M+1)⁺

N,O-Diacetylated Compound II-75 (37.5 mg, 0.058 mmol) was dissolved in a mixture of 2 ml of 1,2-dichloroethane and 0.6 ml of methanol, and then 11 μl (0.058 mmol) of 5.1N sodium methoxide in methanol was added thereto, followed by stirring at room temperature for 20 minutes. Amberlyst® 15 (50 mg) was added to the reaction mixture, followed by stirring for 30 minutes, and insoluble matters were filtered off. The insoluble matters were washed well with dichloromethane/methanol/ammonium hydroxide (8/2/0.5), and the combined filtrate was concentrated under reduced pressure. The residue was subjected to silica gel column chromatography to give 26.8 mg (yield 82%) of compound II-75.

$^1$H-NMR (DMSO-d$_6$) δ (ppm): 2.105 (1H, dd, J=5.0, 14.1 Hz), 2.157 (3H, s), 3.444 (1H, dd, J=7.5, 14.1 Hz), 3.973 (3H, s), 5.020 (1H, d, J=17.2 Hz), 5.076 (1H, d, J=17.2 Hz), 6.399 (1H, s), 7.226 (1H, dd, J=5.0, 7.5 Hz), 7.366–8.114 (6H, m), 8.708 (1H, s), 9.219 (2H, s), 9.260 (1H, s), 9.701 (1H, d, J=1.5 Hz)

FAB-MS (m/z): 562 (M+1)$^+$

EXAMPLE 27
Compound II-79

Compound (Q) (Japanese Published Unexamined Patent Application No. 295588/88 (50 mg, 0.0861 mmol) and 2-(butylamino)ethanethiol (0.127 ml, 0.861 mmol) were dissolved in chloroform, and then 300 mg (1.29 mmol) of camphorsulfonic acid was added thereto, followed by stirring at room temperature for 4 days. A saturated aqueous solution of sodium bicarbonate was added to the reaction mixture, and the organic layer was washed with an aqueous solution of sodium chloride and dried over magnesium sulfate. The solvent was evaporated under reduced pressure, and the residue was subjected to silica gel column chromatography (chloroform/methanol=95/5) to give 34.6 mg (yield 58%) of N,O-diacetylated Compound II-79.

FAB -MS (m/z): 697 (M+1)$^+$

Substantially the same procedure as in Example 26 was repeated using 31.1 mg (0.0447 mmol) of N,O-diacetylated Compound II-79 to give Compound II-79 (yield 52%).

$^1$H-NMR (DMSO-d$_6$) δ (ppm): 0.855 (3H, t, J=7.4 Hz), 1.286 (2H, m), 1.510 (2H, m), 2.007 (1H, dd, J=4.9, 14.1 Hz), 2.148 (3H, s), 2.731 (2H, m), 2.843 (2H, m), 3.106 (2H, m), 3.389 (1H, dd, J=7.4, 14.1 Hz), 3.927 (3H, s), 4.032 (2H, s), 4.987 (1H, d, J=17.6 Hz), 5.030 (1H, d, J=17.6 Hz), 6.345 (1H, s), 7.126 (1H, dd, J=4.9, 7.4 Hz), 7.350–8.067 (6H, m), 8.614 (1H, s), 9.161 (1H, s)

FAB-MS (m/z): 613 (M+1)$^+$

EXAMPLE 28
Compound II-80

Compound F (W094/02488, hereby incorporated by reference) (6.19 g, 10.1 mmol) was dissolved in a mixture of 300 ml of 1,2-dichloroethane and 100 ml of methanol, and then 0.5 ml (2.55 mmol) of 5.1N sodium methoxide in methanol was added thereto, followed by stirring at room temperature for 35 minutes. The reaction mixture was poured into ice-water, and insoluble matters were collected by filtration to give 4.95 g (yield 93%) of a compound having bis(hydroxymethyl) in place of bis (dimethylaminoethylthiomethyl) of Compound II-80.

FAB-MS (m/z): 528 (M+1)$^+$

Substantially the same procedure as in Example 27 was repeated using 22.1 mg (0.0419 mmol) of the compound having bis(hydroxymethyl) in place of bis (dimethylaminoethylthiomethyl) of Compound II-80 and 59.4 mg (0.419 mmol) of 2-(dimethylamino) ethanethiol hydrochloride to give 13.1 mg (yield 45%) of Compound II-80.

$^1$H-NMR (DMSO-d$_6$) δ (ppm): 1.999 (1H, dd, J=4.9, 14.2 Hz), 2.134 (3H, s), 2.143 (6H, s), 2.149 (6H, s), 2.461–2.585 (8H, m), 3.378 (1H, dd, J=7.3, 14.2 Hz), 3.922 (3H, s), 3.950 (2H, s), 3.983 (2H, s), 4.954 (1H, d, J=17.7 Hz), 5.012 (1H, d, J=17.7 Hz), 6.322 (1H, s), 7.108 (1H, dd, J=4.9, 7.3 Hz), 7.444–7.952 (4H, m), 8.616 (1H, s), 9.133 (1H, d, J=1.4 Hz)

FAB-MS (m/z): 702 (M+1)$^+$

EXAMPLE 29
Compound II-72

Substantially the same procedure as in Example 27 was repeated using 50 mg (0.0861 mmol) of Compound (Q) and 97.8 mg (0.861 mmol) of 2-aminoethanethiol hydrochloride to give 49.6 mg (yield 90%) of N,O-diacetylated Compound II-72.

FAB-MS (m/z): 641 (M+1)$^+$

Substantially the same procedure as in Example 26 was repeated using 39.5 mg (0.0617 mmol) of N,O-diacetylated Compound II-72 to give 30.2 mg (yield 88%) of Compound II-72.

$^1$H-NMR (DMSO-d$_6$) δ (ppm): 2.014 (1H, dd, J=4.9, 14.1 Hz), 2.146 (3H, s), 2.519 (2H, t, J=7.2 Hz), 2.748 (2H, t, J=7.2 Hz), 3.386 (1H, dd, J=7.5, 14.1 Hz), 3.925 (3H, s), 3.936 (2H, s), 4.979 (1H, d, J=17.0 Hz), 5.029 (1H, d, J=17.0 Hz), 6.330 (1H, s), 7.111 (1H, dd, J=4.9, 7.5 Hz), 7.344–8.059 (6H, m), 8.600 (1H, s), 9.131 (1H, d, J=1.5 Hz)

FAB-MS (m/z): 557 (M+1)$^+$

EXAMPLE 30
Compound VI-1

Compound (R) (I. Antibiotics, 38:1437, 1985, FIG. 24) (1 g, 1.81 mmol) was dissolved in 50 ml of 1,2-dichloroethane, and then 0.17 ml (3.80 mmol) of fuming nitric acid was added dropwise thereto at 0° C., followed by stirring at room temperature for 20 minutes. After the reaction mixture was diluted with chloroform, a saturated aqueous solution of sodium bicarbonate was added thereto, and the organic layer was washed with an aqueous solution of sodium chloride and dried over magnesium sulfate. After evaporation of the solvent under reduced pressure, 40 ml of dimethylformamide and 600 mg of 10% Pd/C were added to the residue, followed by stirring at 60° C. for one hour in an atmosphere of hydrogen. Insoluble material was filtered off, and the filtrate was concentrated under reduced pressure. The residue was subjected to silica gel column chromatography (ethyl acetate/toluene=20/80) to give 130.8 mg (yield 13%) of an amine derivative.

FAB-MS (m/z): 567 (M+1)$^+$

The amine derivative (23.9 mg, 0.0422 mmol) was dissolved in 2 ml of chloroform, and then 9.2 µl (0.0660 mmol) of triethylamine and 87 µl (1.10 mmol) of ethyl isocyanate were added thereto, followed by stirring at room temperature for 2 days. Water, methanol, and chloroform were added to the reaction mixture to complete the reaction, and the mixture was extracted with chloroform. The organic layer was washed with an aqueous solution of sodium chloride and dried over sodium sulfate. After evaporation of the solvent under reduced pressure, the residue was subjected to silica gel column chromatography (chloroform/methanol= 98/2) to give 21.4 mg (yield 80%) of N,O-diacetylated Compound VI-1.

Substantially the same procedure as in Example 26 was repeated using 21.4 mg (0.0336 mmol) of N,O-diacetylated Compound VI-1 to give 17.0 mg (yield 91%) of Compound VI-1.

1H-NMR (DMSO-d$_6$) δ (ppm): 1.129 (3H, t, J=7.1 Hz), 2.086 (3H, s), 2.110 (1H, dd, J=5.5, 14.3 Hz), 3.180 (2H, m), 3.237 (1H, dd, J=7.4, 14.3 Hz), 3.892 (3H, s), 4.984 (1H, d, J=17.0 Hz), 5.030 (1H, d, J=17.0 Hz), 6.359 (1H, s), 6.457 (1H, t, J=5.7 Hz), 7.157–7.230 (2H, m), 7.272 (1H, dd, J=5.5, 7.4 Hz), 7.344–8.058 (4H, m), 8.185 (1H, s), 8.616 (1H, s), 9.243 (1H, dd, J=1.3, 7.8 Hz)

FAB-MS (m/z): 554 (M+1)$^1$

EXAMPLE 31
Compound VI-2

Figure 24:
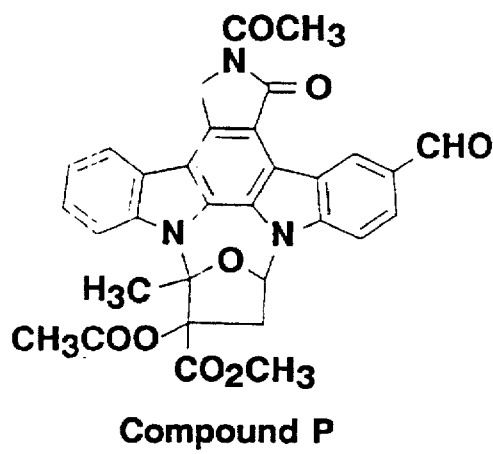
FIG. 24 is a diagram showing the structure of Compound P, Compound Q, and Compound R.
Figure 24:
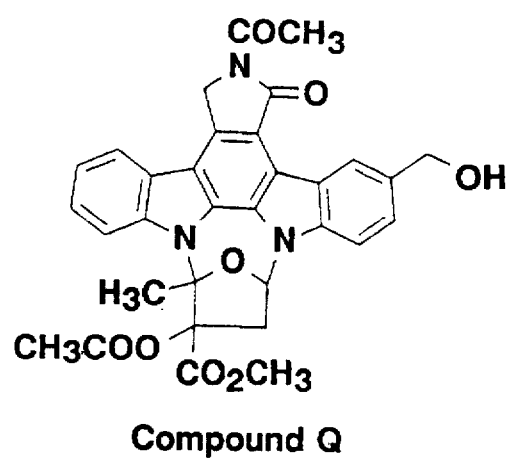
Figure 24:
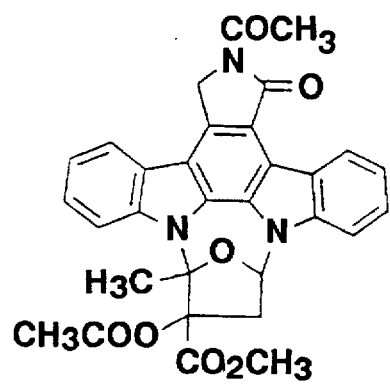

Substantially the same procedure as in Example 30 was repeated using 5 g (9.07 mmol) of Compound (R; FIG. 24) to give 259 mg (yield 5%) of a diamine derivative.

FAB-MS (m/z): 582 (M+1)$^+$

Substantially the same procedure as in Example 26 was repeated using 24.5 mg (0.0422 mmol) of the diamine derivative to give 3.8 mg (yield 18%) of Compound VI-2.

$^1$H-NMR (DMSO-d$_6$) δ (ppm): 1.952 (1H, dd, J=5.4, 13.9 Hz), 2.062 (3H, s), 3.894 (3H, s), 4.818–5.339 (6H, m), 6.198 (1H, s), 6.826–7.207 (4H, m), 7.507 (1H, dd, J=5.4, 7.3 Hz), 7.630 (1H, d, J=8.8 Hz), 8.443 (1H, s), 8.770 (1H, dd, J=1.2, 7.8 Hz)

FAB-MS (m/z): 498 (M+1)$^+$

EXAMPLE 32
Compound IV-6

Figure 25:
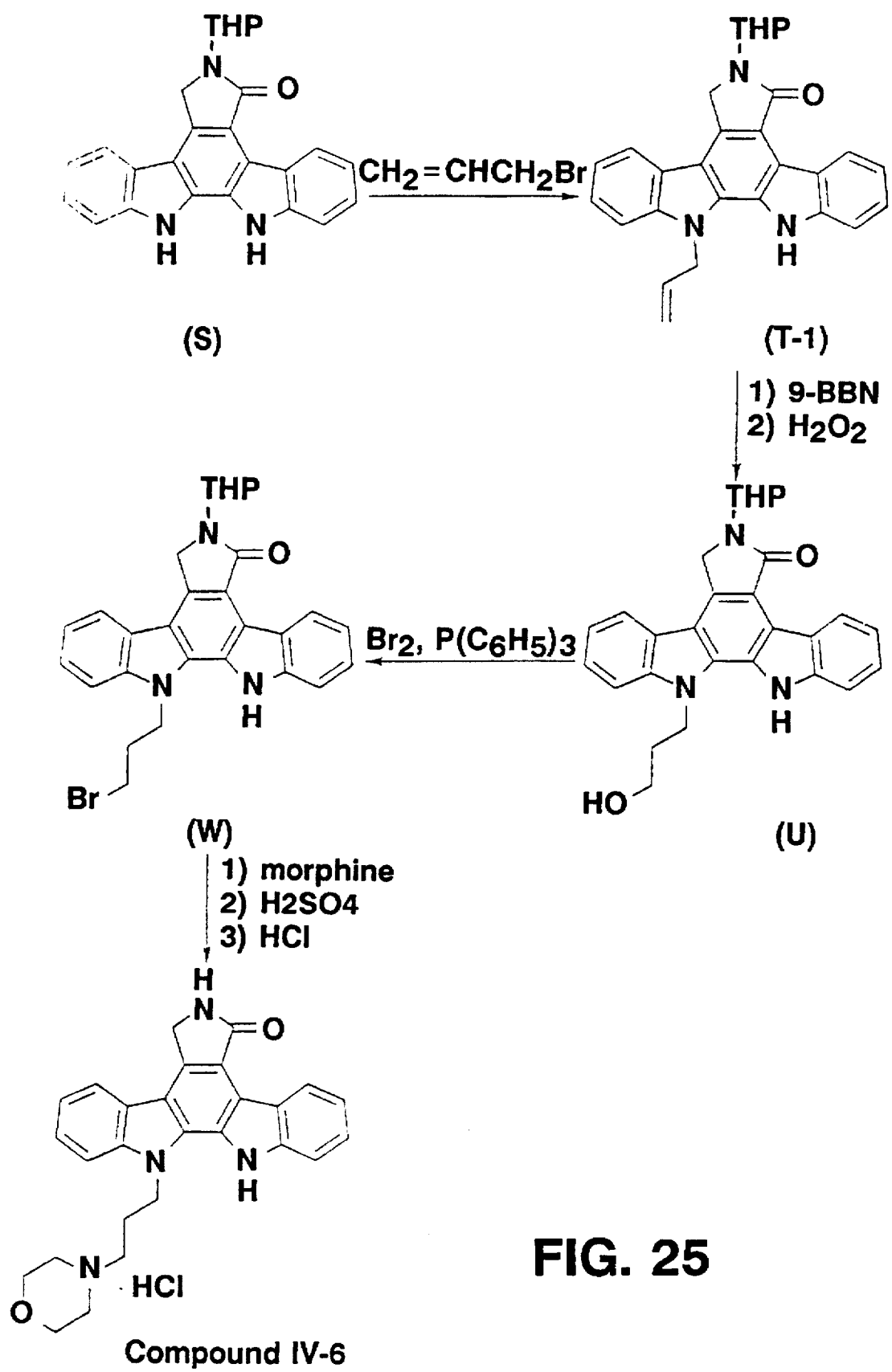
FIG. 25 is a diagram showing the synthesis of Compound IV-6 from starting Compound S.
Figure 26:
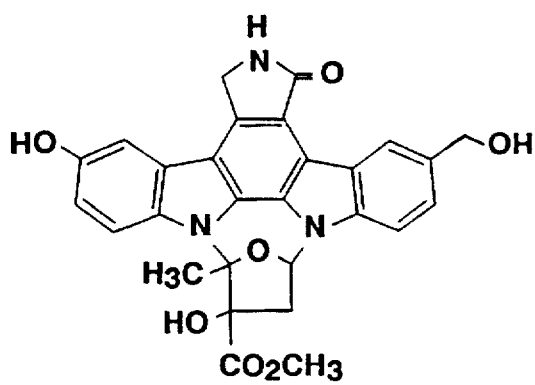
FIG. 26 is a diagram showing the chemical structure of compounds (AA), (BB), (CC), (DD) and (EE).
Figure 26:
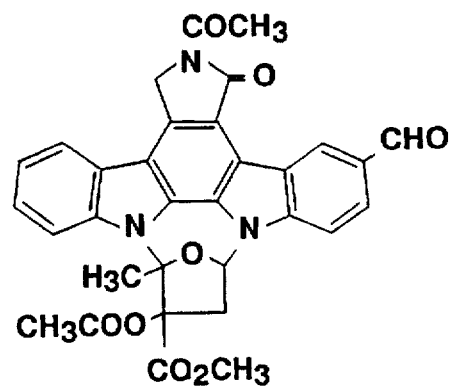
Figure 26:
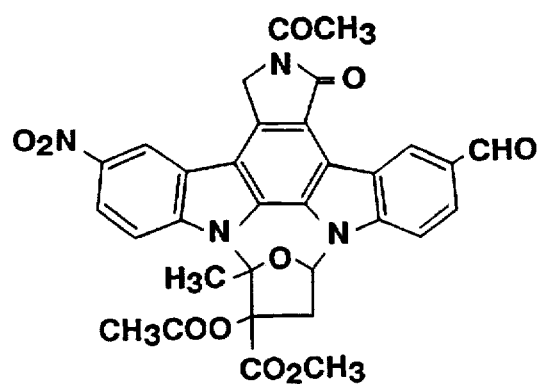
Figure 26:
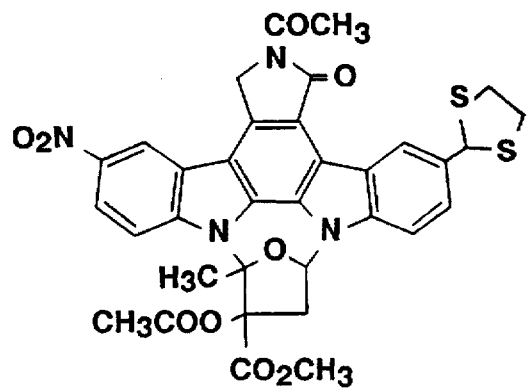
Figure 26:
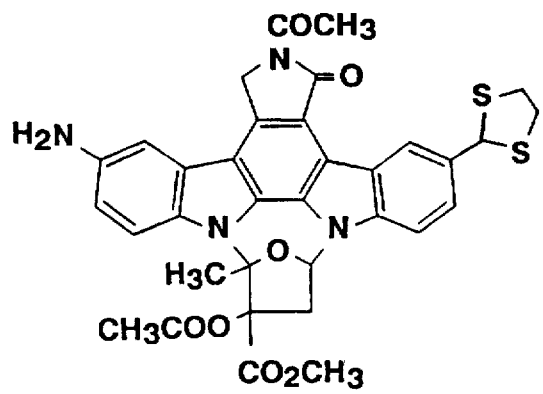
Figure 27:
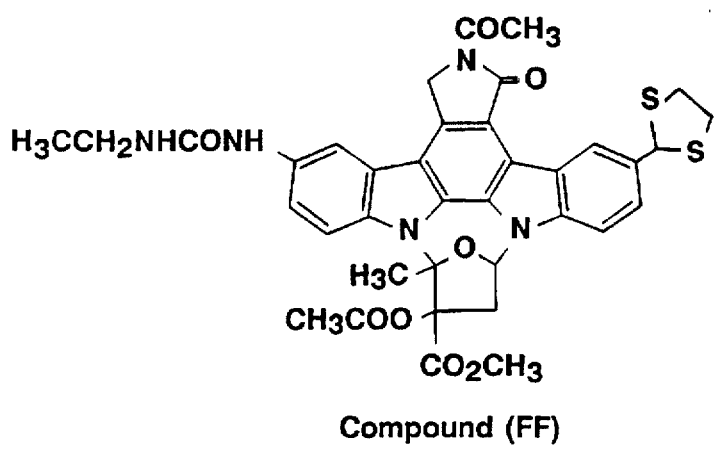
FIG. 27 is a diagram showing the chemical structure of compounds (FF), (GG), (HH) and (JJ).
Figure 27:
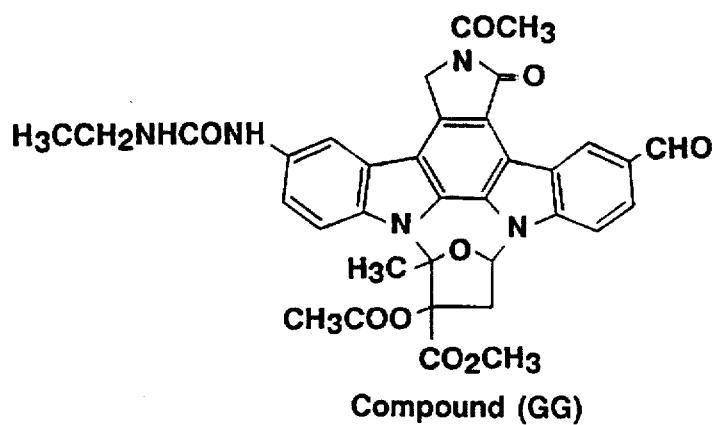
Figure 27:
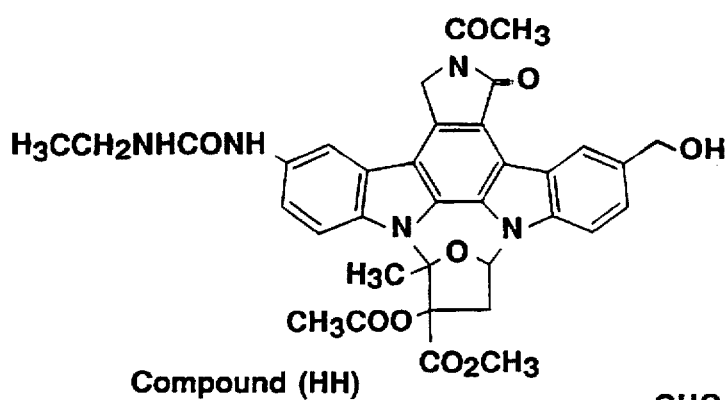
Figure 27:
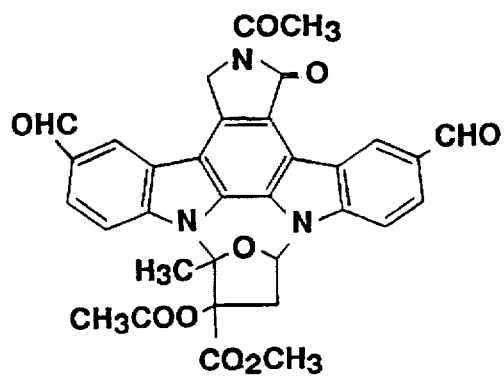

Compound (S; FIG. 25) [J. Chem. Soc. Perkin. Trans. 1, 2475 (1990)] (5.15 g, 13.0 mmol) was dissolved in a mixture of 30 ml of dimethylformamide and 60 ml of toluene, and then 1.45 g (12.9 mmol) of potassium tert-butoxide was added thereto at −20° C. in a atmosphere of argon, followed by stirring at room temperature for 30 minutes. After cooling the reaction mixture to −20° C., 1.12 ml (12.9 mmol) of allyl bromide was added thereto and the mixture was stirred at 0° C. for 2 hours. The solvent was evaporated under reduced pressure, and water was added to the residue, followed by extraction with tetrahydrofuran. The organic layer was washed with an aqueous solution of sodium chloride, and dried over magnesium sulfate. After evaporation of the solvent, the residue was subjected to silica gel column chromatography (ethyl acetate/toluene=1/15), and triturated with dichloromethane to give 898.4 mg (yield 16%) of Compound (T-1) as a single regioisomer.

$^1$H-NMR (DMSO-d$_6$) δ (ppm): 1.56–1.61 (2H, m), 1.73–1.87 (2H, m), 2.00–2.14 (2H, m), 3.63–3.69 (1H, m), 3.99–4.02 (1H, m), 4.747 (1H, dd, J=1.5, 17.1 Hz), 5.053 (1H, dd, J=1.5, 10.4 Hz), 5.084 (1H, d, J=17.3 Hz), 5.138 (1H, d, J=17.3Hz), 5.462 (1H, dd, J=2.0, 11.0 Hz), 5.593 (2H, d, J=4.6Hz), 6.178 (1H, ddt, J=4.6, 10.4 17.1 Hz), 7.242 (1H, ddd, J=0.9, 7.0,7.9 Hz), 7.368 (1H, dd, J=7.2, 7.8 Hz), 7.455 (1H, ddd, J=1.2, 7.0, 8.2 Hz), 7.542 (1H, ddd, J=1.1, 7.2, 8.3 Hz), 7.711 (1H, dd, J=0.9, 8.2 Hz), 7.762 (1H, d, J=8.3 Hz), 8.177 (1H, d, J=7.8 Hz), 9.305 (1H, d, J=7.9 Hz), 11.573 (1H, s)

FAB-MS (m/z): 436 (M+1)$^+$

Compound (T-1) (1.44 g, 3.30 mmol) was dissolved in 50 ml of tetrahydrofuran, and then 4.05 g (33.2 mmol) of 9-borabicyclo[3,3,1]nonane (9-BBN) (dimer) was added thereto, followed by stirring at room temperature for 3 hours in an atmosphere of argon. After cooling the reaction mixture to 0° C., 6 ml of 1N sodium hydroxide and 6 ml of a 35% aqueous solution of hydrogen peroxide were added thereto, followed by stirring for 45 minutes. After dilution of he reaction mixture with water, the mixture was extracted with ethyl acetate. The organic layer was washed successively with water and an aqueous solution of sodium chloride, and dried over magnesium sulfate. The solvent was evaporated under reduced pressure, and the residue was subjected to silica gel column chromatography (chloroform/methanol=100/1) to give 875.5 mg (yield 58%) of Compound (J-1).

$^1$H-NMR (DMSO-d$_6$) δ (ppm): 1.5–1.6 (2H, brm), 1.7–1.9 (2H, brm), 2.0–2.2 (2H, brm), 2.08–2.14 (2H, m), 3.49–3.53 (2H, m), 3.62–3.68 (1H, m), 3.99–4.02 (1H, m), 4.962 (2H, t, J=6.9 Hz), 5.072 (1H, d, J=17.2 Hz), 5.081 (1H, t, J=4.7 Hz), 5.123 (1H, d, J=17.2 Hz), 5.458 (1H, dd, J=2.0, 11.0 Hz), 7.251 (1H, ddd, J=0.9,7.0, 7.9 Hz)7.358 (1H, dd, J=7.2, 7.8 Hz), 7.463 (1H, ddd, J=1.2, 7.0, 8.2 Hz), 7.555 (1H, ddd, J=1.1, 7.2, 8.3 Hz), 7.696 (1H, d, J=8.2 Hz), 7.825 (1H, d, J=8.3 Hz), 8.162 (1H, d, J=7.8 Hz), 9.311 (1H, d, J=7.9 Hz), 11.684 (1H, s)

FAB-MS (m/z): 454 (M+1)$^+$

Compound (U-1) (178.5 mg, 0.394 mmol) was dissolved in 10 ml of dimethylformamide, and then 309.5 mg (1.18 mmol) of triphenylphosphine and 0.060 ml (1.2 mmol) of bromine were added thereto at 0° C. under an atmosphere of argon, followed by stirring at room temperature for 3 hours. After water was added to the reaction mixture to complete the reaction, the mixture was extracted with ethyl acetate, and the organic layer was washed successively with water and an aqueous solution of sodium chloride, and dried over magnesium sulfate. After evaporation of the solvent, the residue was subjected to silica gel column chromatography (ethyl acetate/toluene=1/8) to give 134.6 mg (yield 66%) of Compound (W).

$^1$H-NMR (CDCl$_3$) δ (ppm): 1.68–2.10 (6H, m), 2.13–2.18 (2H, m), 3.542 (2H, t, J=5.7 Hz), 3.80–3.86 (1H, m), 4.14–4.20 (1H, m), 4.658 (2H, t, J=7.5 Hz), 4.674 (1H, d,J=16.6 Hz), 4.830 (1H, d, J=16.6 Hz), 5.611 (1H, dd, J=2.5, 10.6 Hz), 7.13–7.52 (6H, m), 7.746 (1H, d J=7.6 Hz), 8.884 (1H, s), 9.294 (1H, d, J=8.0 Hz)

FAB-MS (m/z): 516 (M+1)$^+$

Compound (W) was dissolved in 5 ml of dimethylformamide, and then 0.045 ml (0.52 mmol) of morpholine was added thereto, followed by stirring at 80° C. for 3 hours in an atmosphere of argon. After cooling the reaction mixture to room temperature, ice-water was added thereto, and the formed precipitates were collected by filtration. The precipitates were dried under reduced pressure, and subjected to thin layer chromatography (chloroform/methanol=25/1). The product obtained was dissolved in 10 ml of tetrahydrofuran, and then 8 ml of 4N sulfuric acid was added thereto, followed by stirring at 60° C. for 12 hours. After cooling the reaction mixture to room temperature, ice was added thereto, and the mixture was extracted with ethyl acetate. The organic layer was washed successively with water and an aqueous solution of sodium chloride, and dried over magnesium sulfate. The solvent was evaporated under reduced pressure, and the residue was subjected to silica gel column chromatography (ethyl acetate/toluene=1/2). The product obtained was dissolved in a mixture of chloroform and ethyl acetate, and then 0.88N hydrochloric acid in ethyl acetate was added, followed by stirring at room temperature for one hour. The formed precipitates were collected by filtration, washed with ethyl acetate, and dried under reduced pressure to give 35.0 mg (yield 19%) of Compound (IV-6).

$^1$H-NMR (DMSO-d$_6$) δ (ppm): 2.29–2.34 (2H, m), 2.96–3.04 (2H, m), 3.30–3.40 (4H, m), 3.66–3.72 (2H, m), 3.56–3.90 (2H, m), 4.972 (2H, s), 5.093 (2H, t, J=7.1 Hz), 7.245 (1H, ddd, J=0.9, 7.0, 7.9 Hz), 7.370 (1H, dd, J=7.0, 7.9 Hz), 7.458 (1H, ddd, J=1.2, 7.0, 8.2 Hz), 7.565 (1H, ddd, J=1.2, 7.0, 8.2 Hz), 7.799 (1H, d, J=8.2 Hz), 7.884 (1H, d, J=8.2 Hz)8.071 (1H, d, J=7.9 Hz), 8.516 (1H, s), 9.345 (1H, d, J=7.9 Hz), 10.4–10.6 (1H, brs), 11.823 (1H, s)

FAB-MS (m/z): 439 (M+1)$^+$

EXAMPLE 33

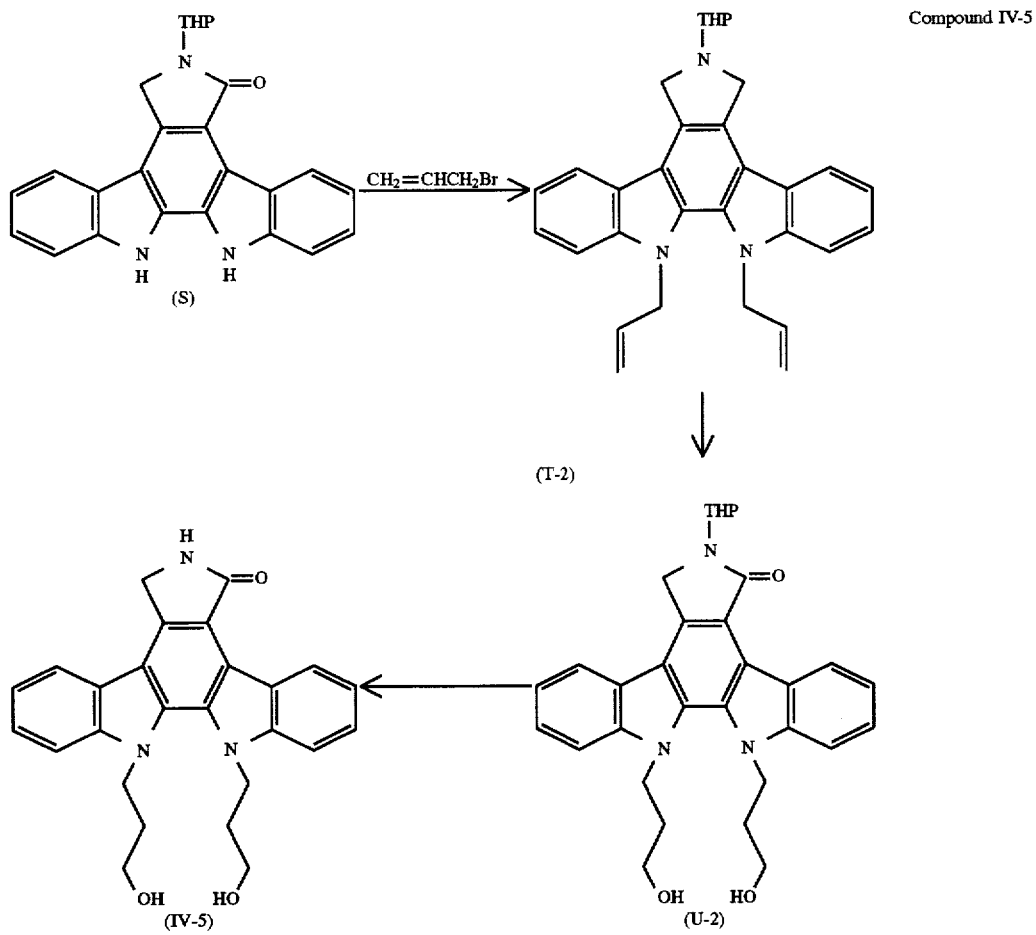

Compound (S) (*J. Chem. Soc. Perkin Trans.* 1:2475 1990) (823.7 mg, 2.083 mmol) was dissolved in 20 ml of dimethylformamide, and 166.4 mg (4.16 mmol) of sodium hydride (60%) was added thereto under ice cooling, followed by stirring at the same temperature for 10 minutes. Allyl bromide (0.45 ml, 5.2 mmol) was added thereto and the solution was stirred for 2 hours under ice cooling. After dilution with chloroform, water was added thereto and the organic layer was separated, washed with a saline solution, and dried over magnesium sulfate. After evaporation of the solvent, the residue was subjected to silica gel column chromatography (ethyl acetate/toluene=1/15) to give 735.0 mg (yield 74%) of Compound (T-2).

$^1$H-NMR (DMSO-d$_6$) δ (ppm): 1.563–2.154(6H, m), 3.657(1H, m), 4.008(1H, m), 5.044–5.478(11H, m), 6.153 (2H, m), 7.240–7.640(6H, m), 8.167(1H, d, J=7.8 Hz), 9.415(1H, d, J=7.8 Hz)

FAB-MS (m/z): 476 (M+1)$^+$

Sodium borohydride (77.7 mg, 2.05 mmol) was suspended in 20 ml of tetrahydrofuran, and 231.0 mg (1.82 mmol) of iodine was added thereto at 0° C. in an atmosphere of argon, followed by stirring at the same temperature for 15 minutes. Compound (T-2) (136.7 mg, 0.287 mmol) was added thereto at the same temperature and the mixture was stirred at room temperature for 4.5 hours. After the reaction mixture was cooled to 0° C., 3.7 ml of 1N sodium hydroxide and 3.7 ml of a 35% aqueous solution of hydrogen peroxide were added thereto, followed by stirring for a further 30 minutes. The reaction mixture was diluted with water and extracted with ethyl acetate. The ethyl acetate layer was washed successively with water and a saline solution, and dried over magnesium sulfate. After evaporation of the solvent, the residue was subjected to silica gel column chromatography (chloroform/methanol=15/1) to give 88.9 mg (yield 61%) of Compound (U-2).

$^1$H-NMR (CDCl$_3$) δ (ppm): 1.60–2.11(10H, m), 3.129 (2H, t, J=5.9 Hz), 3.192(2H, t, J=5.9 Hz), 3.798(1H, dt, J=2.8, 11.7 Hz), 4.09–4.15(1H, m), 4.723(2H, t, J=7.2 Hz), 4.807(2H, t, J=7.2 Hz), 4.943(1H, d, J=16.6 Hz), 5.107(1H, d, J=16.6 Hz), 5.652(1H, dd, J=2.4, 10.5 Hz), 7.15–7.18(1H, m), 7.318(1H, ddd, J=1.1, 7.0, 8.0 Hz), 7.35–7.39(1H, m), 7.461(1H, ddd, J=1.2, 6.8, 8.0 Hz), 7.519(1H, dd, J=1.0, 8.0 Hz), 7.610(1H, d, J=8.0 Hz), 7.951(1H, d, J=8.0 Hz), 9.490(1H, d, J=8.0 Hz)

FAB-MS (m/z): 512 (M+1)$^+$

Compound (U-2) (88.9 mg, 0.174 mmol) was dissolved in 10 ml of tetrahydrofuran, and 8 ml of 4N sulfuric acid was added thereto, followed by stirring at 60° C. for 24 hours. After the reaction mixture was cooled to room temperature, ice was added thereto, followed by extraction with ethyl acetate. The ethyl acetate layer was washed successively with water and a saline solution, and dried over magnesium sulfate. After evaporation of the solvent, the residue was subjected to thin layer chromatography (chloroform/methanol=15/1) to give 37.6 mg (yield 51%) of Compound IV-5.

¹H-NMR (DMSO-d₆) δ (ppm): 1.59–1.65(2H, m), 1.70–1.82(2H, m), 3.03–3.27(2H, m), 3.09–3.14(2H, m), 4.371(1H, t, J=5.0 Hz), 4.419(1H, t, J=5.0 Hz), 4.780(2H, t, J=7.3 Hz), 4.818(2H, t, J=7.4 Hz), 4.972(2H, s), 7.288(1H, ddd, J=0.8, 7.0, 7.8 Hz), 7.370(1H, t, J=7.2 Hz), 7.501(1H, ddd, J=1.2, 7.0, 8.2 Hz), 7.563(1H, ddd, J=1.1, 7.2, 8.3 Hz), 7.779(1H, d, J=8.3 Hz), 7.848(1H, d, J=8.2 Hz), 8.043(1H, d, J=7.2 Hz), 9.412(1H, dd, J=0.8, 7.8 Hz)

FAB-MS (m/z): 428 (M+1)⁺

EXAMPLE 34
Compound II-68

Compound (Q) (50.1 mg, 0.0862 mmol) was dissolved in 3 ml of chloroform, and then 129.5 mg (0.862 mmol) of 2-mercaptobenzimidazole and 49 mg (0.21 mmol) of (±)-10-camphorsulfonic acid were added thereto, followed by stirring at room temperature for 12 hours. The reaction mixture was washed successively with a saturated aqueous solution of sodium bicarbonate, water, and a saline solution, and dried over sodium sulfate. After evaporation of the solvent, the residue was subjected to preparative thin layer chromatography (chloroform/methanol=99/1) to give 46 mg (yield 75%) of N,O-diacetylated Compound II-68.

FAB-MS (m/z): 714 (M+1)⁺

Substantially the same procedure as in Example 25 was repeated using 33.4 mg (0.0468 mmol) of N,O-diacetylated Compound II-68 to give 17.5 mg (yield 59%) of Compound II-68.

¹H-NMR (DMSO-d₆) δ (ppm): 2.995 (1H, dd, J=4.9, 14.1 Hz), 2.139 (3H, s), 3.914 (3H, s), 4.799 (2H, s), 4.979 (1H, d, J=17.3 Hz), 5.028 (1H, d, J=17.3 Hz), 6.342 (1H, s), 7.101 (1H, dd, J=4.9, 7.3 Hz), 7.123–8.056 (10H, m), 8.617 (1H, s), 9.278 (1H, m)

FAB-MS (m/z): 630 (M+1)⁺

EXAMPLE 35
Compound II-69

Substantially the same procedure as in Example 25 was followed using 50 mg (0.0861 mmol) of Compound Q and 0.0868 ml (0.861 mmol) of furfurylmercaptan to give 36.0 mg (yield 62%) of N,O-diacetylated Compound II-69.

FAB-MS (m/z): 678 (M+1)⁺

Substantially the same procedure as in Example 25 was repeated using 22.7 mg (0.0335 mmol) of N,O-diacetylated Compound II-69 to give 17.7 mg (yield 89%) of Compound II-69.

¹H-NMR (CDCl₃) δ (ppm): 2.209(3H, s)2.607(1H, dd, J=4.9, 14.5 Hz), 3.401(1H, dd, J=7.5, 14.5 Hz), 3.671(2H, s), 3.857(2H, s), 4.103(3H, s), 4.532(1H, brs), 4.789(1H, d, J=16.1 Hz), 4.873(1H, d, J=16.1 Hz), 5.690(1H, s), 6.378 (1H, dd, J=1.9, 3.2 Hz), 6.416(1H, dd, J=0.6, 3.2 Hz), 6.846(1H, dd, J=4.8, 7.5 Hz), 7.334–7.932(7H, m), 8.961 (1H, m)

FAB-MS (m/z): 593 (M)⁺

EXAMPLE 36
Compound II-70

Compound (P) (100 mg, 0.173 mmol) was dissolved in 4 ml of chloroform, and then 34.0 mg (0.277 mmol) of 1-aminopyrrolidine hydrochloride was added thereto, followed by stirring at room temperature for 4 hours. After evaporation of the solvent under reduced pressure, the residue was subjected to silica gel column chromatography (chloroform/methanol=99/1) to give 100.5 mg (yield 90%) of N,O-diacetylated Compound II-70.

FAB-MS (m/z): 648 (M+1)⁺

Substantially the same procedure as in Example 25 was repeated using 40 mg (0.0618 mmol) of N,O-diacetylated Compound II-70 to give 30 mg (yield 86%) of Compound II-70.

H-NMR (DMSO-d₆ δ (ppm): 1.910–1.937(4H, m), 2.031 (1H, dd, J=4.9, 14.1 Hz), 2.142(3H, s), 2.329–2.635(4H, m), 3.395(1H, dd, J=7.3, 14.1 Hz), 3.925(3H, s), 4.981(1H, d, J=17.0 Hz), 5.030(1H, d, J=17.0 Hz), 7.110(1H, dd, J=4.9, 7.3 Hz), 7.345–8.057(6H, m), 7.425(1H, s), 8.596(1H, s), 9.210(1H, d, J=1.4 Hz)

FAB-MS (m/z): 564 (M+1)⁺

EXAMPLE 37
Compound II-71

Compound (P) (49 mg, 0.0846 mmol) was dissolved in 3 ml of chloroform, and then a solution of 15.8 mg (0.145 mmol) of 2-hydrazinopyridine in chloroform and 49 mg (0.21 mmol) of (±)-10-camphorsulfonic acid were added thereto, followed by stirring at room temperature for 12 hours. The reaction mixture was washed successively with a saturated aqueous solution of sodium bicarbonate, water, and a saline solution, and dried over sodium sulfate. After evaporation of the solvent, the residue was subjected to preparative thin layer chromatography (chloroform/methanol=99/1) to give 35.8 mg (yield 64%) of N,O-diacetylated Compound II-71.

FAB-MS (m/z): 671 (M+1)⁺

Substantially the same procedure as in Example 25 was repeated using 24.6 mg (0.0367 mmol) of N,O-diacetylated Compound II-71 to give 11.8 mg (yield 55%) of Compound II-71.

¹H-NMR (DMSO-d₆) δ (ppm): 2.039 (1H, dd, J=5.0, 13.9 Hz), 2.153 (3H, s), 3.418 (1H, dd, J=7.2, 13.9 Hz), 3.933 (3H, s), 5.001 (1H, d, J=17.5 Hz), 5.057 (1H, d, J=17.5 Hz), 6.366 (1H, s), 6.748 (1H, m), 7.164 (1H, dd, J=5.0, 7.2 Hz), 7.301–8.120 (9H, m), 8.242 (1H, s), 8.656 (1H, s), 8.656 (1H, s), 9.368 (1H, s), 10.738 (1H, s)

FAB-MS (m/z): 587 (M+1)⁺

EXAMPLE 38
Compound II-73

Substantially the same procedure as in Example 25 was followed using 30 mg (0.0516 mmol) of Compound (Q) and 52.2 mg (0.516 mmol) of 1H-1,2,4-triazole-3-thiol to give 31.4 mg (yield 92%) of N,O-diacetylated Compound II-73.

FAB-MS (m/z): 665 (M+1)⁺

Substantially the same procedure as in Example 25 was repeated using 15 mg (0.0226 mmol) of N,O-diacetylated Compound II-73 to give crude Compound II-73. Chloroform/methanol (90/10) was added thereto, followed by stirring to give 10.9 mg (yield 83%) of Compound II-73 as a precipitate.

¹H-NMR (DMSO-d₆) δ (ppm): 2.006(1H, dd, J=4.9, 13.9 Hz), 2.144(3H, s), 3.375(1H, dd, J=7.3, 13.9 Hz), 3.921 (3H, s), 4.559(2H, brs), 4.977(1H, d, J=17.4 Hz), 5.033(1H, d, J=17.4 Hz), 6.332(1H, s), 7.106(1H, dd, J=4.9, 7.3 Hz), 7.341–8.062(6H, m), 8.614(1H, s), 9.202(1H, d, J=1.5 Hz)

FAB-MS (m/z): 581 (M+1)⁺

EXAMPLE 39
Compound II-74

Compound (P) (97.5 mg, 0.168 mmol) was dissolved in 4 ml of tetrahydrofuran, and then an aqueous solution of 25.1 mg (0.0950 mmol) of aminoguanidine sulfate was added thereto, followed by stirring at room temperature for 3 hours. Ethyl acetate was added thereto, followed by stirring, and the insoluble matters were collected by filtration and subjected to silica gel column chromatography (chloroform/methanol=85/15) to give 87.1 mg (yield 82%) of N,O-diacetylated Compound II-74.

FAB-MS (m/z): 636 (M+1)⁺

Substantially the same procedure as in Example 25 was repeated using 69.6 mg (0.110 mmol) of N,O-diacetylated Compound II-74 to give 37.2 mg (yield 62%) of Compound II-74.

¹H-NMR (DMSO-d₆) δ (ppm): 2.046(1H, dd, J=4.9, 14.2 Hz), 2.148(3H, s), 3.406(1H, dd, J=7.5, 14.2 Hz), 3.929 (3H, s), 4.988(1H, d, J=17.3 Hz), 5.045(1H, d, J=17.3 Hz), 5.637–6.129(4H, m), 6.350(1H, s), 7.156(1H, dd, J=4.9, 7.5 Hz), 7.345–8.092(6H, m), 8.206 (1H, s), 8.603(1H, s), 9.271(1H, d, J=1.7 Hz)

FAB-MS (m/z): 552(M+1)⁺

EXAMPLE 40

Compound II-76

Compound (P) (103.8 mg, 0.179 mmol) was dissolved in a mixture of 6 ml of chloroform and 3 ml of methanol, and then 0.5 ml of an aqueous solution of 0.020 ml (0.207 mmol) of 4-aminomorpholine and 0.05 ml of 3N hydrochloric acid were added thereto, followed by stirring at room temperature for 3 hours. The reaction mixture was washed successively with a saturated aqueous solution of sodium bicarbonate and a saline solution, and dried over sodium sulfate. After evaporation of the solvent, the residue was subjected to silica gel column chromatography (chloroform/methanol =90/100) to give 82.8 mg (yield 70%) of N,O-diacetylated Compound II-76.

FAB-MS (m/z): 663 (M+1)⁺

Substantially the same procedure as in Example 25 was repeated using 50.6 mg (0.0763 mmol) of N,O-diacetylated Compound II-76 to give 36.4 mg (yield 82%) of Compound II-76.

¹H-NMR (DMSO-d₆) δ (ppm): 2.042(1H, dd, J=4.8, 14.3 Hz), 2.144(3H, s), 3.139–3.163(4H, m), 3.404(1H, dd, J=7.5, 14.3 Hz), 3.792–3.815(4H, m), 3.927(3H, s), 4.984 (1H, d, J=17.3 Hz), 5.040(1H, d, J=17.3 Hz), 6.352(1H, s), 7.132(1H, dd, J=4.8, 7.5 Hz), 7.344–8.065(6H, m), 7.897 (1H, s), 8.610(1H, s), 9.316(1H, d, J=1.7 Hz)

FAB-MS (m/z): 580 (M+1)⁺

EXAMPLE 41

Compound II-77

Substantially the same procedure as in Example 40 was followed using 100 mg (0.173 mmol) of Compound P and 16.7 mg (0.173 mmol) of 1,1-dimethylhydrazine hydrochloride to give 52.3 mg (yield 49%) of N,O-diacetylated Compound II-77.

FAB-MS (m/z): 622 (M+1)⁺

Substantially the same procedure as in Example 25 was repeated using 38.4 mg (0.0618 mmol) of N,O-diacetylated Compound I-75 to give 10.9 mg (yield 33%) of Compound I-75.

¹H-NMR (DMSO-d₆) δ (ppm): 2.037(1H, dd, J=5.0, 14.1 Hz), 2.142(3H, s), 2.939(6H, s), 3.399(1H, dd, J=7.5, 14.1 Hz), 3.926(3H, s), 4.981(1H, d, J=17.7 Hz), 5.037(1H, d, J=17.7 Hz), 6.342(1H, s), 7.118(1H, dd, J=5.0, 7.5 Hz), 7.342–8.063(6H, m), 7.533(1H, s), 8.601(1H, s), 9.258(1H, s)

FAB-MS (m/z): 538 (M+1)⁺

EXAMPLE 42

Compound II-78

Substantially the same procedure as in Example 40 was followed using 99.5 mg (0.172 mmol) of Compound (P) and 42.4 mg of 1-amino-4-methylpiperazine to give N,O-diacetylated Compound II-78.

Then, substantially the same procedure as in Example 25 was repeated using the above N,O-diacetylated Compound II-78 to give 19.4 mg [yield from Compound (P)19%] of Compound II-78.

¹H-NMR (DMSO-d₆) δ (ppm): 2.040(1H, dd, J=5.0, 14.0 Hz), 2.144(3H, s), 2.268(3H, s), 2.553(4H, m), 3.167(4H, m), 3.401(1H, dd, J=7.2, 14.0 Hz), 3.927(3H, s), 4.982(1H, d, J=17.1 Hz), 5.038(1H, d, J=17.1 Hz), 6.345(1H, s), 7.128(1H, dd, J=5.0, 7.2 Hz), 7.343–8.065(6H, m), 7.827 (1H, s), 8.609(1H, s), 9.299(1H, d, J=1.2 Hz)

FAB-MS (m/z) : 593 (M+1)⁺

EXAMPLE 43

Compound II-81

Compound (AA), a compound having bis (hydroxymethyl) in place of bis (dimethylaminoethylthiomethyl) of Compound II-80 (described in Example 28) (53.9 mg, 0.102 mmol) was dissolved in 2.5 ml of dichloromethane. Then, 0.18 ml (2.0 mmol) of 2-propanethiol and 0.03 ml (0.2 mmol) of trifluoroacetic anhydride were successively added thereto, followed by stirring at room temperature in an argon stream for 3 hours. A saturated aqueous solution of sodium bicarbonate was added to the reaction mixture, and the mixture was extracted with chloroform. The organic layer was washed with an aqueous solution of sodium chloride and dried over sodium sulfate. The solvent was evaporated under reduced pressure, and the residue was subjected to silica gel column chromatography (chloroform/methanol=99/1) to give 52.6 mg (yield 80%) of Compound II-81.

¹H-NMR (DMSO-d₆) δ (ppm): 1.259(3H, d, J=6.6 Hz), 1.266 (9H, d, J=6.6 Hz), 1.993(1H, dd, J=5.0, 14.1 Hz), 2.131(3H, s), 2.881(2H, m), 3.375(1H, dd, J=7.3, 14.1 Hz), 3.920(3H, s), 3.963(2H, s), 4.002(2H, s), 4.953(1H, d, J=17.1 Hz), 5.016(1H, d, J=17.1 Hz), 7.098(1H, dd, J=5.0, 7.3 Hz), 7.440–7.473(2H, m), 7.832(1H, d, J=8.1 Hz), 7.877(1H, d, J=8.8 Hz), 7.959(1H, d, J=1.7 Hz), 8.592(1H, s), 9.139(1H, d, J=1.2 Hz)

FAB-MS (m/z): 643(M)⁺, 644 (M+1)⁺

EXAMPLE 44

Compound II-82

Substantially the same procedure as in Example 43 was repeated using 51.9 mg (0.0958 mmol) of Compound (AA), 0.17 ml (1.9 mmol) of 1-propanethiol, and 0.03 ml (0.2 mmol) of trifluoroacetic anhydride to give 52.3 mg (yield 83%) of compound II-82.

¹H-NMR (DMSO-d₆ δ (ppm): 0.944(3H, t, J=7.3 Hz), 0.951 (3H, t, J=7.3 Hz), 1.557–1.656(4H, m), 1.995(1H, dd, J=4.8, 14.1 Hz), 2.132(3H, s), 2.462(2H, t, J=7.3 Hz), 2.470(2H, t, J=7.3 Hz), 3.378(1H, dd, J=7.4, 14.1 Hz), 3.921(3H, s), 3.957(2H, s), 4.951 (1H, d, J=17.1 Hz), 5.013(1H, d, 17.1 Hz), 7.102 (1H, dd, J=4.8, 7.4 Hz), 7.430–7.462(2H, m), 7.836(1H, d, J=8.3 Hz), 7.880(1H, d, J=8.6 Hz), 7.942(1H, d, J=1.5 Hz), 8.599(1H, s), 9.122(1H, d, J=1.5 Hz)

FAB-MS (m/z): 643 (M)⁺, 644 (M+1)⁺

Compound 45

Compound II-83

Substantially the same procedure as in Example 43 was repeated using 49.4 mg (0.0937 mmol) of Compound (AA), 0.20 ml (1.9 mmol) of 1-butanethiol, and 0.03 ml (0.2 mmol) of trifluoroacetic anhydride to give 51.7 mg (yield 82%) of Compound II-83.

¹H-NMR (DMSO-d₆) δ (ppm): 0.865(3H, t, J=7.4 Hz), 0.877 (3H, t, J=7.4 Hz), 1.328–1.409(4H, m), 1.535–1.600 (4H, m), 1.995(1H, dd, J=4.9, 14.1 Hz), 2.132(3H, s), 2.480(2H, t, J=7.4 Hz), 2.491(2H, t, J=7.4 Hz), 3.377(1H, dd, J=7.5, 14.1 Hz), 3.921(5H, s), 3.958 (2H, s), 4.952(1H, d, J=16.9 Hz), 4.997(1H, d, J=16.9 Hz), 6.314(1H, s), 7.101(1H, dd, J=4.9, 7.4 Hz), 7.432–7.458(2H, m), 7.834 (1H, d, J=8.4 Hz), 7.880(1H, d, J=8.7 Hz), 7.942(1H, d, J=1.5 Hz), 8.599 (1H, s), 9.123(1H, d, J=1.4 Hz)

FAB-MS (m/z): 671 (M)⁺

EXAMPLE 46

Compound II-84

Compound (AA) (45.3 mg, 0.0860 mmol) was dissolved in a mixture of 0.2 ml of methanol and 2 ml of chloroform, and then 20 mg (0.086 mmol) of camphorsulfonic acid was added thereto, followed by stirring at room temperature for 17 hours. A saturated aqueous solution of sodium bicarbonate was added to the reaction mixture, and the mixture was extracted with chloroform. The organic layer was washed with an aqueous solution of sodium chloride and dried over sodium sulfate. The solvent was evaporated under reduced pressure, and the residue was subjected to silica gel column chromatography (chloroform/methanol=99/1) to give 23.1 mg (yield 48%) of Compound II-84.

$^1$H-NMR (DMSO-$d_6$ δ (ppm): 2.010(1H, dd, J=4.9, 14.1 Hz), 2.142(3H, s), 3.341(3H, s), 3.364(3H, s), 3.383(1H, dd, J=7.4, 14.1 Hz), 3.925(3H, s), 4.583(2H, s), 4.622(2H, s), 4.982(1H, d, J=16.9 Hz), 5.033(1H, d, J=16.9 Hz), 6.330 (1H, s), 7.127(1H, dd, J=4.9, 7.4 Hz), 7.441–7.464(2H, m), 7.872(1H, d, J=8.4 Hz), 7.917(1H, d, J=8.7 Hz), 7.972(1H, d, J=1.1 Hz), 8.611 (1H, s), 9.165(1H, d, J=1.0 Hz)

FAB-MS (m/z): 555 (M)$^+$

EXAMPLE 47

Compound II-85

Substantially the same procedure as in Example 46 was repeated using a solution of 51.3 mg (0.0973 mmol) of Compound (AA) in a mixture of 0.2 ml of ethanol and 2 ml of chloroform to give 24.1 mg (yield 42%) of Compound II-85.

$^1$H-NMR (DMSO-$d_6$) δ (ppm): 1.189(3H, t, J=7.0 Hz), 1.199 (3H, t, J=7.0 Hz), 1.999(1H, dd, J=4.9, 14.1 Hz), 2.142(3H, s), 3.385(1H, dd, J=7.4, 14.1 Hz), 3.547 (2H, q, J=7.0 Hz), 3.563(2H, q, J=7.0 Hz), 3.925(3H, s), 4.622(2H, s), 4.661(2H, s), 4.980(1H, d, J=16.9 Hz), 5.032(1H, d, J=16.9 Hz), 6.325(1H, s), 7.124(1H, dd, J=4.9, 7.4 Hz), 7.447–7.467(2H, m), 7.864(1H, d, J=8.3 Hz), 7.911(1H, d, J=8.7 Hz), 8.602 (1H, s), 9.162(1H, d, J=1.0 Hz)

FAB-MS (m/z): 583 (M)$^+$

EXAMPLE 48

Compound II-86

Compound (BB) (Japanese Published Unexamined Patent Application No. 295588/88) (978 mg, 1.69 mmol) was dissolved in 70 ml of 1,2-dichloroethane, and then 0.17 ml (3.8 mmol) of fuming nitric acid was added dropwise thereto under ice-cooling, followed by stirring at room temperature for 30 minutes. The reaction mixture was diluted with chloroform and a saturated aqueous solution of sodium bicarbonate was added thereto. Insoluble material was collected by filtration and dried. The filtrate was washed with an aqueous solution of sodium chloride and dried over sodium sulfate, and the solvent was evaporated under reduced pressure. The residue and the insoluble material were combined to give 946 mg (yield 90%) of Compound (CC) as a crude product.

FAB-MS (m/z): 625 (M+1)$^+$

Compound (CC) (640 mg, 1.03 mmol) was dissolved in 30 ml of 1,2-dichloroethane, and then 0.3 ml (3.58 mmol) of 1,2-ethanedithiol and 0.2 ml (2.0 mmol) of boron trifluoride ether complex were added dropwise thereto at 0° C., followed by stirring for 30 minutes. A saturated aqueous solution of sodium bicarbonate was added to the reaction mixture, and the mixture was extracted with chloroform. The organic layer was washed with an aqueous solution of sodium chloride and dried over magnesium sulfate. The solvent was evaporated under reduced pressure, and the residue was subjected to silica gel column chromatography (chloroform) to give 579 mq (yield 81%) of Compound (DD).

FAB-MS (m/z): 701 (M+1)$^+$

Compound (DD) (579 mg, 0.827 mmol) was dissolved in 56 ml of N,N-dimethylformamide, and then 400 mg of palladium/carbon was added thereto, followed by stirring at 60° C. in an atmosphere of hydrogen for 2 hours. Insoluble material was filtered off and the solvent was evaporated under reduced pressure from the filtrate. The residue was subjected to silica gel column chromatography (chloroform/methanol=98/2) to give 193 mg (yield 35%) of Compound (EE).

FAB-MS (m/z): 671 (M+1)$^+$

Compound (EE) (193 mg, 0.288 mmol) was dissolved in 10 ml of chloroform, and then 0.1 ml (0.7 mmol) of triethylamine and 0.2 ml (2.5 mmol) of ethyl isocyanate were added thereto, followed by stirring at room temperature for 20 hours. After water was added, the mixture was extracted with chloroform. The organic layer was washed with an aqueous solution of sodium chloride and dried over magnesium sulfate. The solvent was evaporated under reduced pressure, and the residue was subjected to silica gel column chromatography (chloroform/methanol=96/4) to give 211 mg (yield 99%) of Compound (FF).

FAB-MS (m/z): 742 (M+1)$^+$

Compound (FF) (211 mg, 0.285 mmol) was dissolved in a mixture of 6 ml of ethanol and 6 ml of chloroform, and then 171 mg (1.01 mmol) of silver nitrate was added thereto at 50° C., followed by stirring for 20 minutes. After the completion of reaction, insoluble material was filtered off. The filtrate was washed with a saturated aqueous solution of sodium bicarbonate and an aqueous solution of sodium chloride, and dried over sodium sulfate. The solvent was evaporated under reduced pressure, and the residue was subjected to silica gel column chromatography (chloroform/methanol=97/3) to give 118 mg (yield 62%) of Compound (GG).

FAB-MS (m/z): 666 (M+1)$^+$

Compound (GG) (100 mg, 0.150 mmol) was dissolved in a mixture of 4.5 ml of chloroform and 0.72 ml of methanol, and then 8.7 mg (0.23 mmol) of sodium borohydride was added thereto at 0° C., followed by stirring for 45 minutes. The reaction mixture was poured into water and the mixture was extracted with chloroform. The organic layer was washed with an aqueous solution of sodium chloride and dried over sodium sulfate. The solvent was evaporated under reduced pressure, and the residue was subjected to silica gel column chromatography (chloroform/methanol=95/5) to give 101 mg (yield 100%) of Compound (HH).

FAB-MS (m/z): 668 (M+1)$^+$

Compound (HH) (21.7 mg, 0.0325 mmol) was dissolved in a mixture of 1 ml of 1,2-dichloroethane and 0.3 ml of methanol, and then 6 μl (0.03 mmol) of a 5.1N methanolic solution of sodium methoxide was added thereto, followed by stirring for one hour. The reaction mixture was poured into water and the mixture was extracted with a mixture of chloroform and methanol (9/1). The organic layer was washed with an aqueous solution of sodium chloride and dried over magnesium sulfate. The solvent was evaporated under reduced pressure, and the residue was subjected to silica gel column chromatography (chloroform/methanol= 90/10) to give 14.9 mg (yield 79%) of Compound II-86.

$^1$H-NMR (DMSO $d_6$) δ (ppm): 1.097(3H, t, J=7.2 Hz), 1.968 (1H, dd, J=4.9, 13.9 Hz), 2.113(3H, s), 3.170(2H, dq, J=5.6, 7.2 Hz), 3.359(1H, dd, J=7.3, 13.9 Hz), 3.915(3H, s), 4.664(2H, s), 4.887(1H, d, J=16.9 Hz), 4.947(1H, d, J=16.9 Hz), 6.081(1H, t, J=5.6 Hz), 6.273(1H, s), 7.090(1H, dd, J=4.9, 7.3 Hz), 7.364 (1H, dd, J=2.0, 9.0 Hz), 7.455(1H, dd, J=1.3, 8.5 Hz), 7.782(1H, d, J=9.0 Hz), 7.826(1H, d, J=8.5

Hz), 8.189(1H, d, J=2.0 Hz), 8.493(1H, s), 8.537(1H, s), 9.127(1H, d, J=1.3 Hz)

FAB-MS (m/z): 584 (M+1)$^+$

EXAMPLE 49
Compound II-87

Substantially the same procedure as in Example 43 was repeated using 29.8 mg (0.0511 mmol) of Compound II-86 and 0.14 ml (1.6 mmol) of ethanethiol to give 24.2 mg (yield 76%) of Compound II-87.

$^1$H-NMR (DMSO-d$_6$) δ (ppm): 1.097(3H, t, J=7.1 Hz), 1.230 (3H, t, J=7.3 Hz), 1.982(1H, dd, J=5.0, 14.1 Hz), 2.111(3H, s), 2.487(2H, dq, J=5.6, 7.1 Hz), 2.987 (2H, q, J=7.3 Hz), 3.362(1H, dd, J=7.5, 14.1 Hz), 3.914(3H, s), 3.939(2H, s), 4.888(1H, d, J=17.2 Hz), 4.950(1H, d, J=17.2 Hz), 6.083(1H, t, J=5.6 Hz), 6.285(1H, s), 7.083(1H, dd, J=5.0, 7.5 Hz), 7.370(1H, dd, J=2.1, 9.0 Hz), 7.436(1H, dd, J=1.6, 8.5 Hz), 7.783(1H, d, J=9.0 Hz), 7.825(1H, d, J=8.5 Hz), 8.188(1H, d, J=2.1 Hz), 8.496(1H, s), 8.532(1H, s), 9.116(1H, d, J=1.6 Hz)

FAB-MS(m/z): 627(M)$^+$

EXAMPLE 50
Compound II-88

Compound (AA) (50.4 mg, 0.0956 mmol) was dissolved in 0.7 ml of dichloromethane, and then 0.09 ml (0.56 mmol) of triethylsilane and 0.73 ml (9.5 mmol) of trifluoroacetic acid were successively added thereto under ice-cooling, followed by stirring at room temperature for 10 minutes. The reaction mixture was neutralized with a 1N aqueous solution of sodium hydroxide and the mixture was extracted with chloroform. The organic layer was washed with an aqueous solution of sodium chloride and dried over magnesium sulfate. The solvent was evaporated under reduced pressure, and the residue was subjected to silica gel column chromatography (chloroform/methanol=90/10) to give 20.7 mg (yield 44%) of Compound II-88.

$^1$H-NMR (DMSO-d$_6$ δ (ppm): 1.963(1H, dd, J=4.9, 13.9 Hz), 2.116(3H, s), 2.510(3H, s), 2.529(3H, s), 3.353(1H, dd, J=7.3, 13.9 Hz), 3.914(3H, s), 4.955(1H, d, J=17.2 Hz), 5.007(1H, d, J=17.2 Hz), 6.273(1H, s), 7.074(1H, dd, J=4.9, 7.3 Hz), 7.287-7.313(2H, m), 7.764(1H, d, J=8.3 Hz), 7.808(1H, d, J=8.5 Hz), 7.828(1H, s), 8.575(1H, s), 9.006 (1H, s)

FAB-MS (m/z): 496 (M+1)$^+$

EXAMPLE 51
Compound II-89

Compound (AA) (4.3 g, 8.16 mmol) was dissolved in 215 ml of dichloromethane, and then 12.1 ml (163 mmol) of ethanethiol and 2.5 ml (17.7 mmol) of trifluoroacetic anhydride were successively added thereto, followed by stirring at room temperature for 12 hours. A saturated aqueous solution of sodium bicarbonate was added to the reaction mixture, and the mixture was extracted with chloroform. The organic layer was washed with an aqueous solution of sodium chloride and dried over sodium sulfate. The solvent was evaporated under reduced pressure, and the residue was subjected to silica gel column chromatography (ethyl acetate/toluene=3/7) to give 4 mg (yield 0.08%) of Compound II-89.

$^1$H-NMR (DMSO-d$_6$) δ (ppm): 1.233(3H, t, J=7.3 Hz), 1.253 (3H, dd, J=7.6, 8.3 Hz), 2.007(1H, dd, J=4.6, 14.2 Hz), 2.139(3H, s), 2.492(2H, q, J=7.3 Hz), 2.622-2.710(1H, m), 2.788-2.877(1H, m), 3.384(1H, dd, J=7.4, 14.2 Hz), 3.926 (3H, s), 3.979(2H, s), 4.106(1H, d, J=12.9 Hz), 4.285(1H, d, J=12.9 Hz), 4.961(1H, d, J=17.9 Hz), 5.025(1H, d, J=17.9 Hz), 6.325(1H, s), 7.132(1H, dd, J=4.8, 7.4 Hz), 7.433-7.473(2H, m), 7.887(1H, d, J=8.6 Hz), 7.902(1H, d, J=8.3 Hz), 8.625(1H, s), 9.147(1H, s)

FAB-MS (m/z): 632 (M+1)$^+$

EXAMPLE 52
Compound II-90

Compound (JJ) (Japanese Published Unexamined Patent Application No. 295588/88) (18.5 g, 30.5 mmol) was dissolved in a mixture of 900 ml of chloroform and 145 ml of methanol, and then 3.42 g (90.4 mmol) of sodium borohydride was added thereto under ice-cooling, followed by stirring for 25 minutes. The reaction mixture was poured into ice water, and insoluble material was collected by filtration, washed with water, and dried under reduced pressure. The insoluble material was dissolved in a mixture of 555 ml of 1,2-dichloroethane and 185 ml of methanol, and then 0.925 ml (4.72 mmol) of a 5.1N methanolic solution of sodium methoxide was added thereto, followed by stirring for one hour and a half. The reaction mixture was poured into water, and insoluble material was collected by filtration, dried under reduced pressure, and subjected to silica gel column chromatography (chloroform/methanol=8/2) to give 0.350 g (yield 2.3%) of Compound II-90.

$^1$H-NMR (DMSO-d$_6$) δ (ppm): 1.909(1H, dd, J=4.9, 13.4 Hz), 2.148(3H, s), 3.134(1H, dd, J=7.3, 13.4 Hz), 3.757 (1H, dd, J=6.1, 11.3 Hz), 3.831(1H, dd, J=5.5, 11.3 Hz), 4.662 (2H, d, J=5.6 Hz), 4.704(2H, d, J=5.6 Hz), 4.944(1H, d, J=17.0 Hz), 5.007(1H, d, J=17.0 Hz), 5.098(1H, dd, J=5.5, 6.1 Hz), 5.123(1H, t, J=5.6 Hz), 5.189(1H, t, J=5.6 Hz), 5.346(1H, s), 6.942(1H, dd, J-4.9, 7.3 Hz), 7.398-7.459(2H, m), 7.722(1H, d, J=8.3 Hz), 7.911(1H, d, J=8.8 Hz), 7.952 (1H, d, J=0.97 Hz), 8.538(1H, s), 9.129(1H, m)

FAB-MS (m/z): 499 (M)$^+$, 500 (M+1)$^+$

EXAMPLE 53
Compound II-91

Compound (DD) (18.6 mg, 0.0266 mmol) was dissolved in a mixture of 1.5 ml of 1,2-dichloroethane and 0.5 ml of methanol, and then 5 μl (0.026 mmol) of a 5.1N methanolic solution of sodium methoxide was added thereto, followed by stirring for one hour. The reaction mixture was poured into water and the mixture was extracted with a mixture of chloroform and methanol (9/1). The organic layer was washed with an aqueous solution of sodium chloride and dried over magnesium sulfate. The solvent was evaporated under reduced pressure, and the residue was subjected to silica gel column chromatography (chloroform/methanol= 95/5) to give 7.0 mg (yield 43%) of Compound II-91.

$^1$H-NMR (DMSO-d$_6$) δ (ppm): 2.017(1H, dd, J=4.9, 14.4 Hz), 2.183(3H, s), 3.408-3.452(2H, m), 3.588-3.651(2H, m), 3.940(3H, s), 5.122(1H, d, J=18.1 Hz), 5.175(1H, d, J=18.1 Hz), 5.943(1H, s), 6.549(1H, s), 7.189(1H, dd, J=4.9, 7.3 Hz), 7.739(1H, dd, J=1.9, 8.7 Hz), 7.917(1H, d, J=8.7 Hz), 8.125(1H, d, J=9.4 Hz), 8.373(1H, dd, J=2.2, 9.4 Hz), 8.733(1H, s), 8.848(1H, d, J=2.2 Hz), 9.353(1H, d, J=1.9 Hz)

FAB-MS (m/z): 617 (M+1)$^+$

EXAMPLE 54
Compound II-92

Substantially the same procedure as in Example 53 was repeated using 23.3 mg (0.0314 mmol) of Compound (FF) to give 14.7 mg (yield 71%) of Compound II-92.

$^1$H-NMR (DMSO-d$_6$) δ (ppm): 1.097(3H, t, J=7.1 Hz), 1.98 (1H, dd, J=4.9, 14.0 Hz), 3.170(2H, dq, J=5.6, 12.7 Hz), 3.359(1H, dd, J=7.4, 14.0 Hz), 3.401-3.464 (2H, m), 3.582-3.645(2H, m), 3.914(3H, s), 4.891 (1H, d, J=17.6 Hz), 4.956 (1H, d, J=17.6 Hz), 5.930 (1H, s), 6.081(1H, t, J=5.6 Hz), 6.287(1H, s), 7.091 (1H, dd, J=4.9, 7.4 Hz), 7.379 (1H, dd, J=2.2, 9.0 Hz), 7.683(1H, dd, J=1.7, 8.5 Hz), 7.783(1H, d, J=9.0 Hz), 7.850(1H, d, J=8.5 Hz), 8.183(1H, d, J=2.2 Hz), 8.499(1H, s), 8.534(1H, s), 9.296(1H, d, J=1.7 Hz)

FAB-MS (m/z): 658 (M+1)$^+$

What is claimed is:

1. A method for enhancing the function of cholinergic, striatal, basal forebrain and sensory neurons in a mammal, said method comprising administering to said mammal a therapeutic amount of a composition of the formula —N(CH$_3$)—W—N(CH$_3$)— where represents a residue of the formula:

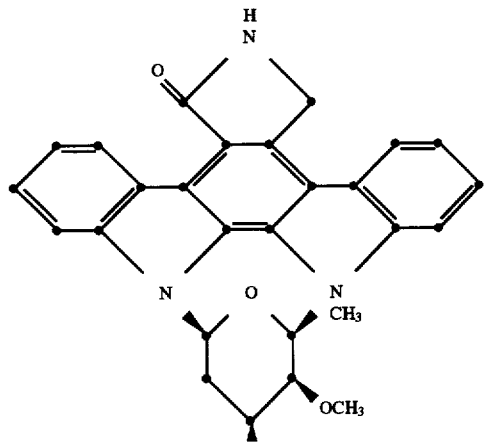

and W represents a radical of the formula —C(=Y)—NH—W$^1$—NH—C(=Y)—, where W$^1$ is a hydrocarbylene radical of 2 to 20 carbon atoms and Y is selected from the group consisting of O and S.

2. The method of claim 1, wherein said sensory neurons are dorsal root ganglion neurons.

3. A method for protecting nerve cells from degeneration induced by excitatory amino acids, said method comprising administering to a mammal a therapeutic amount of a composition of the formula —N(CH$_3$)—W—N(CH$_3$)— where represents a residue of the formula:

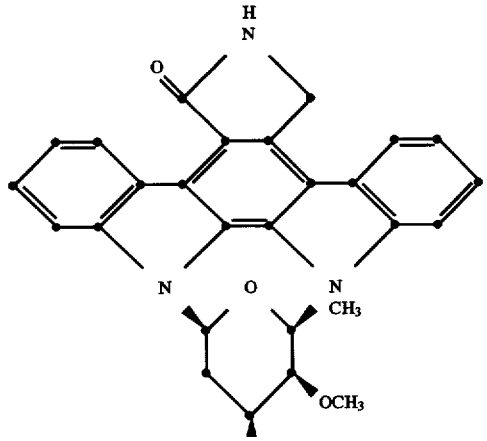

and W represents a radical of the formula —C(=Y)—NH—W$^1$—NH—C(=Y)—, where W$^1$ is a hydrocarbylene radical of 2 to 20 carbon atoms and Y is selected from the groups consisting of O and S.

4. The method of claim 3 wherein said degeneration is associated with Alzheimer's disease.

5. The method of claim 3 wherein said degeneration is associated with motor neuron disease.

6. The method of claim 5 wherein said motor neuron disease is amyotrophic lateral sclerosis.

7. The method of claim 3 wherein said degeneration is associated with Parkinson's disease.

8. The method of claim 3 wherein said degeneration is associated with cerebrovascular disease.

9. The method of claim 8 wherein said cerebrovascular disease is ischemic.

10. The method of claim 3 wherein said degeneration is associated with AIDS dementia.

11. The method of claim 3 wherein said degeneration is associated with epilepsy.

12. The method of claim 3 wherein said degeneration is associated with concussive injuries to the brain.

13. The method of claim 3 wherein said degeneration is associated with concussive injuries to the spinal cord.

14. The method of claim 3 wherein said degeneration is associated with penetrating injuries to the brain.

15. The method of claim 3 wherein said degeneration is associated with penetrating injuries to the spinal cord.

16. The method of claim 3, wherein said degeneration is associated with Huntington's disease.

17. A method for enhancing the function of a neuron in a mammal, wherein said neuron is selected from the group consisting of sensory, cholinergic, basal forebrain, and striatal neurons, said method comprising administering to said mammal a therapeutic amount of a compound represented by the formulae:

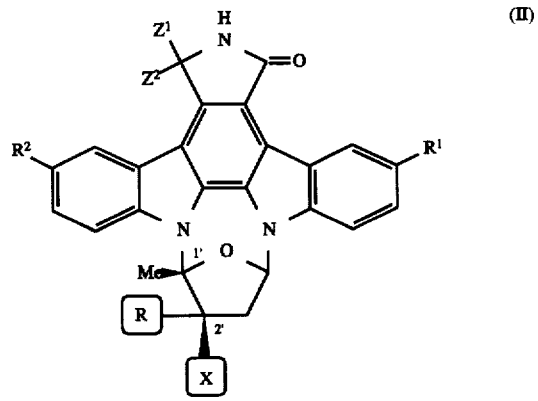

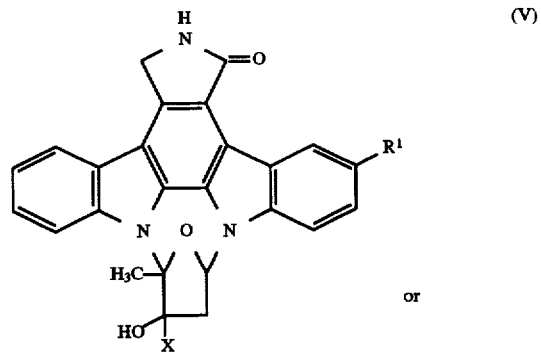

or

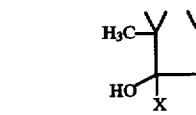

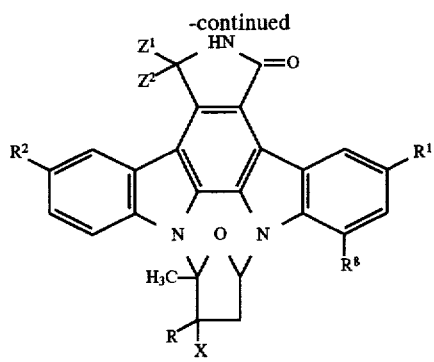

(VI)

wherein the following substitutions are made:

| Compound | R¹ | R² | X | R | Z² |
|---|---|---|---|---|---|
| II-1 | H | H | $CH_2N_3$ | OH | H |
| II-2 | $NHCONHC_6H_5$ | H | $CO_2CH_3$ | OH | H |
| II-3 | $CH_2SOC_2H_5$ | H | $CO_2CH_3$ | OH | H |
| II-4 | H | H | $CH_2OH$ | $OCH_3$ | H |
| II-5 | H | H | $CONHC_2H_5$ | OH | H |
| II-6 | H | H | $CH=NNH-\underset{H}{\underset{|}{\overset{N}{\underset{\diagdown}{\diagup}}}}\hspace{-2pt}\overset{\diagup\diagdown}{\underset{N}{}}$ | OH | H |
| II-7[2,7] | H | H | $CH_2NH-Gly$ | OH | H |
| II-8 | H | H | $CON(CH_3)_2$ | OH | H |
| II-9[3] | H | H | $-CH_2NHCO_2-$ | | H |
| II-10 | Br | H | $CO_2CH_3$ | OH | H |
| II-11 | H | H | $CONH_2$ | OH | H |
| II-12 | H | H | $CH_2OH$ | OH | H |
| II-13 | H | H | $CONHC_3H_7$ | OH | H |
| II-14[2] | H | H | $CH_2NH-Ser$ | OH | H |
| II-15 | H | H | $CH_2SOCH_3$ | OH | H |
| II-16 | H | H | $CH=NOH$ | OH | H |
| II-17 | H | H | CON O | OH | H |
| II-18[2,7] | H | H | $CH_2NH-Pro$ | OH | H |
| II-19 | H | H | $CH=NNHC(=NH)NH_2$ | OH | H |
| II-20 | Br | Br | $CO_2CH_3$ | OH | O |
| II-21 | H | H | $CONH(CH_2)_2OH$ | OH | H |
| II-22 | H | H | $CO_2CH_3$ | OH | O |
| II-23 | H | H | H | OH | H |
| II-24 | H | H | $CH=NNHCONH_2$ | OH | H |
| II-25 | H | H | $CH_2OCOCH_3$ | OH | H |
| II-26[3] | H | H | $-CH_2OC(CH_3)_2O-$ | | H |
| II-29 | $NHCONHC_2H_5$ | H | $CO_2CH_3$ | OH | H |
| II-30 | $CH_2SC_2H_5$ | H | $CO_2CH_3$ | OH | H |
| II-31 | Br | H | $CH_2OH$ | OH | H |
| II-32 | Br | Br | $CO_2CH_3$ | OH | H |
| II-33 | $CH_2SC_6H_5$ | H | $CO_2CH_3$ | OH | H |
| II-34 | Cl | Cl | $CO_2CH_3$ | OH | H |
| II-36 | H | H | $CONHC_6H_5$ | OH | H |
| II-37 | H | H | $CH_2SO-\underset{N}{\diagup\diagdown}$ | OH | H |
| II-38 | H | H | $CH_2NHCO_2C_6H_5$ | OH | H |
| II-39 | $NHCONHC_2H_5$ | $NHCONHC_2H_5$ | $CO_2CH_3$ | OH | H |
| II-40 | $N(CH_3)_2$ | H | $CO_2CH_3$ | OH | H |
| II-41 | $CH_3$ | H | $CO_2CH_3$ | OH | H |
| II-42 | $CH_2OCONHC_2H_5$ | H | $CO_2CH_3$ | OH | H |
| II-43 | $NHCO_2CH_3$ | H | $CO_2CH_3$ | OH | H |
| II-44 | Br | Br | $CH_2OH$ | OH | H |
| II-45 | Br | Br | $CONHC_6H_5$ | OH | H |
| II-46 | Br | Br | $CONHCH_2CH_2OH$ | OH | H |
| II-47 | $CH_2OC_2H_5$ | H | $CO_2CH_3$ | OH | H |
| II-48 | $CH_2N(CH_3)_2$ | H | $CO_2CH_3$ | OH | H |
| II-49 | $CH_2SO_2C_2H_5$ | H | $CO_2CH_3$ | OH | H |

-continued

| Compound | $R^1$ | $R^2$ | X | R | $Z^2$ |
|---|---|---|---|---|---|
| II-50 | 2-(CH₂S)-pyridine | H | $CO_2CH_3$ | OH | H |
| II-51 | $CH_2SC_2H_5$ | $CH_2SC_2H_5$ | $CO_2CH_3$ | OH | H |
| II-52 | CH=NNH—(4,5-dihydroimidazol-2-yl) | H | $CO_2CH_3$ | OH | H |
| II-53 | 2-(CH₂S)-pyrimidine | H | $CO_2CH_3$ | OH | H |
| II-54 | 2-(CH₂S(O))-pyridine | H | $CO_2CH_3$ | OH | H |
| II-55 | 2-(CH₂S(O))-pyrimidine | H | $CO_2CH_3$ | OH | H |
| II-56 | $CH_2SC_2H_5$ | $CH_2OH$ | $CO_2CH_3$ | OH | H |
| II-57 | H | H | $CH_2NHCO_2CH_3$ | OH | H |
| II-58 | Br | H | $CONH_2$ | OH | H |
| II-59 | H | H | $CH_2SC_6H_5$ | OH | H |
| II-60 | H | H | 2-(CH₂S)-pyridine | OH | H |
| II-61 | H | H | $CH_2SOC_6H_5$ | OH | H |
| II-63 | OH | H | $CO_2CH_3$ | OH | H |
| II-65 | $CH_2SCH_2CH_2N(CH_3)_2$ | H | $CO_2CH_3$ | OH | H |
| II-66 | H | H | $CH_2NH_2$ | OH | H |
| II-67 | H | H | $CONHCH_3$ | OH | H |
| II-68 | 2-(CH₂S)-benzimidazole | H | $CO_2CH_3$ | OH | H |
| II-69 | 2-(CH₂SCH₂)-furan | H | $CO_2CH_3$ | OH | H |
| II-70 | CH=N—N(pyrrolidine) | H | $CO_2CH_3$ | OH | H |
| II-71 | CH=NNH—(2-pyridyl) | H | $CO_2CH_3$ | OH | H |
| II-72 | $CH_2S(CH_2)_2NH_2$ | H | $CO_2CH_3$ | OH | H |
| II-73 | (CH₂S)-1,2,4-triazole | H | $CO_2CH_3$ | OH | H |

-continued

| Compound | R¹ | R² | X | R | Z² |
|---|---|---|---|---|---|
| II-74 | CH=NNH−C(=NH)NH₂ | H | CO₂CH₃ | OH | H |
| II-75 | CH=N−N(tetrazolyl) | H | CO₂CH₃ | OH | H |
| II-76 | CH=N−N(morpholino) | H | CO₂CH₃ | OH | H |
| II-77 | CH=N−N(CH₃)₂ | H | CO₂CH₃ | OH | H |
| II-78 | CH=N−N(4-methylpiperazinyl) | H | CO₂CH₃ | OH | H |
| II-79 | CH₂S(CH₂)₂NH-n-C₄H₉ | H | CO₂CH₃ | OH | H |
| II-80 | CH₂S(CH₂)₂N(CH₃)₂ | CH₂S(CH₂)₂N(CH₃)₂ | CO₂CH₃ | OH | H |
| VI-1$^{(12)}$ | H | H | CO₂CH₃ | OH | H |
| VI-2$^{(13)}$ | H | NH₂ | CO₂CH₃ | OH | H |

$^{(1)}$Z¹ and Z² are both hydrogen, or both are combined together to represent oxygen, where indicated.
$^{(2)}$NH-amino acid linkage is an amide bond through the carboxyl group of the amino acid.
$^{(3)}$X and R are combined together to form the linking group.
$^{(7)}$Compound is in the form of the hydrochloride.
$^{(12)}$R⁸ = NHCONHC₂H₅.
$^{(13)}$R⁸ = NH₂.

18. The method of claim 17, wherein said functional derivative is Compound II-3.

19. The method of claim 17, wherein said functional derivative is Compound II-20.

20. The method of claim 17, wherein said functional derivative is Compound II-30.

21. The method of claim 17, wherein said functional derivative is Compound II-33.

22. The method of claim 17, wherein said functional derivative is Compound II-38.

23. The method of claim 17, wherein said functional derivative is Compound II-49.

24. The method of claim 17, wherein said functional derivative is Compound II-51.

25. The method of claim 17, wherein said functional derivative is Compound II-65.

26. The method of claim 17, wherein said functional derivative is Compound II-69.

27. The method of claim 17, wherein said functional derivative is Compound II-72.

28. The method of claim 17, wherein said functional derivative is Compound II-73.

29. The method of claim 17, wherein said functional derivative is Compound II-79.

30. The method of claim 17, wherein said functional derivative is Compound II-80.

31. The method of claim 17, wherein said functional derivative is Compound VI-1.

32. The method of claim 17, wherein said functional derivative is Compound VI-2.

33. The method of claim 17, wherein said neuron is a cholinergic neuron.

34. The method of claim 17, wherein said sensory neuron is a dorsal root ganglion neuron, and said compound is represented by formula (II):

(II) [structure with R¹, R², Z¹, Z², Me, R, X substituents on fused ring system]

wherein the following substitutions are made:

| Compound$^{(1)}$ | R¹ | X | R | Z¹$^{(2)}$ / Z² |
|---|---|---|---|---|
| II-1 | H | CH₂N₃ | OH | H |
| II-2 | NHCONHC₆H₅ | CO₂CH₃ | OH | H |
| II-3 | CH₂SOC₂H₅ | CO₂CH₃ | OH | H |
| II-4 | H | CH₂OH | OCH₃ | H |
| II-5 | H | CONHC₂H₅ | OH | H |
| II-6 | H | CH=NNH−(imidazolyl) | OH | H |
| II-8 | H | CON(CH₃)₂ | OH | H |
| II-9$^{(3)}$ | H | −CH₂NHCO₂− | | H |
| II-10 | Br | CO₂CH₃ | OH | H |
| II-11 | H | CONH₂ | OH | H |

-continued

| Compound[1] | R[1] | X | R | $Z^{1(2)}$ $Z^2$ |
|---|---|---|---|---|
| II-12 | H | CH$_2$OH | OH | H |
| II-13 | H | CONHC$_3$H$_7$ | OH | H |
| II-15 | H | CH$_2$SOCH$_3$ | OH | H |
| II-17 | H | CON O | OH | H |
| II-19 | H | CH=NNHC(=NH)NH$_2$ | OH | H |
| II-20[1] | Br | CO$_2$CH$_3$ | OH | O |
| II-21 | H | CONH(CH$_2$)$_2$OH | OH | H |
| II-23 | H | H | OH | H |
| II-24 | H | CH=NNHCONH$_2$ | OH | H |
| II-25 | H | CH$_2$OCOCH$_3$ | OH | H |
| II-30 | CH$_2$SC$_2$H$_5$ | CO$_2$CH$_3$ | OH | H |
| II-32 | Br | CO$_2$CH$_3$ | OH | H |

[1]R$^2$ is hydrogen, except in compound II-20 and II-32 where R$^2$ = Br.
[2]Z$^1$ and Z$^2$ are both hydrogen, or both are combined together to represent oxygen, where indicated.
[3]X and R are combined together to form the linking group.

35. The method of claim 1 wherein said composition is administered in conjunction with a trophic factor.

36. The method of claim 3, wherein said composition is administered in conjunction with a trophic factor.

37. The method of claim 17 wherein said functional derivative is administered in conjunction with a trophic factor.

38. The method of claim 34 wherein said functional derivative is administered in conjunction with a trophic factor.

39. The method of any one of claims 35–38, wherein said trophic factor is a member of the neurotrophin family.

40. The method of claim 39 wherein said member of the neurotrophin family is nerve growth factor (NGF).

41. The method of claim 17, wherein said neuron is a cholinergic neuron, and said functional derivative is represented by the formula (II):

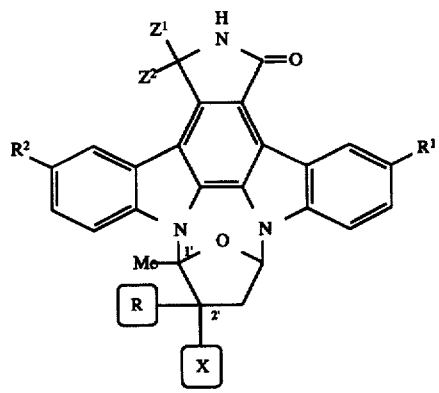

wherein R$^1$ and R$^2$ are H; X is CO$_2$CH$_3$; R is OH; and Z$^1$ and Z$^2$ are each H.

42. The method of claim 17, wherein said neuron is a striatal neuron, and said compound is represented by formula (II):

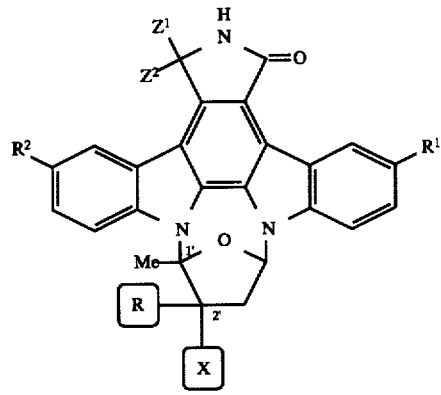

wherein the following substitutions are made:

| Compound | R$^1$ | R$^2$ | X | R | $Z^{2(1)}$ $Z^1$ |
|---|---|---|---|---|---|
| II-1 | H | H | CH$_2$N$_3$ | OH | H |
| II-35 | H | H | CO$_2$n-C$_6$H$_{13}$ | OH | H |
| II-20 | Br | Br | CO$_2$CH$_3$ | OH | O |
| II-10 | Br | H | CO$_2$CH$_3$ | OH | H |
| II-28 | O-n-C$_3$H$_7$ | H | CO$_2$CH$_3$ | OH | H |
| II-5 | H | H | CONHC$_2$H$_5$ | OH | H |
| II-29 | NHCONHC$_2$H$_5$ | H | CO$_2$CH$_3$ | OH | H |
| II-2 | NHCONHC$_6$H$_5$ | H | CO$_2$CH$_3$ | OH | H |
| II-3 | CH$_2$SOC$_2$H$_5$ | H | CO$_2$CH$_3$ | OH | H |
| II-30 | CH$_2$SC$_2$H$_5$ | H | CO$_2$CH$_3$ | OH | H |
| II-6 | H | H | CH=NNH—(imidazole) | OH | H |
| II-31 | Br | H | CH$_2$OH | OH | H |
| II-32 | Br | Br | CO$_2$CH$_3$ | OH | H |
| II-33 | CH$_2$SC$_6$H$_5$ | H | CO$_2$CH$_3$ | OH | H |
| II-34 | Cl | Cl | CO$_2$CH$_3$ | OH | H |

[1]Z$^1$ and Z$^2$ are both hydrogen, or both are combined together to represent oxygen, where indicated.
[2]R$^3$ is CH$_2$—CH=CH$_2$; R$^4$ is H.

43. The method of claim 17, wherein said neuron is a basal forebrain neuron, and said functional derivative is represented by the formula II:

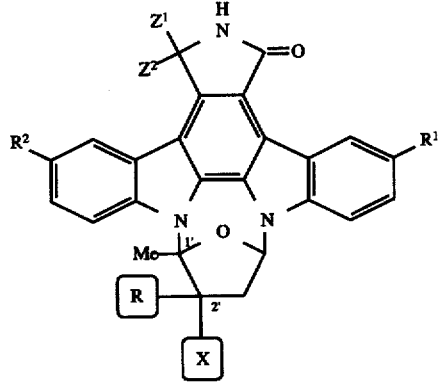

wherein the following substitutions are made:

| Compound | $R^1$ | $R^2$ | X | R | $Z^2, Z^1$ |
|---|---|---|---|---|---|
|  | H | H | $CO_2CH_3$ | OH | H |
| II-3 | $CH_2SOC_2H_5$ | H | $CO_2CH_3$ | OH | H |
| II-5 | H | H | $CONHC_2H_5$ | OH | H |
| II-10 | Br | H | $CO_2CH_3$ | OH | H |
| II-20 | Br | Br | $CO_2CH_3$ | OH | O |
| II-21 | H | H | $CONH(CH_2)_2OH$ | OH | H |
| II-22 | H | H | $CO_2CH_3$ | OH | O |
| II-30 | $CH_2SC_2H_5$ | H | $CO_2CH_3$ | OH | H |
| II-32 | Br | Br | $CO_2CH_3$ | OH | H |
| II-51 | $CH_2SC_2H_5$ | $CH_2SC_2H_5$ | $CO_2CH_3$ | OH | H |
| II-62 | H | H | $CO_2$n-hexyl | OH | H |
| II-63 | OH | H | $CO_2CH_3$ | OH | H |
| II-64 | O n-propyl | H | $CO_2CH_3$ | OH | H |
| II-65 | $CH_2SCH_2CH_2N(CH_3)_2$ | H | $CO_2CH_3$ | OH | H |

[1] $Z^1$ and $Z^2$ are both hydrogen, or both are combined together to represent oxygen, where indicated.

\* \* \* \* \*